United States Patent
Fairlie et al.

(10) Patent No.: US 9,868,763 B2
(45) Date of Patent: *Jan. 16, 2018

(54) MODULATORS OF PROTEASE ACTIVATED RECEPTORS

(75) Inventors: David Fairlie, Brisbane (AU); Ligong Liu, Brisbane (AU); Mei-Kwan Yau, Brisbane (AU); Jacky Yung Suen, Brisbane (AU); Robert Reid, Brisbane (AU); Rink-Jan Lohman, St Lucia (AU); Abishek Venkatasubramanian Iyer, St Lucia (AU); Junxian Lim, Indooroopilly (AU); Lindsay Charles Brown, Sinnamon Park (AU)

(73) Assignee: The University of Queensland, St. Lucia (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/235,640

(22) PCT Filed: Jul. 27, 2012

(86) PCT No.: PCT/AU2012/000891
§ 371 (c)(1),
(2), (4) Date: May 14, 2014

(87) PCT Pub. No.: WO2013/013273
PCT Pub. Date: Jan. 31, 2013

(65) Prior Publication Data
US 2014/0315796 A1 Oct. 23, 2014

(30) Foreign Application Priority Data
Nov. 7, 2011 (AU) .............................. 2011904617

(51) Int. Cl.
| | | |
|---|---|---|
| *C07K 5/08* | (2006.01) | |
| *A61K 38/05* | (2006.01) | |
| *C07K 5/065* | (2006.01) | |
| *C07K 5/02* | (2006.01) | |
| *C07K 5/06* | (2006.01) | |

(52) U.S. Cl.
CPC ............... *C07K 5/08* (2013.01); *A61K 38/05* (2013.01); *C07K 5/02* (2013.01); *C07K 5/06* (2013.01); *C07K 5/06078* (2013.01)

(58) Field of Classification Search
None
See application file for complete search history.

(56) References Cited

U.S. PATENT DOCUMENTS

| 4,522,811 A | 6/1985 | Eppstein et al. | |
|---|---|---|---|
| 5,578,593 A | 11/1996 | Chen et al. | |
| 8,927,503 B2 * | 1/2015 | Fairlie et al. | 514/21.9 |
| 2015/0038402 A1 * | 2/2015 | Fairlie et al. | 514/1.7 |

FOREIGN PATENT DOCUMENTS

| WO | WO 2012/012843 A1 | 2/2012 |
|---|---|---|
| WO | WO 2012012843 A1 * | 2/2012 |
| WO | WO 2012/033518 A1 | 3/2012 |

OTHER PUBLICATIONS

Alberti et al. "International Diabetes Federation: a consensus on Type 2 diabetes prevention" Diabetic Medicine 24:451-463.*
Anonymous. "Facts About Cystic Fibrosis" NIH Publication 95/3650. Published Nov. 1995.*
Anonymous. "How Can Metabolic Syndrome Be Prevented?" NHLBI, NIH. https://www.nhlbi.nih.gov/health/health-topics/topics/ms/prevention. Published Nov. 3, 2011.*
Badeanlou et al. "Tissue factor-protease-activated receptor 2 signaling promotes diet-induced obesity and adipose inflammation" Nature Medicine 17:1490-1498. Published online Oct. 23, 2011.*
Barry et al. "Novel Agonists and Antagonists for Human Protease Activated Receptor 2" J. Med. Chem. 53:7428-7440. Published online Sep. 28, 2010.*
Barry, et al., "Novel Agonists and Antagonists for Human Protease Activiated Receptor 2", Journal of Medicinal Chemistry, Sep. 28, 2010, vol. 53(20), 7428-7440.
Barry, et al, "A Refined Agonist Pharmacophore for Protease Activated Receptor 2", Bioorg Med. Chem., 2007, vol. 17, 5552-7.
Berge, et al., "Pharmaceutical Salts", J. Pharm. Sci., Jan. 1977, 66(1), 1-19.
Boitano, et al., Potent Agonists of the Protease Activated Receptor 2 (PAR2), J Med Chem., Mar. 10, 2011, 54(5), 1308-13.
Chawla, "Control of Macrophage Activation and Function by PPARs", Circ. Res, May 28, 2010, vol. 106(10), 1559-69.
Dandona, et al., "Metabolic Syndrome: A Comprehensive Perspective Based on Interactions Between Obesity, Diabetes, and Inflammation", Circulation, 2005, 111, 1448-54.

(Continued)

*Primary Examiner* — Christina Bradley
*Assistant Examiner* — Zachary J Miknis
(74) *Attorney, Agent, or Firm* — Baker Hostetler LLP

(57) ABSTRACT

The present invention provides novel compounds of the Formula (I), pharmaceutical compositions comprising such compounds and methods for using such compounds as tools for biological studies or as agents or drugs for therapies such as metabolic syndrome, obesity, type II diabetes, fibrosis and cardiovascular diseases, whether they are used alone or in combination with other treatment modalities.

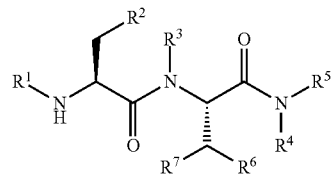

7 Claims, 24 Drawing Sheets

(56) References Cited

OTHER PUBLICATIONS

Earp, et al., "Pharmacokinetics of Dexamethasone in a Rat Model of Rheumatoid Arthritis", Biopharm Drug Dispos., Sep. 2008, 29(6), 366-372.
Ferrannini, "Is Insulin Resistance the Cause of the Metabolic Syndrome", Ann Med, 2006, 38(1), 42-51.
Flick, et al., "Fibrin(ogen) Exacerbates Inflammatory Joint Disease Through a Mechanism Linked to the Integrin amB2 Binding Motif", J. Clin Invest., Oct. 2007, 117(11), 3224-3235.
Flynn, et al., "The Protease-Activated Receptor-2-Specific Agonists 2-Aminothiazol-4-yl-LIGRL-NH2 and 6-Aminonicoinyl-LIGRL-NH2 Stimulate Multiple Signaling Pathways to Induce Physiological Responses inVitro and In Vivo", J Biological Chem., May 27, 2011, vol. 286(21), 19076-88.
Goh, et al., "Dual Effect of the Novel Peptide Antagonist K-14585 on Proteinase-Activated Receptor-2-Mediated Signaling", Br J. Pharmacol, 2009, 158, 1695-1704.
Hollenberg, et al., Pharmacol Exp Ther. 2008, 326, 453-62.
Iyer, et al.,"Lipid Mediators and Inflammation in Glucose Intolerance and Insulin Resistance", Drug Discovery Today: Disease Mechanisms, 2011, 7 pgs.
Kanke, et al., "Novel Antagonists for Proteinase-Activated Receptor 2: Inhibition of Cellular and Vascular Responses in Vitro and in Vivio", Br J. Pharmacol, Sep. 2009, 158(1), 361-371.
Kawabata, et al., "The PAR-1-Activating Peptide Attenuates Carrageenan-Induced Hyperalgesia in Rats", Peptide, 2001, vol. 23(6),1181-3.
Kelso, et al., "Therapeutic Promise of Proteinase-Activated Receptor-2 Antagonism in Join Inflammation", J. Pharmacol Exp. Ther., Mar. 2006, 316(3), 1017-24.
Kelso, et al., "Expression and Proinflammatory Role of Proteinase-Activated Receptor 2 in Reheumatoid Synovium: Ex Vivo Studies Using a Novel Proteinase-Activated Receptor 2 Antagonist", Arthritis Rheum., Mar. 2007, 56(3), 765-71.
Lin, et al., "Anti-Rheumatic Activities of Histone Deacetylase (HDAC) Inhibitors In Vivi in Collagen—Induced Arthritis in Rodents", Br J Pharmacol, Apr. 2007, 150(7), 862-72.
Liu, et al., "Genetic Deficiency and Pharmacological Stabilization of Mast Cells Reduce Diet-Induced Obesity and Diabetes in Mice", Nat Med, Aug. 2009, 15(8), 940-45.
Lumeng, et al., "Obesity Induces a Phenotypic Switch", J. Clin. Invest, Jan. 2007, vol. 117(1), 175-84.
Iyer, et al., "Inflammatory Lipid Mediators in Adipocyte Function and Obesity", Nal Rev Endocrinol, Oct. 2009, vol. 6, 71-82.
McGuire, et al, "2-furoyl-LIGRLO-amide: A Potent and Selective Proteinase-Activated Receptor 2 Agonist", Pharmacol Exp Ther, Jun. 2004, vol. 309(3), 1124-31.
Memon, et al., "Up-regulation of Peroxisome Proliferator-Activated Receptors (PPAR-alpha) and PPAR-gamma Messenger Ribonucleic Acid Expression in the Liver in Murine Obesity: Troglitazone Induces Expression of PPAR-gamma-Responsive Adipose Tissue-Specific Genes in the Liver of Obese Diabetic Mice", Endocrinology, Nov. 2000, vol. 141(11),4021-31.
Nishikawa, et al., "Prevention of the Onset and Progression of Collagen-Induced Arthritis in Rats by the Potent p38 Mitogen-Activated Protein Kinase Inhibitor FR167653", Arthritis Rheum., Sep. 2003, 48(9), 2670-81.
Nishimura, et al., "CD8+ Effector T Cells Contribute to Macrophage Recruitment and Adipose Tissue Inflammation in Obesity", Nat Med., Aug. 2009, vol. 15(8), 914-20.
Odegaard, et al., "Macrophage-Specific PPARgamma Controls Alternative Activation and Improves Insulin Resistance", Nature, Jun. 28, 2007, vol. 447, 1116-20.
Olofsson, et al., "A Comparative Genetic Analysis Between Collagen-Induced Arthritis and Pristane-Induced Arthritis", Arthritis Rheum 2003, vol. 48(8), 2332-42.
Ong, et al., Manipulation of Dietary Short Chain Carbohydrates Alters the Pattern of Gas Production and Genesis of Symptoms in Irritable Bowel Syndrome, Hepatology, Aug. 2010, 25(8), 1366-1373.
Potenza, et al., "The Metabolic Syndrome: Definition, Global Impact, and Pathophysiology", Nutrition in Clinical Practice, 2009, vol. 24(5), 560-77.
Reaven, "Banting Lecture 1988. Role of Insulin Resistance in Human Disease", Diabetes, Dec. 1988, 37(12), 1595-1607.
Seitzberg, et al., "Discovery of Potent and Selective Small-Molecule PAR-2 Agnists", J Med Chem., Sep. 2008, 51(18), 5490-3.
Simmons, et al., "The Metabolic Syndrome: Useful Concept or Clinical Tool? Report of a WHO Expert Consultation", Diabetologia, Apr. 2010, vol. 53(4), 600-5.
Sookoian, et al., "Epigenetic Regulation of Insulin Resistance in Nonalcoholic Fatty Liver Disease: Impact of Liver Methylation of the Peroxisome Proliferator-Activated Receptor γ Coactivator 1α Promoter", Hepatology, Dec. 2010, vol. 52(6), 1992-2000.
Suen, et al., Modulating Human Proteinase Activated Receptor 2 with a Novel Antagonist (GB88) and Agonist (GB110), Br J. Pharmacol, Mar. 2012, vol. 165(5), 1413-1423.
Symonds, et al., "Nutritional Programming of the Metabolic Syndrome", Nat Rev Endocrinol, Nov. 2009, 5(11), 604-10.
Van Gaal, et al, "Mechanisms Linking Obesity with Cardiovascular Disease", Nature, 2006, 444(7121), 875-80.
Vergnolle, Proteinase-Activated Receptor-2-Activating Peptides Induce Leukocyte Rolling, Adhesion, and Extravasation J Immunol 1999, 163(9), 5064-9.
Woodruff, et al, "Antiarthritic Activity of an Orally Active C5a Receptor Antagonist Against Antigen-Induced Monarticular Arthritis in the Rat", Arthritis Rheum, Sep. 2002, vol. 46(9), 2476-85.
Zimmet, et al., "Mainstreaming the Metabolic Syndrome: A Definitive Definition", Med J. Aug. 2005, 183(4), 175-6.
Adams et al., "Structure, function and pathophysiology of protease activated receptors", Pharmacology & Therapeutics, 2011, 130, 248-282.
Regard et al., "Probing cell type-specific functions of $G_i$ in vivo identifies GPCR regulators of insulin secretion", The Journal of Clinical Investigation, Dec. 2007, vol. 117, No. 12, 4034-4043.
Yau et al., "Novel agonists and antagonists for protease activated receptor 2", MEDI, Aug. 28, 2011, 1 page.

* cited by examiner

MODULATORS OF PROTEASE ACTIVATED RECEPTORS

CROSS-REFERENCE TO RELATED APPLICATIONS

The present application is the United States National Phase of PCT Application No. PCT/AU2012/000891, filed Jul. 27, 2012, which claims priority to PCT/AU2011/000959, filed Jul. 28, 2011, and to AU 2011904617, filed Nov. 7, 2011, the entire contents of each of which are incorporated herein by reference.

FIELD OF THE INVENTION

The present invention relates generally to compounds capable of modulating Protease Activated Receptor-2 (PAR2), and uses thereof. More specifically, the present invention relates to modulators of PAR2, to their preparation, and to their use as tools for biological studies or as agents or drugs for therapies such as metabolic syndrome, obesity, type II diabetes, fibrosis and cardiovascular diseases, whether they are used alone or in combination with other treatment modalities.

BACKGROUND

Protease activated receptor-2 (PAR2) is a unique G-protein coupled receptor (GPCR) in that it has no known endogenous extracellular ligand, but rather is activated by proteases including many serine proteases such as trypsin, tryptase, and cathepsin Q. Serine proteases cleave a section of the membrane bound receptor's extracellular N-terminus, exposing a new sequence which acts as a tethered ligand by binding to the receptor and initiating activation.

Distributed widely throughout the body, PAR2 has been implicated as a pro-inflammatory mediator in acute and chronic inflammatory diseases including arthritis, inflammatory bowel disease, pancreatitis, and cardiovascular diseases. PAR2 has also been reported as anti-inflammatory and protective in conditions such as gastric ulcer, colitis, asthma, and liver fibrosis, although this remains controversial. PAR2 activation has been linked to proliferation, metastasis and angiogenesis in many cancers including cancers or the stomach, colon, breast and pancreas. In this context, small-molecule modulators of PAR2 are of potential interest as a new class of anti-inflammatory, pro-inflammatory, anti-proliferative or proliferative agents.

Recently, interest has grown in inflammatory GPCRs as novel therapeutic targets for diet-induced obesity and metabolic syndrome after the identification of increased circulation of various pro-thrombotic molecules (such as plasminogen activator inhibitor-1, tissue factors) and other cysteine/serine proteases (such as cathepsins, caspases, tryptase, factor VII, factor X, trypsin-like serine proteases) that have been implicated in these disorders.

Human diets increasingly high in saturated fats and carbohydrates are thought to overload metabolic and immune systems, leading to obesity, metabolic dysfunction and impaired immunity. This excessive nutrient intake induces a chronic inflammatory state in adipose tissue promoting obesity, altering adipocyte function and immune cell distribution, both of which appear to trigger metabolic dysfunction. Chronic metabolic dysfunction can lead to obesity, type II diabetes and cardiovascular disease, their treatments representing major challenges to global health systems (Iyer, A., et al, Nat Rev Endocrinol 2009, 6, 71-82; Iyer, A. & Brown, L. *Drug Discovery Today: Disease Mechanisms* 2011). Modern sedentary lifestyles coupled with excessive caloric intake are important factors in initiating obesity and associated metabolic and cardiovascular disorders that are now collectively referred to as the 'metabolic syndrome' (Potenza, M. V. & Mechanick, J. I., *Nutrition in Clinical Practice* 2009, 24, 560-77; Simmons, R. K. et al. *Diabetologia* 2010, 53, 600-5).

Metabolic syndrome is associated with complications such as excessive visceral fat deposition, hypertension, impaired glucose and insulin homeostasis, insulin resistance, endothelial damage, cardiovascular hypertrophy, inflammation, vascular inflammation, atherosclerosis, ventricular contractile dysfunction, fibrosis and fatty liver disease. Identifying effective therapeutic and preventive options to treat this multi-factorial syndrome has proven to be very challenging, with an emerging focus on developing anti-inflammatory agents that can combat adiposity, metabolic and cardiovascular dysfunction as chronic inflammation has been shown to play a major role in both initiation and progression of obesity and metabolic syndrome.

Among the dynamic components of adipose tissue are adipocytes as well as many different immune cells such as macrophages, monocytes, T-cells and mast cells that contribute indirectly to adipocyte function. Alteration in the population of immune cells (especially macrophages) resident in adipose tissue early during the development of obesity is currently thought to propagate oxidative and inflammatory cascades triggering adiposity and metabolic dysfunction. Signals that initiate macrophage activation in adipose tissue are unknown. A growing body of evidence suggests that saturated fatty acids and lipid mediators produced locally by adipocytes and/or macrophages can, at least in part, participate in inflammatory cell activation, adipocyte growth, development and dysfunction and, therefore, contribute to obesity and metabolic disturbances. Various inflammatory lipid-induced G protein-coupled receptors (GPCRs) are thought to signal intracellular proteins that contribute to regulation of obesity, adipose tissue immune cell-dependent inflammation, insulin secretion and cardiovascular homeostasis.

Trypsin is a potent activator of PAR2 in the GI tract where pancreatic trypsin is found, and in colon, airway epithelium, neuronal and vascular endothelial cells, skin, intestine, kidney and pancreas where trypsinogen expression has been demonstrated. Mast cell tryptase is also an important activator of PAR2, being highly expressed in mast cells and strongly associated with many inflammatory, endocrine and other diseases. Pro-thrombotic factors such as tissue factor VIIa have also been implicated in the cleavage of PAR2, exposing receptor activating sequences encoded within the N-terminus, thereby activating PAR2 signal transduction in adipose tissue and macrophages. Hexapeptides SLIGKV-$NH_2$ and SLIGRL-$NH_2$, corresponding to the tethered ligand human and murine sequences respectively, can activate human PAR2 in lieu of serine proteases, albeit at lower potency (μM instead of nM concentrations).

More potent peptide agonists have been created for PAR2. The hexapeptide analogue, 2-furoyl-LIGRL-$NH_2$, has ~20-fold higher agonist potency than SLIGRL-$NH_2$ and is selective for PAR2 over PAR1 and PAR4. Other heterocyclic replacements for serine result in equipotent PAR2 agonists, while large aromatic groups in place of the C-terminal leucine impart a similar enhancement in PAR2 agonist potency (McGuire, J. J. et al, J Pharmacol Exp Ther 2004, 309, 1124-31; Barry G. D. et al, Bioorg Med Chem 2007, 27, 5552-7; Hollenberg, M. D., et al, J Pharmacol Exp Ther 2008, 326, 453-62; Boitano, C., et al, *J Med Chem* 2011, 54, 1308-13; Flynn, A. N., et al, J Biological Chem 2011, 286, 19076-88). Screening of 250,000 drug-like compounds produced two small molecule agonists of PAR2 with similar agonist potency to 2-furoyl-LIGRL-NH$_2$, some selectivity for PAR2 and metabolic stability in vivo (Seitzberg, J. G., et al. *J Med Chem* 2008, 51, 5490-3).

The first known antagonist of PAR2 had affinity at only millimolar concentrations for the receptor and selectivity for PAR2 over non-PAR receptors is most unlikely (Kelso, E. B., et al. *J Pharmacol ExpTher* 2006, 316, 1017-24). A second antagonist reported for PAR2 is active at μM concentrations, but completely inactive against endogenous PAR2 activators like trypsin, tryptase and other proteases (Kanke, T, et al. *Br J Pharmacol* 2009, 158, 361-371) or has a dual function as an antagonist and agonist due to either partial agonist actions or possible agonist-directed signalling (Goh, F. G., et al. *Br J Pharmacol* 2009, 158, 1695-1704). More recently, a PAR2 antagonist with activity at low micromolar concentrations has been reported and was found to be selective for PAR2 over other PARs, reversibly inhibiting receptor activation by proteases and synthetic PAR2 agonists (Barry G. D. et al, J. Med. Chem. 2010, 53, 7428-40).

In one aspect the present invention advantageously provides a novel class of compounds that Can selectively modulate PAR2 when used at as low as micromolar or sub-micromolar concentrations. Depending upon structural characteristics, and intracellular pathways being examined, these novel compounds may act as either agonists or antagonists and be useful as tools for biological studies or as agents for anti-inflammatory, pro-inflammatory, anti-proliferative or proliferative therapies.

Current treatments for obesity act by reducing or controlling weight in patients by altering appetite, metabolism or absorption of calories and nutrients from food, for example, Orlistat (Xenical) is currently approved by the FDA for long term use. Orlistat reduces intestinal fat absorption by inhibiting pancreatic lipase. A second medicament, Rimonabant (Acomplia) works via a specific blockade of the endocannabinoid system. The FDA approved combination drug Qsymia comprises phentermine, a stimulant that suppresses the appetite and topiramate, an anticonvulsant. However, until now, the role of inhibitors of PAR2 in the reversal or attenuation of the symptoms of metabolic syndrome has not been reported.

Surprisingly, it has now been found that particular antagonists of PAR2 are able to reverse, prevent or attenuate obesity, metabolic syndrome and its associated diseases and disorders including adipose inflammation, type II diabetes, fibrosis and cardiovascular diseases.

Accordingly, in another aspect the present invention advantageously provides the use of PAR2 antagonists in the treatment and/or prevention of metabolic syndrome, obesity, adipose inflammation, type II diabetes, fibrosis and cardiovascular disease. Aspects of the present invention are based on the revelation that the action of PAR2 antagonism is effective in treatment and/or prevention of metabolic syndrome, obesity, insulin and glucose intolerance that are characteristic of type II diabetes, cardiovascular irregularities that are characteristic of cardiovascular diseases, and fibrosis as defined by collagen deposition.

Crohn's disease and ulcerative colitis are common forms of inflammatory bowel disease (IBD) that share common pathologies. Ulcerative colitis affects the colon and rectum and Crohn's disease affects multiple regions of the colon and ileum, and each condition has characteristic pasterns of ulcerative mucosa. Surprisingly, it has now been found that antagonists of PAR2 are able to prevent or attenuate inflammatory bowel disease with improved efficacy compared to current treatments. Accordingly, in another aspect the present invention advantageously provides the use of PAR2 antagonists in the treatment and/or prevention of inflammatory bowel disease.

SUMMARY OF THE INVENTION

In one aspect, the present invention provides compounds of the formula (I):

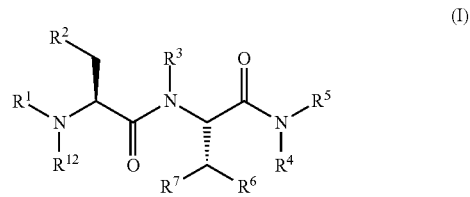

wherein
R$^1$ is hydrogen, C$_1$-C$_6$alkyl, aminoalkyl, hydroxyalkyl, or —C(O)R$^8$; wherein R$^8$ is a 5- or 6-membered saturated or unsaturated heterocyclic ring comprising 1 to 3 heteroatoms selected from N and O, optionally substituted with one or more substituents selected from alkyl, alkoxy, amine, aminoalkyl, amidoalkyl, halo, hydroxy, trihaloalkyl, trihaloalkoxy or phenyl, wherein the phenyl group may be further optionally substituted with 1 to 3 substituents selected from alkyl, alkoxy, hydroxy, halo, nitro, trihaloalkyl, or trihaloalkoxy; or
R$^1$, together with the nitrogen atom to which it is attached, forms a mono- or bicyclic-nitrogen containing heterocycle, optionally substituted with alkyl;
R$^2$ is an aromatic or aliphatic C$_3$-C$_8$cyclic group or C$_3$-C$_8$heterocyclic group comprising 1 to 3 heteroatoms selected from N and O, wherein the C$_3$-C$_8$cyclic group or C$_3$-C$_8$heterocyclic group may be further substituted with one or more substituents selected from alkyl, amine, hydroxy, or the cyclic group or heterocyclic group is fused with an optionally substituted aromatic or aliphatic C$_3$-C$_8$cyclic group or C$_3$-C$_8$heterocyclic group;
R$^3$ is hydrogen or C$_1$-C$_6$alkyl;
R$^4$ is hydrogen, C$_1$-C$_6$alkyl, aminoalkyl or amidoalkyl;
R$^5$ is a benzyl group optionally substituted with a group selected from alkyl, aminoalkyl, alkoxy, C$_4$-C$_7$heterocycle, hydroxy, halo, nitro, dioxalane, trihaloalkyl, trihaloalkoxy or —C(O)NHCHR$^9$R$^{10}$; wherein R$^9$ is —C(O)NH$_2$ and R$^{10}$ is a C$_2$-C$_5$aminoalkyl; or
R$^4$ and R$^5$ combined, together with the nitrogen to which they are attached, form piperidine, optionally substituted with a group selected from phenyl, benzyl, aminoalkyl, aminoaryl, amidoalkyl or a heterocycle; or
R$^4$ and R$^5$ combined, together with the nitrogen to which they are attached, form piperidine fused with an aromatic or aliphatic C$_3$-C$_8$cyclic group or C$_3$-C$_8$heterocyclic group;
wherein the phenyl, benzyl, aminoaryl, heterocycle or the aromatic or aliphatic C$_3$-C$_8$cyclic group or C$_3$-C$_8$heterocyclic group fused with piperidine may be further substituted with 1 to 3 substituents selected from alkyl, alkylamine, alkylamide, alkylsulfonyl, alkoxy, aminoalkyl, aminoaryl, amidoalkyl, arylamine, hydroxy, halo, nitro, oxo, optionally substituted phenyl, optionally substituted piperidine, dioxalane, trihaloalkyl, or trihaloalkoxy; or the aromatic or aliphatic $C_3$-$C_8$cyclic group or $C_3$-$C_8$heterocyclic group fused with the piperidine is further fused with an additional $C_6$-$C_{10}$cyclic or $C_6$-$C_{10}$heterocyclic group;

$R^6$ is hydrogen or $C_1$-$C_6$alkyl;

$R^7$ is $C_1$-$C_6$alkyl, amino, hydroxy, alkoxy, aminoalkyl, amidoalkyl, saturated or unsaturated cycloalkyl, or heterocycle; or $R^6$ and $R^7$ combined, together with the carbon to which they are attached, form $C_5$-$C_8$ aromatic or aliphatic cyclic group or heterocyclic group, optionally substituted with a group selected from alkyl, aminoalkyl, alkoxy, hydroxy, halo, nitro, trihaloalkyl or trihaloalkoxy; and $R^{12}$ is hydrogen or $C_1$-$C_6$alkyl; and salts thereof;

provided that the compound is not 5-isoxazoyl-Cha-Ile-spiro[indene-1,4'-piperidine], 5-isoxazoyl-Cha-Ile-spiro[indane-1,4'-piperidine], 5-isoxazoyl-Cha-Ile-spiro[octahydro-1H-indene-1,4'-piperidine] or 5-isoxazoyl-Cha-Ile-1,2,3,4-tetrahydroisoquinoline.

In a further aspect, the present invention provides compounds of formula (I) represented by the formula (Ia):

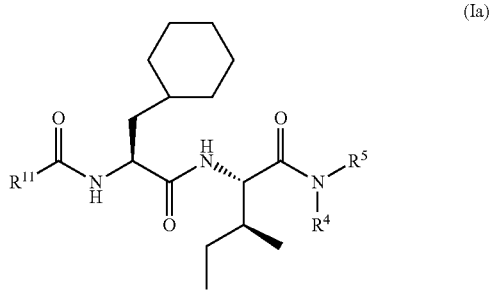

(Ia)

wherein $R^{11}$ is a 5- or 6-membered unsaturated heterocyclic ring comprising 1 to 3 heteroatoms selected from N and O, optionally substituted with one or more groups selected from alkyl amino, or phenyl, wherein the phenyl group may be further optionally substituted with 1 to 3 substituents selected from alkyl, alkoxy, hydroxy, halo, nitro, trihaloalkyl or trihaloalkoxy;

$R^4$ is hydrogen, $C_1$-$C_6$alkyl, aminoalkyl or amidoalkyl;

$R^5$ is a benzyl group, optionally substituted with a group selected from alkyl, aminoalkyl, alkoxy, $C_4$-$C_7$heterocycle, hydroxy, halo, nitro, dioxalane, trihaloalkyl, trihaloalkoxy or —C(O)NHCHR$^9$R$^{10}$; wherein $R^9$ is —C(O)NH$_2$ and $R^{10}$ is a $C_2$-$C_5$aminoalkyl; or $R^4$ and $R^5$ combined, together with the nitrogen to which they are attached, form piperidine, optionally substituted with a group selected from phenyl, benzyl, aminoalkyl, amidoalkyl or a heterocycle; wherein the phenyl, benzyl or heterocycle may be further substituted with 1 to 3 substituents selected from alkyl, alkyloxy, aminoalkyl, amidoalkyl, hydroxy, halo, nitro, dioxalane, trihaloalkyl, or trihaloalkoxy; and salts thereof.

In another aspect, the present invention provides a method of modulating the activity of PAR2 comprising exposing the receptor to a compound of the present invention, or a salt thereof.

In one aspect the compounds of the present invention are PAR2 antagonists.

In a further aspect the compounds of the invention are PAR2 agonists.

In a further aspect the compounds of the invention may be PAR2 antagonists in a given assay but PAR2 agonists in a different assay, pursuant to being 'biased' ligands for particular intracellular signalling pathways mediated by PAR2.

In a further aspect, the present invention provides pharmaceutical compositions comprising a compound of the present invention, or a salt thereof, preferably together with a pharmaceutically acceptable carrier, excipient, diluent and/or adjuvant.

In still a further aspect, the present invention provides a prophylactic or therapeutic method of treating a subject at risk of or susceptible to a disease or disorder, or having a disease or disorder associated with undesirable PAR2 activity, comprising administering a compound according to the present invention, or a salt thereof, to a subject in need thereof. Preferably, the disease or disorder is an inflammatory disease or disorder, or a proliferative disease or disorder.

In another aspect, the present invention a method of treating or preventing a disease or disorder selected from metabolic syndrome, obesity, type II diabetes, fibrosis and cardiovascular diseases comprising administering to a subject in need thereof an effective amount of a PAR2 antagonist.

In a further aspect, the present invention provides a method of treating or preventing a disease or disorder selected from metabolic syndrome, obesity, type II diabetes, fibrosis and cardiovascular diseases comprising administering to a subject in need thereof an effective amount of a PAR2 antagonist represented by formula (I):

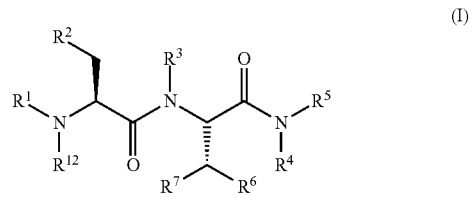

(I)

wherein $R^1$ is hydrogen, $C_1$-$C_6$alkyl, aminoalkyl, hydroxyalkyl, or —C(O)R$^8$; wherein $R^8$ is a 5- or 6-membered saturated or unsaturated heterocyclic ring comprising 1 to 3 heteroatoms selected from N and O, optionally substituted with one or more substituents selected from alkyl, alkoxy, amine, aminoalkyl, amidoalkyl, halo, hydroxy, trihaloalkyl, trihaloalkoxy or phenyl, wherein the phenyl group may be further optionally substituted with 1 to 3 substituents selected from alkyl, alkoxy, hydroxy, halo, nitro, trihaloalkyl, or trihaloalkoxy; or $R^1$, together with the nitrogen atom to which it is attached, forms a mono- or bicyclic-nitrogen containing heterocycle, optionally substituted with alkyl;

$R^2$ is an aromatic or aliphatic $C_3$-$C_8$cyclic group or $C_3$-$C_8$heterocyclic group comprising 1 to 3 heteroatoms selected from N and O, wherein the $C_3$-$C_8$cyclic group or $C_3$-$C_8$heterocyclic group may be further substituted with one or more substituents selected from alkyl, amine, hydroxy, or the cyclic group or heterocyclic group is fused with an optionally substituted aromatic or aliphatic $C_3$-$C_8$cyclic group or $C_3$-$C_8$heterocyclic group;

$R^3$ is hydrogen or $C_1$-$C_6$alkyl;

$R^4$ is hydrogen, $C_1$-$C_6$alkyl, aminoalkyl or amidoalkyl;

$R^5$ is a benzyl group optionally substituted with a group selected from alkyl, aminoalkyl, alkoxy, $C_4$-$C_7$heterocycle, hydroxy, halo, nitro, dioxalane, trihaloalkyl, trihaloalkoxy or —C(O)NHCHR$^9$R$^{10}$; wherein R$^9$ is —C(O)NH$_2$ and R$^{10}$ is a $C_2$-$C_5$aminoalkyl; or $R^4$ and $R^5$ combined, together with the nitrogen to which they are attached, form piperidine, optionally substituted with a group selected from phenyl, benzyl, aminoalkyl, aminoaryl, amidoalkyl or a heterocycle; or $R^4$ and $R^5$ combined, together with the nitrogen to which they are attached, form piperidine fused with an aromatic or aliphatic $C_3$-$C_8$cyclic group or $C_3$-$C_8$heterocyclic group;

wherein the phenyl, benzyl, aminoaryl, heterocycle or the aromatic or aliphatic $C_3$-$C_8$cyclic group or $C_3$-$C_8$heterocyclic group fused with piperidine may be further substituted with 1 to 3 substituents selected from alkyl, alkylamine, alkylamide, alkylsulfonyl, alkoxy, aminoalkyl, aminoaryl, amidoalkyl, arylamine, hydroxy, halo, nitro, oxo, optionally substituted phenyl, optionally substituted piperidine, dioxalane, trihaloalkyl, or trihaloalkoxy; or the aromatic or aliphatic $C_3$-$C_8$cyclic group or $C_3$-$C_8$heterocyclic group fused with the piperidine is further fused with an additional $C_6$-$C_{10}$cyclic or $C_6$-$C_{10}$heterocyclic group;

$R^6$ is hydrogen or $C_1$-$C_6$alkyl;

$R^7$ is $C_1$-$C_6$alkyl, amino, hydroxy, alkoxy, aminoalkyl, amidoalkyl, saturated or unsaturated cycloalkyl, or heterocycle; or $R^6$ and $R^7$ combined, together with the carbon to which they are attached, form $C_5$-$C_8$ aromatic or aliphatic cyclic group or heterocyclic group, optionally substituted with a group selected from alkyl, aminoalkyl, alkoxy, hydroxy, halo, nitro, trihaloalkyl or trihaloalkoxy; and $R^{12}$ is hydrogen or $C_1$-$C_6$alkyl; and salts thereof.

In another aspect, the present invention provides a method of treating inflammatory bowel disease comprising administering a compound of the formula (I) according to the present invention, or a salt thereof, to a subject in need thereof.

In still a further aspect, the present invention provides the use of the compounds of formula (I), or salts thereof, for the prophylactic or therapeutic treatment of a subject at risk of or susceptible to a disease or disorder, or having a disease or disorder associated with undesirable PAR2 activity. Preferably, the disease or disorder is an inflammatory disease or disorder, or a proliferative disease or disorder.

In another aspect, the present invention provides the use of a PAR2 antagonist for the treatment or prevention of a disease or disorder selected from metabolic syndrome, obesity, type II diabetes, fibrosis and cardiovascular disease.

In a further aspect, the present invention provides the use of a PAR2 antagonist represented by compounds of the formula (I) as defined herein for the treatment or prevention of a disease or disorder selected from metabolic syndrome, obesity, type II diabetes, fibrosis and cardiovascular disease.

In still a further aspect, the present invention provides the use of the compounds of the formula (I), or salts thereof, in the manufacture of a medicament for the prophylactic or therapeutic treatment of a subject at risk of or susceptible to a disease or disorder, or having a disease or disorder associated with undesirable PAR2 activity. Preferably, the disease or disorder is an inflammatory disease or disorder, or a proliferative disease or disorder.

In another aspect, the present invention provides the use of a PAR2 antagonist in the manufacture of a medicament for the treatment or prevention of a disease or disorder selected from metabolic syndrome, obesity, type II diabetes, fibrosis and cardiovascular disease.

In a further aspect, the present invention provides the use of a PAR2 antagonist represented by compounds of the formula (I) as defined herein in the manufacture of a medicament for the treatment or prevention of a disease or disorder selected from, metabolic syndrome, obesity, type II diabetes, fibrosis and cardiovascular disease.

DETAILED DESCRIPTION OF THE INVENTION

Figure 1:
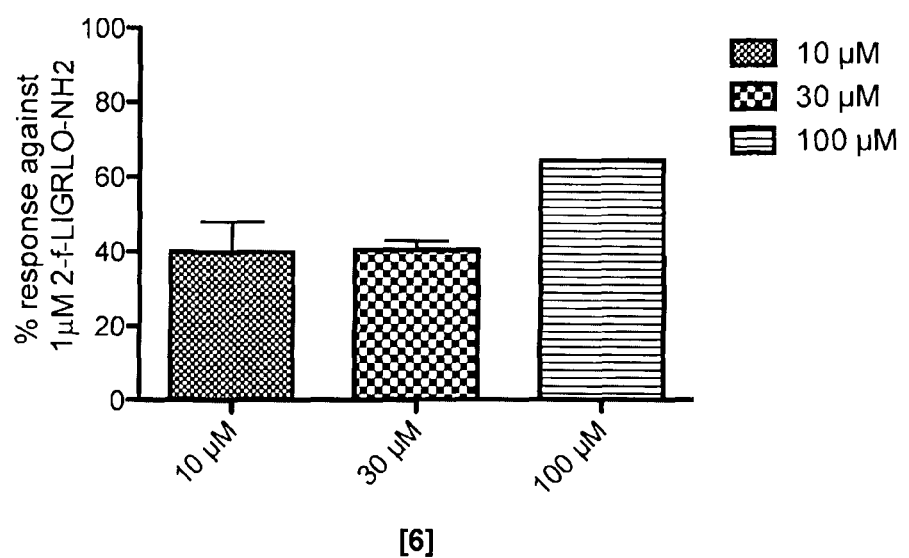
FIG. 1: Graphical representation of a three point concentration bar graph for PAR2 agonist 6 on HT29 cells.

Despite evidence of its apparent role in the aforementioned pathophysiologies, the biological function of PAR2 remains poorly understood, particularly at the in vivo level. This lack of substantial progress has been mostly attributed to a lack of potent and selective, bioavailable agonists and antagonists of PAR2 for the purposes of further investigation.

Structure activity relationship studies, starting from the hexapeptide agonists SLIGKV-NH$_2$ and SLIGRL-NH$_2$, have enabled the determination of the specific side-chain functionalities required for these peptidic ligands to bind to and activate PAR2. By utilising this information, it has been possible, for the first time, to rationally design and develop potent, selective and orally active non-peptidic modulators of the receptor. In the process, those fragments of the novel compounds that are required for receptor recognition and those regions that impart agonist or antagonist functionality have been determined. In some embodiments, these novel compounds provide a means of treating or preventing diseases or disorders associated with aberrant PAR2 expression and/or activity.

In this specification a number of terms are used which are well known to a skilled addressee. Nevertheless for the purposes of clarity a number of terms will be defined.

As used herein, the term "unsubstituted" means that there is no substituent or that the only substituents are hydrogen.

In this specification, unless otherwise defined, the term "optionally substituted" is taken to mean that a group may or may not be further substituted or fused (so as to form a condensed polycyclic group or a polycyclic spiro group) with one or more groups selected from hydroxyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocycloxy, oxyacyl, oxime, oxime ether, hydrazone, —NHC(NH)NH$_2$, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkylamino, mono- and di-arylamino, mono- and di-heteroarylamino, mono- and di-heterocyclyl, amino, and unsymmetric di-substituted amines having different substituents selected from alkyl, aryl, heteroaryl and heterocyclyl.

In certain embodiments the preferred substituent groups are one or more groups independently selected from alkyl, phenyl, alkoxy, halo, nitro, trihaloalkyl, trihaloalkyloxy or a group of the formula —C(O)NHCHR$^5$R$^6$ wherein R$^5$ is —C(O)NH$_2$ and R$^6$ is a C$_2$-C$_5$alkylamine.

"Alkyl" as a group or part of a group refers to a straight or branched aliphatic hydrocarbon group, preferably a C$_1$-C$_{10}$alkyl, more preferably a C$_1$-C$_8$alkyl, most preferably C$_1$-C$_6$ unless otherwise noted. Examples of suitable straight and branched C$_1$-C$_6$alkyl substituents include methyl, ethyl, n-propyl, 2-propyl, n-butyl, sec-butyl, t-butyl, hexyl, and the like.

The term "amino" herein refers to a nitrogen radical substituted with hydrogen, alkyl, aryl or combinations thereof.

In this specification, reference to amino acids including naturally occurring amino acids such as serine, leucine, isoleucine, glycine, arginine, lysine or valine, or amino acids that are not naturally occurring such as cyclohexylalanine, either by their complete name, their common three letter code (e.g. Ser, Leu, Ile, Gly, Arg, Lys, Val or Cha) or their single letter code (e.g. S, L, I, G, R, K or V) is taken to mean the L-isomer, unless otherwise specified.

The term "alkylamine" refers to an amine further bound to an alkyl group as defined herein and includes both mono- and di-alkylamines, unless specified. The alkyl group is preferably a C$_1$-C$_{10}$ alkyl group. The group is bonded to the remainder of the molecule through the nitrogen atom.

The term "alkylamide" refers to a group of the formula —C(O)NR$_2$ wherein at least one of the R substituents represents an alkyl group as defined herein. Alkylamides include both mono- and di-alkylamides, unless specified. One skilled in the art would recognise that in the case of mono-alkylamides the remaining R substituent represents hydrogen. The alkyl group is preferably a C$_1$-C$_{10}$alkyl group. The group is bonded to the remainder of the molecule through the nitrogen atom.

The term "aminoalkyl" refers to an alkyl group as defined herein, further substituted with at least one amine. Preferred aminoalkyl groups are C$_1$-C$_{10}$aminoalkyl groups. Examples of aminoalkyl groups include, but are not limited to, mono- or di-amino methyl, 1-amino ethyl, 1,1-diamino ethyl, 1,2-diamino ethyl and —C(NH)(NH$_2$). The group is bonded to the remainder of the molecule through an alkyl carbon atom.

The term "amidoalkyl" refers to an alkyl group as defined herein, further substituted with at least one amide group, i.e. a group of the formula alkyl-C(O)NH$_2$. Preferred amidoalkyl groups are C$_2$-C$_{10}$amidoalkyl groups. The group is bonded to the remainder of the molecule through an alkyl carbon atom.

"Aryl" as a group or part of a group denotes an optionally substituted monocyclic, or fused polycyclic, aromatic carbocyclic (ring structure having ring atoms that are all carbon) preferably having from 5 to 12 atoms per ring. Examples of aryl groups include monocyclic groups such as phenyl, fused polycyclic groups such as naphthyl, and the like. Typically an aryl group is a C$_6$-C$_{10}$aryl group.

The term "fused" when used with reference to bicyclic or polycyclic groups refers to bicyclic or polycyclic ring systems in which at least two of the rings share a common C—C bond such as ortho- or peri-fused bicyclic or polycyclic ring systems. The term "fused" also includes bicyclic or polycyclic ring systems that share only one common C atom such as bicyclic and polycyclic spiro ring systems.

The term "arylamine" refers to an amine further bound to an aryl group as defined herein and includes both mono- and di-arylamines, unless specified. The aryl group is preferably a $C_6$-$C_{10}$aryl group. The group is bonded to the remainder of the molecule through the nitrogen atom.

The term "aminoaryl" refers to an aryl group as defined herein, further substituted with at least one amine. Preferred aminoaryl groups are $C_6$-$C_{10}$aminoaryl groups. The group is bonded to the remainder of the molecule via an aryl carbon atom.

The term "alkoxy" as a group or part of a group refers to an alkyl-O— group in which alkyl is as defined herein. Preferably the alkoxy is a $C_1$-$C_{10}$alkoxy. Examples include, but are not limited to, methoxy and ethoxy.

The term "cycle" or "cyclic group" refers to a saturated, partially unsaturated or fully unsaturated monocyclic or fused or spiro polycyclic, ring systems preferably containing from 3 to 10 carbons per ring.

The term "halo" used herein refers to fluoro, chloro, bromo or iodo.

The term "hydroxyalkyl" refers to an alkyl group as defined herein, further substituted with at least one —OH group. Preferred hydroxyalkyl groups are $C_2$-$C_{10}$hydroxyalkyl groups. The group is bonded to the remainder of the molecule through an alkyl carbon atom.

The term "heterocycle" or "heterocyclic group" refers to saturated, partially unsaturated or fully unsaturated monocyclic, bicyclic or fined polycyclic or spiro polycyclic ring systems containing at least one heteroatom selected from the group consisting of nitrogen, sulfur and oxygen as a ring atom. Each ring is preferably from 3 to 10 membered, more preferably 4 to 7 membered. Examples of suitable heterocyclic substituents include, but are not limited to, pyrrole, furan, benzofuran, benzothiazole, imidazole, benzimidazole, imidazoline, pyrazole, pyrazoline, triazole, oxazole, oxazoline, isoxazole, isoxazoline, furazan, oxadiazole, piperidine, pyridine, pyrimidine, pyridazine and pyrazine, each of which may be further substituted with 1 to 3 substituents.

In some preferred embodiments of the invention, and with reference to the general formula (I), one or more of the following definitions apply;

a) $R^1$ is selected from acyl derivatives of pyrrole, pyridine, pyrazine, furan, benzofuran, benzothiazole, imidazole, imidazoline, pyrazole, pyrazoline, triazole, oxazole, oxazoline, isoxazole, isoxazoline, furazan, or oxadiazole, each of which may be further optionally substituted with one or more substituents selected from alkyl, alkoxy, amine, aminoalkyl, amidoalkyl, halo, hydroxy, trihaloalkyl, trihaloalkoxy or phenyl, wherein the phenyl group may be further optionally substituted with 1 to 3 substituents selected from alkyl, alkoxy, hydroxy, halo; nitro, trihaloalkyl, or trihaloalkoxy.

b) $R^1$ is selected from acyl derivatives of furan, imidazole, pyrazole, pyrazine, pyrazole, triazole, oxazole or isoxazole, each of which may be further substituted with 1 to 3 substituents selected from alkyl, alkoxy, amine, aminoalkyl, amidoalkyl, halo, hydroxy, trihaloalkyl, trihaloalkoxy or phenyl wherein the phenyl group may be further optionally substituted with 1 to 3 substituents selected from alkyl, alkoxy, hydroxy, halo, nitro, trihaloalkyl or trihaloalkoxy.

c) $R^1$ is isoxazolecarbonyl optionally substituted with a group selected from alkyl, alkoxy, amine, aminoalkyl, amidoalkyl, halo, hydroxy, trihaloalkyl, trihaloalkoxy or phenyl, wherein the phenyl group may be further optionally substituted with 1 to 3 substituents selected from alkyl, alkoxy, hydroxy, halo, nitro, trihaloalkyl or trihaloalkoxy.

d) $R^1$, together with the carbon atom to which it is attached, forms mono- or bicyclic-nitrogen containing heterocycle, optionally substituted with alkyl.

e) $R^2$ is an aromatic or aliphatic $C_3$-$C_8$cyclic group or $C_3$-$C_8$heterocyclic group comprising 1 to 3 heteroatoms selected from N and O, wherein the $C_3$-$C_8$cyclic group or $C_3$-$C_8$heterocyclic group may be further substituted with one or more substituents selected from alkyl, amine, hydroxy, or the cyclic group or heterocyclic group is fused with an optionally substituted aromatic or aliphatic $C_3$-$C_8$cyclic group or $C_3$-$C_8$heterocyclic group.

f) $R^2$ is selected from cyclohexane or phenyl optionally substituted with one or more substituents selected from alkyl, amine, hydroxy, or the cyclic group or heterocyclic group is fused with an optionally substituted aromatic or aliphatic $C_3$-$C_8$cyclic group or $C_3$-$C_8$heterocyclic group.

g) $R^2$ is selected from cyclohexane, phenyl, (p-methyl)phenyl, (p-amino)phenyl, (p-hydroxy)phenyl or indole.

h) $R^3$ is selected from hydrogen or methyl.

i) $R^4$ is hydrogen, $C_1$-$C_6$alkyl, aminoalkyl or amidoalkyl; $R^5$ is a benzyl group, optionally substituted with a group selected from alkyl, aminoalkyl, alkoxy, $C_4$-$C_7$heterocycle, hydroxy, halo, nitro, dioxalane, trihaloalkyl, trihaloalkoxy or —C(O)NHCHR$^9$R$^{10}$, wherein R$^9$ is —C(O)NH$_2$ and R$^{10}$ is a $C_2$-$C_5$aminoalkyl.

j) $R^4$ is hydrogen, $C_1$-$C_6$alkyl, aminoalkyl or amidoalkyl; $R^5$ is a benzyl group, optionally substituted with a group selected from alkyl, aminoalkyl, alkoxy, arylamine, $C_4$-$C_7$heterocycle, hydroxy, halo, nitro, dioxalane, trihaloalkyl or trihaloalkoxy.

k) $R^4$ is hydrogen; $R^5$ is a benzyl group, substituted with alkyl or alkoxy.

l) $R^4$ is hydrogen; $R^5$ is a benzyl group, substituted with —C(O)NHCHR$^9$R$^{10}$; wherein R$^9$ is —C(O)NH$_2$, and R$^{10}$ is a $C_2$-$C_5$aminoalkyl.

m) $R^4$ is hydrogen; $R^5$ is a benzyl group, substituted with a group selected from alkyl or alkoxy and the group —C(O)NHCHR$^9$R$^{10}$ wherein R$^9$ is —C(O)NH$_2$ and R$^{10}$ is a $C_2$-$C_5$ aminoalkyl.

n) $R^4$ and $R^5$ combined, together with the nitrogen to which they are attached, form piperidine optionally substituted with a group selected from phenyl, benzyl, aminoalkyl, aminoaryl, amidoalkyl or heterocycle or piperidine is fused with an aromatic or aliphatic $C_3$-$C_8$cyclic group or $C_3$-$C_8$heterocyclic group; wherein the phenyl, benzyl, aminoaryl, heterocycle or fused, aromatic or aliphatic $C_3$-$C_8$cyclic group or $C_3$-$C_8$heterocyclic group may be further substituted with 1 to 3 substituents selected from alkyl, alkylamine, alkylamide, alkylsulfonyl, alkoxy, aminoalkyl, aminoacyl, amidoalkyl, arylamine, hydroxy, halo, nitro, oxo, optionally substituted phenyl, optionally substituted piperidine, dioxalane, trihaloalkyl, or trihaloalkoxy or the fused aromatic or aliphatic $C_3$-$C_8$cyclic group or $C_3$-$C_8$heterocyclic group is fused with an, additional $C_6$-$C_{10}$cyclic or $C_6$-$C_{10}$heterocyclic group.

o) $R^6$ is hydrogen or $C_1$-$C_6$alkyl.

p) $R^7$ is $C_1$-$C_6$alkyl, amino, hydroxy, alkoxy, aminoalkyl, amidoalkyl, saturated or unsaturated cycloalkyl, or heterocycle.

q) $R^6$ and $R^7$ combined, together with the carbon to which they are attached, form $C_5$-$C_8$ cyclic group, phenyl or $C_5$-$C_8$ heterocyclic group, optionally substituted with a group selected from alkyl, aminoalkyl, alkoxy, hydroxy, halo, nitro, trihaloalkyl Or trihaloalkoxy.

In a further embodiment with reference to the general formula (I), one or more of the following definitions apply:

r) $R^1$ is selected from acyl derivatives of pyrrole, pyridine, pyrazine, furan, benzofuran, benzothiazole, imidazole, imidazoline, pyrazole, pyrazoline, triazole, oxazole, oxazoline, isoxazole, isoxazoline, furazan, or oxadiazole, each of which may be further optionally substituted with 1 to 3 substituents selected from alkyl or phenyl, wherein the phenyl group may be further optionally substituted with 1 to 3 substituents selected from alkyl, alkoxy, hydroxy, halo, nitro, trihaloalkyl, or trihaloalkoxy.

s) $R^1$ is selected from acyl derivatives of furan, imidazole, pyrazine, pyrazole, triazole, oxazole or isoxazole, each of which may be further substituted with 1 to 3 substituents selected from alkyl or phenyl wherein the phenyl group may be further optionally substituted with 1 to 3 substituents selected from alkyl, alkoxy, hydroxy, halo, nitro, trihaloalkyl or trihaloalkoxy.

t) $R^1$ is isoxazolecarbonyl optionally substituted with a group selected from alkyl or phenyl, wherein the phenyl group may be further optionally substituted with 1 to 3 substituents selected from alkyl, alkoxy, hydroxy, halo, nitro, trihaloalkyl or trihaloalkoxy.

u) $R^2$ is cyclohexane.

v) $R^3$ is hydrogen.

w) $R^4$ is hydrogen, $C_1$-$C_6$alkyl, aminoalkyl or amidoalkyl; $R^5$ is a benzyl group, optionally substituted with a group selected from alkyl, alkoxy, arylamine, $C_4$-$C_7$heterocycle, hydroxy, halo, nitro, dioxalane, trihaloalkyl, trihaloalkoxy or —C(O)NHCHR$^9$R$^{10}$, wherein R$^9$ is —C(O)NH$_2$ and R$^{10}$ is a $C_2$-$C_5$aminoalkyl.

x) $R^4$ is hydrogen, $C_1$-$C_6$alkyl, aminoalkyl or amidoalkyl; $R^5$ is a benzyl group, optionally substituted with a group selected from alkyl, aminoalkyl, alkoxy, $C_4$-$C_7$heterocycle, hydroxy, halo, nitro, dioxalane, trihaloalkyl or trihaloalkoxy.

y) $R^4$ is hydrogen; $R^5$ is a benzyl group, substituted with alkyl or alkoxy.

z) $R^4$ is hydrogen; $R^5$ is a benzyl group, substituted with —C(O)NHCHR$^9$R$^{10}$; wherein R$^9$ is —C(O)NH$_2$ and R$^{10}$ is a $C_2$-$C_5$aminoalkyl.

aa) $R^4$ is hydrogen; $R^5$ is a benzyl group, substituted with a group selected from alkyl or alkoxy and the group —C(O)NHCHR$^5$R$^6$ wherein R$^5$ is —C(O)NH$_2$ and R$^6$ is a $C_2$-$C_5$aminoalkyl.

ab) $R^4$ and $R^5$ combined, together with the nitrogen to which they are attached, form piperidine, optionally substituted with a group selected from phenyl, benzyl, aminoalkyl, amidoalkyl or a heterocycle; wherein the phenyl, benzyl or heterocycle may be further optionally substituted with 1 to 3 substituents selected from alkyl, alkoxy, aminoalkyl, amidoalkyl, hydroxy, halo, nitro, dioxalane, trihaloalkyl or trihaloalkoxy.

ac) $R^6$ is methyl.

ad) $R^7$ is ethyl.

In a further aspect, the present invention provides compounds of the formula (I) represented by the formula (Ia):

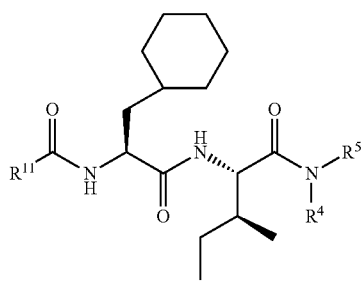

(Ia)

wherein $R^4$ is hydrogen, $C_1$-$C_6$alkyl, aminoalkyl or amidoalkyl;

$R^5$ is a benzyl group, optionally substituted with a group selected from alkyl, aminoalkyl, alkoxy, $C_4$-$C_7$heterocycle, hydroxy, halo, nitro, dioxalane, trihaloalkyl, trihaloalkoxy or —C(O)NHCHR$^9$R$^{10}$; wherein R$^9$ is —C(O)NH$_2$ and R$^{10}$ is a $C_2$-$C_5$aminoalkyl; or $R^4$ and $R^5$ combined, together with the nitrogen to which they are attached, form piperidine, optionally substituted with a group selected from phenyl, benzyl, aminoalkyl, aminoaryl, amidoalkyl or a heterocycle, or piperidine is fused with an aromatic or aliphatic $C_3$-$C_8$cyclic group or $C_3$-$C_8$heterocyclic group; wherein the phenyl, benzyl, heterocycle or fused aromatic or aliphatic $C_3$-$C_8$cyclic group or $C_3$-$C_8$heterocyclic group may be further substituted with 1 to 3 substituents selected from alkyl, alkywherein wherein $R^{11}$ is a 5- or 6-membered unsaturated heterocyclic ring comprising 1 to 3 heteroatoms selected from N and O, optionally substituted with one or more groups selected from alkyl, amino, or phenyl, wherein the phenyl group may be further optionally substituted with 1 to 3 substituents selected from alkyl, alkoxy, hydroxy, halo, nitro, trihaloalkyl or trihaloalkoxy;

$R^4$ is hydrogen, $C_1$-$C_6$alkyl, aminoalkyl or amidoalkyl;

$R^5$ is a benzyl group substituted with a group selected from alkyl, aminoalkyl, alkoxy, $C_4$-$C_7$heterocycle, hydroxy, halo, nitro, dioxalane, trihaloalkyl or trihaloalkoxy; or $R^4$ and $R^5$ combined, together with the nitrogen to which they are attached, form piperidine, optionally substituted with a group selected from phenyl, benzyl, aminoalkyl, aminoaryl, amidoalkyl or a heterocycle, or piperidine is fused with an aromatic or aliphatic $C_3$-$C_8$cyclic group or $C_3$-$C_8$heterocyclic group; wherein the phenyl, benzyl, aminoaryl, heterocycle or fused aromatic or aliphatic $C_3$-$C_8$cyclic group or $C_3$-$C_8$heterocyclic group may be further substituted with 1 to 3 substituents selected from alkyl, alkylamine, alkylamide, alkylsulfonyl, alkoxy, aminoalkyl, aminoaryl, amidoalkyl, arylamine, hydroxy, halo, nitro, oxo, optionally substituted phenyl, optionally substituted piperidine, dioxalane, trihaloalkyl, or trihaloalkoxy; or the fused aromatic or aliphatic $C_3$-$C_8$cyclic group or $C_3$-$C_8$heterocyclic group is fused with an additional $C_6$-$C_{10}$cyclic or $C_6$-$C_{10}$heterocyclic group; and salts thereof.

In a preferred embodiment $R^{11}$ is isoxazole.

Accordingly, in a preferred aspect, the present invention provides compounds of the formula (I) represented by the formula (Ib):

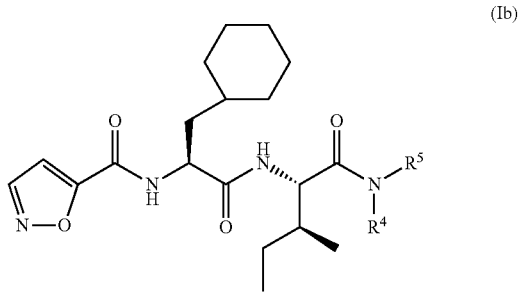

(Ib)

wherein $R^4$ is hydrogen, $C_1$-$C_6$alkyl, aminoalkyl or amidoalkyl;

$R^5$ is a benzyl group, optionally substituted with a group selected from alkyl, aminoalkyl, alkoxy, $C_4$-$C_7$heterocycle, hydroxy, halo, nitro, dioxalane, trihaloalkyl, trihaloalkoxy or —C(O)NHCHR$^9$R$^{10}$; wherein R$^9$ is —C(O)NH$_2$ and R$^{10}$ is a $C_2$-$C_5$aminoalkyl; or $R^4$ and $R^5$ combined, together with the nitrogen to which they are attached, form piperidine, optionally substituted with a group selected from phenyl, benzyl, aminoalkyl, aminoaryl, amidoalkyl or a heterocycle, or piperidine is fused with an aromatic or aliphatic $C_3$-$C_8$cyclic group or $C_3$-$C_8$heterocyclic group; wherein the phenyl, benzyl, heterocycle or fused aromatic or aliphatic $C_3$-$C_8$cyclic group or $C_3$-$C_8$heterocyclic group may be further substituted with 1 to 3 substituents selected from alkyl, alkylamine, alkylamide, alkyloxy, aminoalkyl, amidoalkyl, hydroxy, halo, nitro, dioxalane, trihaloalkyl, or trihaloalkyloxy; and salts thereof.

In a further preferred embodiment and with reference to compounds of the formula (I), $R^{11}$ is isoxazole, $R^4$ is hydrogen and $R^5$ is an optionally substituted benzyl group.

Accordingly, in a further aspect, the present invention provides compounds according to the formula (I) represented by the formula (Ic):

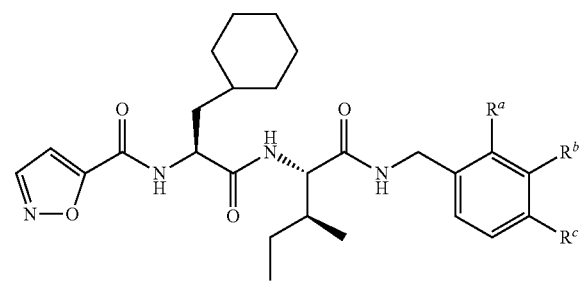

(Ic)

wherein $R^a$, $R^b$ and $R^c$ individually represent a group selected from hydrogen, alkyl, aminoalkyl, alkoxy, $C_4$-$C_7$heterocycle, hydroxy, halo, nitro, trihaloalkyl, trihaloalkoxy or —C(O)NHCHR$^9$R$^{10}$; wherein R$^9$ is —C(O)NH$_2$ and R$^{10}$ is a $C_2$-$C_5$aminoalkyl; or $R^a$ and $R^b$ or $R^b$ and $R^c$ combined form dioxalane; and salts thereof.

In a preferred embodiment with respect to formula (Ic), $R^a$ and $R^c$ are hydrogen and $R^b$ is C(O)NHCHR$^9$R$^{10}$ wherein R$^9$ is —C(O)NH$_2$ and R$^{10}$ is a $C_2$-$C_5$aminoalkyl.

In another preferred embodiment with respect to formula (Ic), one of $R^a$ or $R^b$ is methyl, methoxy or ethoxy, and the other is hydrogen and $R^c$ is hydrogen.

In a further preferred embodiment with respect to formula (Ic), $R^a$ and $R^b$ or $R^b$ and $R^c$ combined form dioxalane, and the remaining $R^c$ or $R^a$ is hydrogen.

In another further preferred embodiment and with reference to compounds of the formula (I), $R^{11}$ is isoxazole and $R^4$ and $R^5$ combined, together with the nitrogen to which they are attached form piperidine, optionally substituted with a group selected from phenyl, benzyl, aminoalkyl, amidoalkyl, aminoaryl or a heterocycle; wherein the phenyl, benzyl or heterocycle may be further substituted with 1 to 3 substituents selected from alkyl, alkoxy, aminoalkyl, amidoalkyl, hydroxy, halo, nitro, dioxalane, trihaloalkyl, or trihaloalkoxy.

Accordingly, in another aspect, the present invention provides compounds according to the formula (I), represented by the formula (Id):

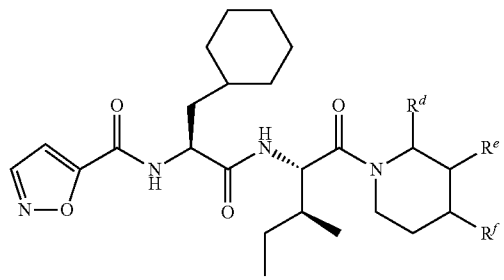

(Id)

wherein $R^d$, $R^e$ and $R^f$ independently represent a group selected from phenyl, benzyl, aminoalkyl, amidoalkyl, aminoaryl or a heterocycle, or $R^d$ and $R^e$ or $R^e$ and $R^f$ combined, form a fused aromatic or aliphatic $C_3$-$C_8$cyclic group or $C_3$-$C_8$heterocyclic group; wherein the phenyl, benzyl, heterocycle or fused aromatic or aliphatic $C_3$-$C_8$cyclic group or $C_3$-$C_8$heterocyclic group may be further substituted with 1 to 3 substituents selected from alkyl, alkoxy, aminoalkyl, amidoalkyl, hydroxy, halo, nitro, dioxalane, trihaloalkyl, or trihaloalkoxy; and salts thereof.

In yet further preferred embodiments, compounds of the formula (I) are selected from the group consisting of:

5-isoxazoyl-Cha-Ile-aminomethylphenyl;
5-isoxazoyl-Cha-Ile-aminomethyl-(4-methoxy)phenyl;
5-isoxazoyl-Cha-Ile-aminomethyl-(2-chloro)phenyl;
5-isoxazoyl-Cha-Ile-aminomethyl-(2-nitro)phenyl;
5-isoxazoyl-Cha-Ile-aminomethyl-(2-fluoro)phenyl;
5-isoxazoyl-Cha-Ile-aminomethyl-(3-fluoro)phenyl;
5-isoxazoyl-Cha-Ile-aminomethyl-(4-fluoro)phenyl;
5-isoxazoyl-Cha-Ile-(3-[aminomethyl]phenyl)-amino-4-aminobutane-1-carboxamide;
5-isoxazoyl-Cha-Ile-(3-[aminomethyl]phenyl)-amino-3-aminopropane-1-carboxamide; or
5-isoxazoyl-Cha-Ile-4-(p-fluorophenyl)piperazine.
5-isoxazoyl-Cha-Ile-(6,7-dimethoxy-1,2,3,4-tetrahydroisoquinoline);
5-isoxazoyl-Cha-Ile-{1-(methylsulfonyl)spiro[indoline-3,4'-piperidine]};
5-isoxazoyl-Cha-Ile-{3H-3-oxo-spiro[isobenzofuran-1,4'-piperidine]};
5-isoxazoyl-Cha-Ile-(4-oxo-spiro[chroman-2,4'-piperidine]);

In other preferred embodiments, PAR2 antagonists represented by compounds of the formula (I) are selected from the group consisting of 5-isoxazoyl-Cha-Ile-aminomethyl-(2-methoxy)phenyl;
5-isoxazoyl-Cha-Ile-aminomethyl-(3-methoxy)phenyl;
5-isoxazoyl-Cha-Ile-aminomethyl-(2-methyl)phenyl;
5-isoxazoyl-Cha-Ile-aminomethyl-(2-ethoxy)phenyl;
5-isoxazoyl-Cha-Ile-aminomethyl-(2-propoxy)phenyl;
5-isoxazoyl-Cha-Ile-aminomethyl-(2-isopropoxy)phenyl;
5-isoxazoyl-Cha-Ile-aminomethyl-(2-butoxy)phenyl;
5-isoxazoyl-Cha-Ile-aminomethyl-(2-isobutoxy)phenyl;
5-isoxazoyl-Cha-Ile-aminomethyl-(2-trifluoromethyl)phenyl;
5-isoxazoyl-Cha-Ile-aminomethyl-(3-trifluoromethoxy)phenyl;
5-isoxazoyl-Cha-Ile-aminomethyl-(2-trifluoromethyl)phenyl;
5-isoxazoyl-Cha-Ile-aminomethyl-(1,3dioxalane)phenyl;
5-isoxazoyl-Cha-Ile-aminomethyl-(3,4-dichloro)phenyl;

5-isoxazoyl-Cha-Ile-aminomethyl-(2,4-dimethoxy)phenyl;
5-isoxazoyl-Cha-Ile-aminomethyl-(2,5-dimethoxy)phenyl;
5-isoxazoyl-Cha-Ile-aminomethyl-(3,4-dimethoxy)phenyl;
5-isoxazoyl-Cha-Ile-aminomethyl-(2,3-dimethoxy)phenyl;
5-isoxazoyl-Cha-Ile-aminomethyl-(2,3,4-dimethoxy)phenyl;
5-isoxazoyl-Cha-Ile-aminomethyl-(2,6-dimethoxy)phenyl;
5-isoxazoyl-Cha-Ile-aminomethyl-(2-methoxy-5-trifluoromethoxy)phenyl;
5-isoxazoyl-Cha-Ile-aminomethyl-(2,4-dimethoxy)phenyl;
5-isoxazoyl-Cha-Ile-aminomethyl-(3,5-bis(trifluoromethyl))phenyl;
5-isoxazoyl-Cha-Ile-(4-phenyl)piperidine;
5-isoxazoyl-Cha-Ile-4-(p-methoxy)phenyl piperidine;
5-isoxazoyl-Cha-Ile-4-(p-chloro)phenyl piperidine;
5-isoxazoyl-Cha-Ile-4-(o-trifluoromethyl)phenyl piperidine;
5-isoxazoyl-Cha-Ile-4-(o-phenyl)phenyl piperidine;
5-isoxazoyl-Cha-Ile-4-(m-phenyl)phenyl piperidine;
5-isoxazoyl-Cha-Ile-4-(p-phenyl)phenyl piperidine;
5-isoxazoyl-Cha-Ile-4-(p-phenoxy)phenyl piperidine;
5-isoxazoyl-Cha-Ile-4-(2,5-dimethoxy)phenyl piperidine;
5-isoxazoyl-Cha-Ile-(4-benzyl)piperidine;
5-isoxazoyl-Cha-Ile-2S-(tert-butylamide)piperidine;
5-isoxazoyl-Cha-Ile-4-(4-acetamide)phenyl piperidine;
5-isoxazoyl-Cha-Ile-3-(o-fluoro)aminophenyl piperidine;
5-isoxazoyl-Cha-Ile-3-(m-fluoro)aminophenyl piperidine;
5-isoxazoyl-Cha-Ile-3-(p-fluoro)aminophenyl piperidine;
5-isoxazoyl-Cha-Ile-3-(o-trifluoromethyl)aminophenyl piperidine;
5-isoxazoyl-Cha-Ile-3-(m-trifluoromethyl)aminophenyl piperidine;
5-isoxazoyl-Cha-Ile-3-(p-trifluoromethyl)aminophenyl piperidine;
5-isoxazoyl-Cha-Ile-spirochroman-2,4'-piperidine;
5-isoxazoyl-Cha-Ile-[(S)—N-(tert-butyl)]piperidine;
5-isoxazoyl-Cha-Ile-aminodimethyl-(2-methoxy)phenyl;

In still further preferred embodiments, PAR2 antagonists represented by compounds of the formula (I) are selected from the group consisting of
5-isoxazoyl-Cha-Ile-aminomethyl-benzimidazole;
5-isoxazoyl-Cha-Ile-aminomethyl-2-biphenyl;
5-isoxazoyl-Cha-Ile-aminomethyl-3-biphenyl;
5-isoxazoyl-Cha-Ile-aminomethyl-4-biphenyl;
5-isoxazoyl-Cha-Ile-aminomethyl-2-napthalene;
5-isoxazoyl-Cha-Thr(Me)-aminomethyl-(2-methoxy)phenyl;
Cha-Ile-spiro[indene-1,4'-piperidine];
5-isoxazoyl-Cha-Thr(Me)-spiro[indene-1,4'-piperidine];
5-(3-amino-isoxazoyl)-Cha-Ile-spiro[indene-1,4'-piperidine];
5-isoxazoyl-Cha-Thr(Me)-spiro[indene-1,4'-piperidine];
5-isoxazoyl-Cha-Ile-spiro[chroman-2,4'-piperidine];
5-isoxazoyl-Cha-Ile-spiro[indene-1,4'-piperidine];
5-isoxazoyl-Cha-Ile-spiro[indane-1,4'-piperidine];
5-isoxazoyl-Cha-Ile-spiro[octahydro-1H-indene-1,4'-piperidine]; or
5-isoxazoyl-Cha-Ile-(4-oxo-spiro[chroman-2,4'-piperidine]).

It will be appreciated that compounds of the formula (I) possess at least two asymmetric centres and are therefore capable of existing in more than one stereoisomeric form. It is highly desirable that compounds of the present invention exist as single diastereomers wherein the asymmetric carbon atoms of the cyclohexylalanine and isoleucine residues are of the L-configuration. The invention thus also relates to compounds in substantially pure stereoisomeric form with respect to at least the two asymmetric centres of the cyclohexylalanine and isoleucine residues, e.g., greater than about 90% de, such as about 95% to 97% de or greater than 99% de, as well as mixtures, including racemic mixtures, thereof. Such diastereomers may be prepared by asymmetric synthesis, for example using chiral intermediates, or mixtures may be resolved by conventional methods, e.g. chromatography, or use of a resolving agent.

Additionally, formula (I) is intended to cover, where applicable, solvated as well as unsolvated forms of the compounds. Thus, each formula includes compounds having the indicated structure, including the hydrated as well as the non-hydrated forms.

It will be appreciated that the compounds of the invention may exist as salts. The novel bioactive compounds of the invention can be administered to a subject as a pharmaceutically acceptable salt. It will be appreciated however that non-pharmaceutically acceptable salts also fall within the scope of the present invention since these may be useful as intermediates in the preparation of pharmaceutically acceptable salts or as tools for biological studies.

The term "pharmaceutically acceptable" as applied to salts of the present invention and/or used in methods of the present invention refers to salts which are, within the scope of sound medical judgment, suitable for use in contact with the tissues of humans and lower animals without undue toxicity, irritation, allergic, or a like negative response that exceeds a reasonable risk/therapeutic benefit ratio. Preferably, a pharmaceutically acceptable salt is a salt that is suitable for administration to a patient. Accordingly, the present invention also extends to a pharmaceutically acceptable salt of any one of the compounds of the present invention.

Pharmaceutically acceptable salts are generally known in the art, and in the case of the present invention, include relatively non-toxic, organic or inorganic salts of the compounds of the present invention. Examples of such salts include, but are not limited to, acid addition salts' such as hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naphthylate salts, mesylate salts, tosylate salts, citrate salts, lactate salts, maleate salts, succinate salts, tartrate salts, fumarate salts, and the like (see, for example, Berge et al. *J. Pharm. Sci.* 1977, 66, 1-19). In addition, pharmaceutically acceptable salts also include basic salts such as alkali metal salts, alkaline earth salts, and ammonium salts. For example, pharmaceutically acceptable basic salts include salts of aluminium, calcium, lithium, magnesium, potassium, sodium, zinc, and the like. In addition, organic salts may also be used including, e.g., salts of lysine, N,N'-dibenzylethylenediamine, chloroprocaine, choline, diethanolamine, ethylenediamine, meglumine (N-methylglucamine), procaine and tris. The basic nitrogen-containing groups in the compounds of the present invention can be quaternized with various organic agents including, e.g., alkyl halides (such as lower alkyl halide including methyl, ethyl, propyl, and butyl chlorides, bromides and iodides), long chain halides (e.g., decyl, lauryl, myristyl and stearyl chlorides, bromides and iodides), aralkyl halides (e.g., benzyl and phenethyl bromides), dialkyl sulfates (e.g., dimethyl, diethyl, dibutyl and diamyl sulfates).

The salts of the compounds of the present invention also can exist in the form of solvates, e.g., with water, methanol, ethanol, dimethylformamide, ethyl acetate, and the like, and mixtures thereof.

Prodrug derivatives are also included in the scope of the present invention, and in the broadest sense, encompass compounds that are converted in vivo to a compound of the present invention. Such derivatives would readily occur to one skilled in the art and include compounds that are further modified with, for example, alkyl or acyl groups, oxides, sugars or oligopeptides, which are rapidly cleaved in the body to give the active compounds according to the invention. That is, the term "prodrug" refers to a precursor or modified compound of the present invention that is not fully active or available until converted in vivo to its therapeutically active or available form.

Processes for preparing the compounds of the present invention are provided as further embodiments of the invention and are illustrated by the following general procedures.

Compounds may be synthesized using protected amino acids. Amino protecting groups are generally known to those skilled in the art and relate to groups which are suitable for protecting (or blocking) an amino group from chemical reactions, but which are easily removable after the desired chemical reaction has been carried out at other positions in the molecule. Since the protective groups are removed after the desired reaction (or reaction sequence), their nature and size is otherwise uncritical. Examples of amino protecting groups include, but are not limited to acyl protecting groups such as acetyl, propionyl, butyryl, phenylacetyl, benzoyl or toluoyl groups; aryloxy-alkanoyl protecting groups; alkoxycarbonyl protecting groups such as methoxycarbonyl, ethoxycarbonyl, 2,2,2-trichloroethoxycarbonyl, tert-butyldicarbonyl (Boc), 2-iodoethoxycarbonyl; aralkoxycarbonyl protecting groups such as carbobenzyloxy (Cbz), 4-methoxy-benzyloxycarbonyl, fluorenylmethyloxycarbonyl chloride (Fmoc); or arylsulfonyl protecting groups such as 4-methoxy-2,3,6-trimethylphenylsulfonyl (Mtr), pentamethyl-2,3-dihydrobenzofuran-5-sulfonyl (Pbf) or 2,2,5,7,8-pentamethylchroman-6-sulfonyl (Pmc). Preferred amino protecting groups are Boa, Cbz, Fmoc, and benzyl. The more preferred amino acid protecting group is Boc.

Generally, compounds are synthesised in solution phase wherein the Doc-protected isoleucine residue, one or more coupling or activating reagents and a base such as N,N-diisopropylethylamine (DIPEA) are dissolved in a suitable volume of solvent.

Coupling reagents used to activate a carboxyl group in order to progress the coupling of the carboxyl group to an amino group are generally well known to those skilled in the art and may include carbodiimide coupling reagents such as dicyclohexylcarbodiimide (DCC) and diisopropylcarbodiimide (DIC) as well as triazole coupling reagents such as 1-hydroxy-benzotriazole (HOBt), 1-hydroxy-7-aza-benzotriazole (HOAt), benzotriazole-1-yl-oxy-tris-(dimethylamino)-phosphonium hexafluorophosphate (BOP), benzotriazol-1-yl-oxytripyrrolidinophosphonium hexafluorophosphate (PyBOP), 2-(1H-7-azabenzotriazol-1-yl)1,1,3,3-tetramethyluronium hexafluorophosphate methanaminium (HBTU), 2-(1H-benzotriazol-1-yl)1,1,3,3-tetramethyluronium hexafluorophosphate (HBTU) and O-(1H-6-chlorobenzotriazole-1-yl)1,1,3,3-tetramethyluronium hexafluorophosphate (HCTU).

Generally, the above reaction may be performed in any solvent or mixture of solvents suitable for solution phase peptide synthesis including, but not limited to dimethylformamide (DMF), N-methylpyrrolidine (NMP), trifluoroethanol (TFE), hexafluoroisopropanol (HFIP), dichloromethanol (DCM), or chloroform. In a preferred embodiment, the reaction is performed in DMF.

The solution is then added to an amino bearing C-terminal moiety, represented by the substituents $R^2$ and $R^3$ for compounds of the formula (I), and left to stir until the reaction reaches completion. Generally, the reaction is performed at room temperature. Completion of the coupling reaction is determined by electrospray ionisation mass spectroscopy (ESI MS) or other forms of spectrometry.

The intermediate compound is then isolated from the reaction mixture and the crude product is treated with a solution of trifluoroacetic acid (TFA) in DCM to remove the isoleucine N-terminal Boc-protecting group. The solution is then evaporated under $N_2$, washed, filtered and evaporated under reduced pressure. Subsequent amino acids and N-terminal carboxylic acids are then sequentially coupled under the same conditions. The final crude products are purified by reverse phase high performance liquid chromatography (rpHPLC). The compounds of the present invention are characterized by high-resolution mass spectroscopy (HRMS) and proton nuclear magnetic resonance spectroscopy ($^1$H NMR) and purity of the compounds is assessed via analytical reversed phase HPLC.

The compounds of the present invention have been identified by their ability to modulate PAR2 activity, either by activating the receptor or by inhibiting the activity of the native tethered ligand and as such, may be referred to herein as "agonists"; "antagonists", "inhibitors", "PAR2 inhibitors", "inhibitors of PAR2", "biased ligands", and the like. It is important to note that PAR2 antagonists in a particular cell type or assayed in a particular way may be PAR2 agonists or partial agonists in a different cell type or assayed in a different way, and vice versa. For example, compounds that activate the release of intracellular calcium from one type of cell are agonists or partial agonists, while those that inhibit such release may be antagonists. However these "agonist" and "antagonist" effects may be reversed for a given compound or PAR2 ligand in a different cell, or opposite responses may be observed using a different reported assay (e.g. ERK phosphorylation or cAMP stimulation).

The term "PAR2 antagonist" herein refers to a compound that at least inhibits the release of intracellular calcium following exposure of the receptor to the native tethered ligand or to a synthetic PAR2 agonist. Those skilled in the art will be familiar with techniques for determining such compounds, for example, by the use of a cell based in vitro assay such as the assay described in the Examples.

"Antagonists", "inhibitors", "PAR2 inhibitors" or "inhibitors of PAR2" of the present invention are compounds that bind to and inhibit the activation of the PAR2 receptor by native agonists such as the native tethered ligand and include compounds that act as antagonists of the PAR2 receptor as well as reverse agonists of the receptor. Whereas antagonists act by blocking the activation induced by agonist binding at the receptor, inverse agonists also occupy the receptor and function by decreasing the constitutive level of receptor activation in the absence of an agonist. The ability of the compounds of the present invention to inhibit the activation of the PAR2 can be assessed by any number of means available to the skilled addressee, for example, in vitro assays measuring the effect of PAR2 inhibition on a number of downstream markers including intracellular calcium mobilisation, intracellular cyclic adenosine monophosphate (cAMP) stimulation or ERK1/2 phosphorylation, such as those methods described in the Examples.

The term "ligand" refers to a specific binding partner of a receptor and includes, without limitation, the native tethered PAR2 ligand as well as unbound endogenous, extracellular ligands such as receptor agonists; partial agonists, mixed agonists, antagonists and drugs. The term "receptor" refers to a specific binding partner of a ligand and includes, without limitation, membrane bound receptors.

The ability of the compounds of the present invention to modulate PAR2 can be assessed by any number of means available to the skilled addressee, for example, in vitro assays measuring the effect of PAR2 modulation on a number of downstream markers including intracellular calcium mobilisation, intracellular cyclic adenosine monophosphate (cAMP) stimulation or ERK1/2 phosphorylation, such as those methods described in the Examples.

Preferably, and without being limited by theory, the compounds of the present invention inhibit or amplify the activation of PAR2 by binding to the receptor and either preventing the native tethered ligand from contacting the receptor binding region or competing with the tethered ligand or binding elsewhere in the receptor to induce agonist or antagonist activity. Antagonists of PAR2 may also act by inhibiting the activity of other ligands toward PAR2, including, but not limited to, unbound endogenous ligands and synthetic agonists as described herein.

Also preferred for some aspects of the present invention are compounds of the present invention that bind to and activate PAR2 in the absence of activating proteases.

In one aspect of the present invention, there is provided a method of modulating the activity of PAR2, comprising exposing the cell to a compound of formula (I), or a salt thereof. The exposing of the cell to the compound, or a salt thereof, may occur in vitro, ex vivo or in vivo.

Where the exposing of a cell to the compound occurs in vitro or ex vivo, for example, the method of the present invention may be used as a tool for biological studies or as a diagnostic tool to determine the efficacy of certain compounds (alone or in combination) for modulating PAR2 activity in a subject. For example, a cell that expresses PAR2 may be removed from a subject and exposed to one or more compounds of the present invention, or salts thereof. The ability of the compound (or compounds) to modulate the activity of PAR2 can be assessed by measuring any one of a number of down stream markers via a method known to one skilled in the art. Thus, one may be able to ascertain whether a certain compound is more efficacious than another and tailor a specific treatment regime to that subject.

In a preferred embodiment, the exposing of the cell to the compound, or a salt thereof, is in vivo.

In one embodiment of the present invention there is provided a prophylactic or therapeutic method of treating a subject at risk of or susceptible to a disease or disorder, or having a disease or disorder, associated with aberrant PAR2 expression and/or activity. Specific diseases and disorders include, but are not limited to, acute and chronic inflammatory disorders such as arthritis disorders, atherosclerosis, inflammatory bowel diseases, pancreatitis, cardiovascular disease, gastric ulcer, colitis, asthma, fibrosis and fibrotic disorders, vascular inflammation and other conditions associated with inflammatory conditions such as epilepsy, Alzheimer's disease, Parkinson's disease, metabolic syndrome, obesity, type II diabetes, fibrosis and fibrotic conditions, cardiovascular diseases, as well as proliferative disorders such as cancers including but not limited to those of the stomach, colon, bowel, breast, pancreas, brain or liver.

In a preferred embodiment, the prophylactic or therapeutic method comprises the steps of administering a compound according to the present invention, or a pharmaceutically acceptable salt thereof, to a subject who has a disease or disorder, a symptom of disease or disorder, or predisposition toward a disease or disorder associated with undesired or insufficient PAR2 activity as herein described, for the purpose to cure, heal, alleviate, relieve, alter, remedy, ameliorate, improve, or affect the disease or disorder, the symptoms of the disease or disorder, or the predisposition towards the disease or disorder. The prophylactic treatment may reduce the incidence of diseases or disorders associated with undesirable or insufficient PAR2 activity.

In a further preferred embodiment, the present invention provides a method of treating or preventing metabolic syndrome comprising administering to a subject in need thereof an effective amount of a PAR2 antagonist.

"Metabolic syndrome" encompasses but is not limited to, abdominal obesity, adipose inflammation, dyslipidaemia, hyperglycaemia, a prothrombotic state and hypertension increasing an individual's risk of developing type II diabetes mellitus, insulin resistance and cardiovascular diseases (Van Gaal, L. F., et al, *Nature* 2006, 444, 875-80; Reaven, G. M., *Diabetes* 1988, 37, 1595-1607; Dandona, P., et al, *Circulation* 2005, 111, 1448-54; Zimmet, P. Z., et al, *Med J Aust* 2005, 183, 175-6; Ferrannini, E., *Ann Med* 2006, 38, 42-51; Symonds, M. E., et al, *Nat Rev Endocrinol,* 2009). Metabolic syndrome is associated with complications such as, but not limited to, excessive visceral fat deposition, hypertension, impaired glucose and insulin homeostasis, insulin resistance, endothelial damage, cardiovascular hypertrophy, inflammation, vascular inflammation, atherosclerosis, ventricular contractile dysfunction, fibrosis and fatty liver disease (Van Gaal, L. F., et al., *Nature* 2006, 444, 875-80; Zimmer, P. Z., et al., *Med J Aust* 2005, 183, 175-6).

Diets rich in saturated fats and processed sugars force excessive uptake of fatty acids and glucose into adipose tissue, stimulating infiltration of immune cells and activation of inflammatory stress pathways that cause insulin resistance, type II diabetes, hyperlipidemia, hypertension and cardiovascular disease. Inflammatory and metabolic processes are mediated by some proteolytic enzymes that share the common cellular target, PAR2. Without being limited to theory is theorised that obesity correlates in vivo with increased PAR2 expression in adipose tissue, primarily in adipose immune cells such as macrophages. The common dietary fat, palmitic acid, increases PAR2 expression in vitro in human macrophages, amplifying PAR2-induced secretion of proinflammatory cytokines (e.g. IL-1β, IL-6) that can be inhibited by PAR2 antagonists. Therefore, PAR2 expression is a promising new biomarker that correlates with obesity and is stimulated by a dietary fatty acid. PAR2 activation is a substantial contributor to inflammatory/metabolic dysfunction, and PAR2 antagonism is effective in preventing and treating diet-induced obesity as well as inflammatory, metabolic and cardiovascular dysfunction.

Accordingly, in one embodiment, the present invention provides a method of treating or preventing obesity comprising administering to a subject in need thereof an effective amount of a PAR2 antagonist. In another embodiment the present invention provides a method of treating type II diabetes comprising administering to a subject in need thereof an effective amount of a PAR2 antagonist. In a further embodiment the present invention provides a method of treating fibrosis comprising administering to a subject in need thereof an effective amount of a PAR2 antagonist. In yet a further embodiment the present invention provides a method of treating cardiovascular disease comprising administering to a subject in need thereof an effective amount of a PAR2 antagonist. In a further embodiment, the PAR2 antagonist will be a PAR2 antagonist represented by compounds of the formula (I) according to the present invention.

Studies have shown that PAR2 is proinflammatory in a range of diseases. PAR2 is activated by many serine and other proteases including trypsin, mast cell tryptase and tissue factor VILA and it is likely that many serine and other proteases contribute to regulation of adipose tissue macrophages that may be important in weight gain. However, PAR2 is a key cellular target for many such protease enzymes and thus represents a possible therapeutic target for blockade of some effects of multiple activating proteases. Without intending to limit the invention by theory, it is hypothesised that fatty acids that are abundant in western diets such as palmitic acid, may act as endogenous triggers that are primarily responsible for an increase in expression of PAR2 on and in immune cells, such as macrophages, as well as adipocytes and adipose immune cells. It is also proposed that fatty acids and many proteases may also upregulate expression of PAR2. PAR2 is then cleaved by a wide variety of increased circulating proteases, and perhaps as yet unreported endogenous agonists, to induce adipose tissue inflammation and metabolic and cardiovascular dysfunction during diet-induced obesity.

Accordingly, a second hypothesis is that antagonists of PAR2 will be effective in controlling any PAR2-mediated downstream signal transduction in macrophages, other immune cells, adipocytes, pancreatic and liver cells, thereby mitigating the effects of endogenous proteases on metabolic syndrome. Accordingly, it is envisaged that potent and specific PAR2 antagonists might attenuate diet-induced obesity and metabolic syndrome.

The prophylactic or therapeutic methods of the present invention may also comprise the administering of a combination of the compounds according to the present invention, or pharmaceutically acceptable salts thereof, to a subject who has a disease or disorder, a symptom of disease or disorder, or predisposition toward a disease or disorder associated with undesired PAR2 activity as herein described, for the purpose to cure, heal alleviate, relieve, alter, remedy, ameliorate, improve, or affect the disease or disorder, the symptoms of the disease or disorder, or the predisposition towards the disease or disorder. The prophylactic treatment may reduce the incidence of diseases or disorders associated with undesirable PAR2 activity. In some embodiments, combinations of compounds of the present invention or pharmaceutically acceptable salts thereof may provide enhanced inhibition of PAR2 activity in comparison to prophylactic or therapeutic methods that utilise only one of the compounds of the present invention or pharmaceutically acceptable salts thereof.

It would also be appreciated by one skilled in the art that the prophylactic or therapeutic methods as herein described could be used in any number of combinations with other treatment modalities currently employed in the art.

Conditions in which PAR2 expression and/or activity is increased or decreased, and where it is desirable to reduce or increase said activity, may be identified by those skilled in the art by any or a combination of diagnostic or prognostic assays known in the art. For example, a biological sample obtained from a subject (e.g. blood, serum, plasma, urine, saliva, cerebrospinal fluid, adipose tissue, brain tissue and/or cells derived there from) may be analysed for PAR2 expression and/or activity. Such conditions include, but are not limited to, autoimmune or inflammatory disorders such as arthritis, colitis and inflammatory bowel diseases, pancreatitis, diseases of the liver, kidney and genitourinary system, cardiovascular diseases, stroke, gastric ulcer, asthma, fibrosis and fibrotic disorders, other conditions associated with inflammatory conditions such as epilepsy, Alzheimer's disease, Parkinson's disease, obesity and type II diabetes, metabolic disorders, digestive disorders, neurodegenerative and respiratory diseases, diseases of the skin and subcutaneous tissue, diseases of muscles, bones and tendons, as well as proliferative disorders such as cancers including those of the stomach, colon, bowel, breast or pancreas.

It is considered that the above methods are suitable for the prophylactic and therapeutic treatment of any species, including, but not limited to, all mammals including humans, canines, felines, cattle, horses, pigs, sheep, rats and mice, as well as chickens, birds, reptiles and lower organisms such as bacteria.

In another embodiment there is provided the use of a compound of the formula (I) as defined herein for the prophylactic or therapeutic treatment of disease or disorder associated with undesirable PAR2 activity.

In a preferred embodiment, the present invention provides the use of a PAR2 antagonist for the treatment or prevention of a disease or disorder selected from metabolic syndrome, obesity, type II diabetes, fibrosis and cardiovascular disease.

In a further preferred embodiment, the present invention provides the use of the PAR2 antagonist represented by compounds of the formula (I) according to the present invention for the treatment or prevention of a disease or disorder selected from metabolic syndrome, obesity, type II diabetes, fibrosis and cardiovascular disease. The compound of formula (I) may be a compound of formula (I) or (Ia).

In another embodiment, the present invention provides the use of a compound of the formula (I) as defined herein in the manufacture of a medicament for the prophylactic or therapeutic treatment of disease or disorder associated with undesirable PAR2 activity. The compound of formula (I) may be a compound of formula (Ia).

In a preferred embodiment, the present invention provides the use of a PAR2 antagonist in the manufacture of a medicament for the treatment or prevention of a disease or disorder selected from metabolic syndrome, obesity, type II diabetes, fibrosis and cardiovascular disease.

In a further preferred embodiment, the present invention provides the use of a PAR2 antagonist represented by compounds of the formula (I) according to the present invention in the manufacture of a medicament for the treatment or prevention of a disease or disorder selected from metabolic syndrome, obesity, type II diabetes, fibrosis and cardiovascular disease. The compound of formula (I) may be a compound of formula (I) or (Ia).

In another embodiment of the present invention, there is provided a pharmaceutical composition including a compound of the formula (I), or a salt thereof (also referred to herein as an "active compound"). In a preferred embodiment, the pharmaceutical composition may comprise a pharmaceutically acceptable carrier, excipient, diluent and/or adjuvant.

Pharmaceutical compositions of the present invention may be employed alone or in conjunction with other compounds, such as therapeutic compounds.

As used herein, the term "pharmaceutically acceptable carrier" preferably includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is generally formulated to be compatible with its intended route of administration.

Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL.™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, or liquid polyetheylene glycol, and the like), and suitable mixtures thereof. The proper fluidity can be maintained, for example, by the use of a coating such as lecithin, by the maintenance of the required particle size in the case of a dispersion or by the use of surfactants. Prevention of the action of microorganisms can be achieved by incorporation of various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, or sorbitol, or sodium chloride in the composition. Prolonged absorption of the injectable compositions can be brought about by including in the composition an agent which delays absorption, for example, aluminium monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally comprise an inert diluent or an edible carrier. For the purpose of oral therapeutic administration, the active compound can be incorporated with excipients and used in the form of syrups, tablets, troches, or capsules, e.g., gelatin capsules. Oral compositions can also be prepared using a fluid carrier such as olive or other oils, or fluids for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavouring agent such as peppermint, methyl salicylate, or orange flavouring.

For administration by inhalation, the compounds are delivered in the form of an aerosol spray from a pressurised container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished with nasal sprays or suppositories. The compounds can be prepared in the form of suppositories (e.g., with conventional suppository bases such as cocoa butter and other glycerides) or retention enemas for rectal delivery.

For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form" as used herein preferably refers to physically discrete units suited as unitary dosages for the subject to be treated; each unit containing a predetermined quantity of active compound calculated to produce the desired therapeutic effect in association with the required pharmaceutical carrier.

The pharmaceutical compositions according to the present invention can be included in a container, pack, or dispenser together with instructions for administration.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosages for use in humans. The dosage lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The skilled artisan will appreciate that certain factors may influence the dosage and timing required to effectively treat a subject, including the activity of the specific compound employed, the age, body weight, general health, gender, and diet of the subject, the time of administration, the route of administration, the rate of excretion, any drug combination, the degree of expression or activity to be modulated, the severity of the disease or disorder, previous treatments and other diseases present.

For the above mentioned indications, the appropriate dosage will vary depending on, e.g. the compound employed, the age, sex, weight and general physical condition of the subject, the mode of administration, the nature and/or severity of the condition or the desired effect. By balancing these features it is well within the general skill of a medical practitioner to determine appropriate dosages. By way of example, however, suitable daily dosages are in the range of from about 0.1 to about 2000 mg/kg, preferably from about 0.2 to about 100 mg/kg, more preferably from about 0.5 to about 200 mg/kg, even more preferably from about 1 to about 50 mg/kg of body weight.

Examples of the procedures used in the present invention will now be more fully described. It should be understood, however, that the following description is illustrative only and should not be taken in any way as a restriction on the generality of the invention described above.

EXAMPLES

Methods for Preparing Compounds of the General Formula (I)

The following examples are representative of the present invention, and provide detailed methods for preparing exemplary compounds of the present invention.
General Amino Acid Coupling Procedure (A):

Compounds can be synthesized in solution phase using, for example, Fmoc or Boc protected amino acids. In one example, Boo-protected isoleucine (1.2-1.5 eq) was activated with HBTU or BOP (1.5 eq) and DIPEA (1.5 eq) in DMF (0.2-0.5 M) for 10 minutes. The solution was then added to free amine and the mixture was stirred until the reaction reached completion. The reaction mixture was diluted with EtOAc and washed with saturated $NaHCO_3$ (×2). The organic layers were dried over $MgSO_4$, and evaporated in vacuo. The crude was then treated with 20% TFA in DCM and stirred for 1-2 h to remove Boc-protecting group. The TFA was removed by evaporating the reaction mixture under $N_2$. The residue was dissolved in DCM and washed with saturated $NaHCO_3$ (×2), dried with $MgSO_4$, filtered and evaporated in vacuo. The Boc-protected cyclo-hexylalanine amino acid (Boc-Cha-OH) and optionally substituted heterocycle carboxylic acids were then sequentially coupled under the same conditions. Each coupling reaction was monitored by ESI MS, with most reactions reaching completion overnight.
General HPLC Purification and Analysis Methods:

All crude products were purified via semipreparative rpHPLC fitted with a tunable absorbance detector (λ 214 nM), using a Phenomenex C18 column (300 Å, 21.2×250 mm). The purified compounds were characterized by HRMS and $^1$H NMR (400 MHz or 600 MHz), and the purities were assessed via analytical rpHPLC (Phenomenex C18 column, 300, 4.6×250 mm, λ 214, 230 and 254 nm). All compounds were ≥95% pure.

Analytical rpHPLC methods: 50-100% B in 10 min, 100% B for further 10 min

Solvent A: 0.1% TFA in $H_2O$, solvent B: 0.1% TFA in 10% $H_2O$, 90% acetonitrile (for semipreparative and analytical rpHPLC)

High-resolution electrospray ionisation mass spectroscopy (HRMS) measurements were obtained on a Broker micrOTOF mass spectrometer equipped with a Dionex LC system (Chromeleon) in positive ion mode by direct infusion in MeCN at 100 µL/h using sodium formate clusters as an internal calibrant. Data was processed using Broker Daltonics Data Analysis 3.4 software. Mass accuracy was better than 1 ppm error.

Example 1

Preparation of 5-isoxazoyl-Cha-Ile-aminomethyl-(2-fluorophenyl (6)

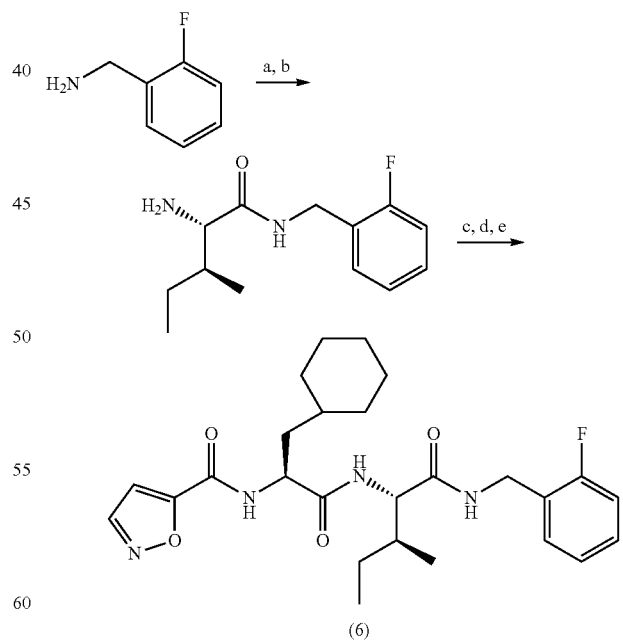

Scheme 1.

(6)
a) Boc-Ile-OH, HBTU/DIPEA in DMF; b) 20% TFA in DCM;
c) Boc-Cha-OH, HBTU/DIPEA in DMF; d) 20% TFA in DCM;
e) Isoxazole 5-carboxylic acid, HBTU/DIPEA in DMF Compound 6 was synthesised by following the general amino acid coupling procedure A.

¹H NMR (400 MHz, CDCl₃): δ 0.79-0.86 (m, 8H), 0.88-0.98 (m, 1H), 1.01-1.23 (m, 5H), 1.27-1.37 (m, 1H), 1.39-1.49 (m, 1H), 1.63-1.77 (H's overlap with H₂O peak), 1.81-1.88 (m, 1H), 4.40-4.45 (dd, 1H, J=5.6, 14.8 Hz), 4.51-4.57 (dd, 1H, J=6.0, 14.8 Hz), 4.70-4.76 (m, 1H), 6.63 (br s, 1H), 6.87-6.89 (br s, 1H), 6.91-6.92 (d, 1H, J=2 Hz), 7.00-7.10 (m, 2H), 7.22-7.36 (m, 3H), 8.30-8.31 (d, 1H, J=1.6 Hz).

HRMS: [MH]⁺ 487.2715 (calc. for $C_{26}H_{36}FN_4O_4^+$) 487.2718 (found).

Example 2

Preparation of 5-isoxazoyl-Cha-Ile-aminomethyl-(2-methoxy)phenyl (18)

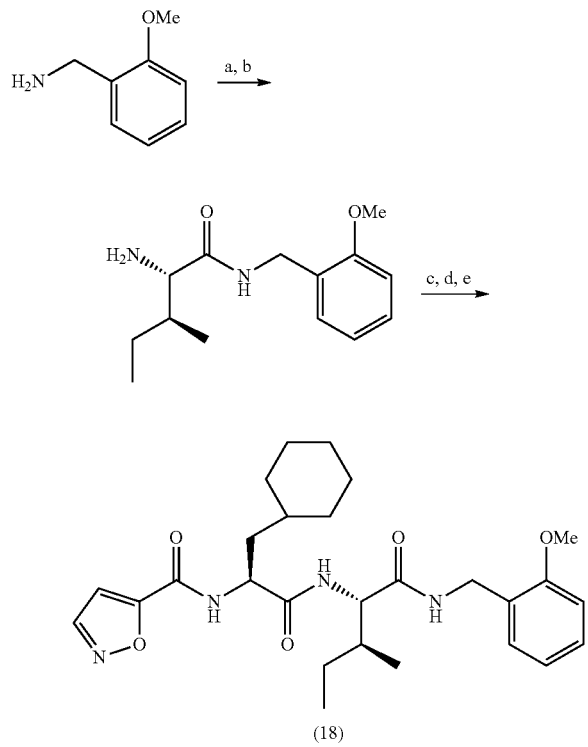

a) Boc-Ile-OH, HBTU/DIPEA in DMF; b) 20% TFA in DCM;
c) Boc-Cha-OH, HBTU/DIPEA in DMF; d) 20% TFA in DCM;
e) Isoxazole 5-carboxylic acid, HBTU/DIPEA in DMF.

Compound 18 was synthesised by following the general amino acid coupling procedure A.

¹H NMR (400 MHz, CDCl₃): δ 0.82-0.86 (m, 7H), 0.88-1.00 (m, 2H), 1.04-1.22 (m, 1H), 1.25-1.37 (m, 2H), 1.40-1.46 (m, 1H), 1.59-1.73 (m, 7H), 1.77-1.84 (m, 2H), 3.86 (s, 3H), 4.19-4.23 (dd, 1H, J=6.8, 8.8 Hz), 4.37-4.42 (dd, 1H, J=6, 14.4 Hz), 4.46-4.51 (dd, 1H, J=6, 14.4 Hz), 4.60-4.65 (m, 1H), 6.19-6.21 (t, 1H, J=5.6 Hz), 6.50-6.53 (d, 1H, J=8.8 Hz), 6.87-6.93 (m, 3H), 6.99-7.01 (d, 1H, J=7.2 Hz), 7.23-7.29 (m, 2H), 8.331-8.335 (d, 1H, J=1.6 Hz).

HRMS: [MH]⁺ 499.2915 (calc. for $C_{27}H_{39}N_4O_5^+$) 499.2915 (found).

Example 3

Preparation of 5-isoxazoyl-Cha-Ile-aminomethyl-(2-isopropoxy)phenyl (24)

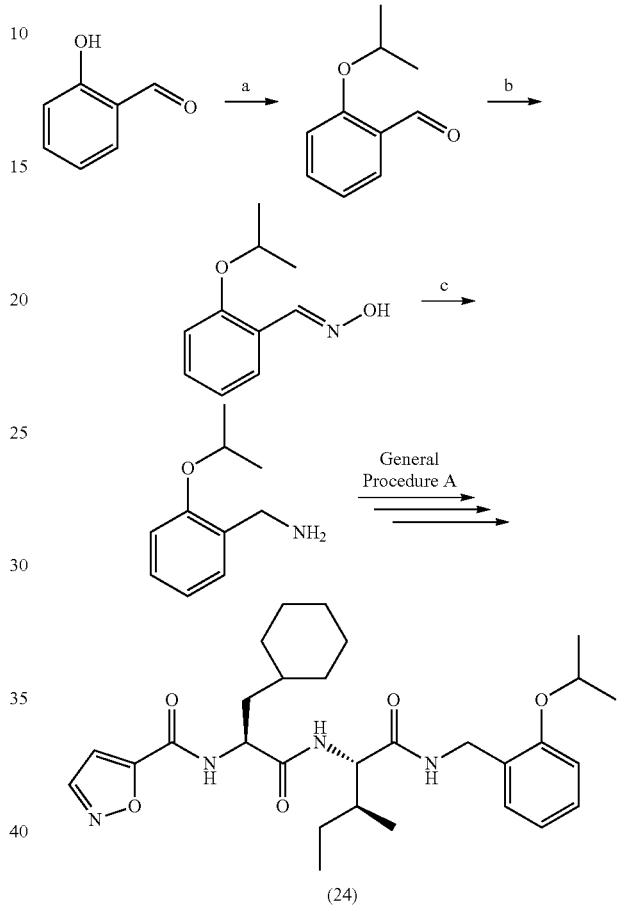

a) 2-iodopropane, DBU, 140° C.; b) NH₂OH; c) Zn, HCOONH₄

Step a: In a microwave reaction vial was loaded salicylaldehyde (1 eq), DMF, DBU (1 eq) and the corresponding 2-iodopropane. The vessel was sealed and the mixture was irradiated in Biotage Initiator microwave reactor (140° C., 10 min). The progress of the reaction was monitored by TLC (PE/EtOAc 4:1, product Rf ~0.5). Upon completion, the reaction mixture was allowed to cool down, diluted with EtOAc and washed with sat. Na₂CO₂ (3×) to remove starting material salicylaldehyde. The organic phase was dried over MgSO₄, filtered and evaporated to dryness to the give product as a yellow liquid (70% yield), which was used without further purification.

Step b: The resulting aldehyde was treated with hydroxylamine hydrochloride (2 eq.) and NaOH (4 eq.) in MeOH/H₂O (1:1) and stirred at room temperature for an hour. After completion, the reaction solution was evaporated to dryness and then re-dissolved in EtOAc, washed with 1 M HCl (2×), sat. NaHCO₃ (2×) and brine (1×). The organic phase was dried over MgSO₄, filtered and evaporated to dryness to give a waxy solid (90% yield).

Step c: To starting material oxime in MeOH, ammonium formate (2 eq.) and zinc dust (2 eq.) were added and the reaction mixture was refluxed for an hour. The reaction mixture was filtered through a pad of celite, washed with MeOH and the filtrate was evaporated. The impure crude was purified on preparative HPLC. The purified amine was coupled to Boc-protected isoleucine as described in the general amino acid coupling procedure A to give 24.

$^1$H NMR (600 MHz, CDCl$_3$), δ 0.81-0.87 (m, 6H), 0.87-1.01 (m, 2H), 1.06-1.34 (m, 6H), 1.36-1.38 (t, 6H, J=6 Hz), 1.40-1.49 (m, 1H), 1.63-1.73 (m, 6H), 1.76-1.84 (m, 1H), 4.19-4.22 (dd, 1H, J=6.6, 9.0 Hz), 4.38-4.42 (dd, 1H, J=6.0, 14.4 Hz), 4.44-4.48 (dd, 1H, J=6.0, 14.4 Hz), 4.59-4.65 (m, 2H), 6.21-6.23 (t, 1H, J=6 Hz), 6.58-6.60 (d, 1H, J=9.6 Hz), 6.86-6.89 (m, 2H), 6.91-6.92 (d, 1H, J=1.8 Hz), 7.01-7.03 (d, 1H, J=9 Hz), 7.22-7.24 (m, 1H), 8.33-8.34 (d, 1H, J=1.8 Hz).

HRMS: [MH]$^+$ 527.3228 (calc. for $C_{29}H_{43}N_4O_5{}^+$) 527.3231 (found).

Example 4

Preparation of 5-isoxazoyl-Cha-Ile-aminomethyl-(1,3-dioxalane)phenyl (26)

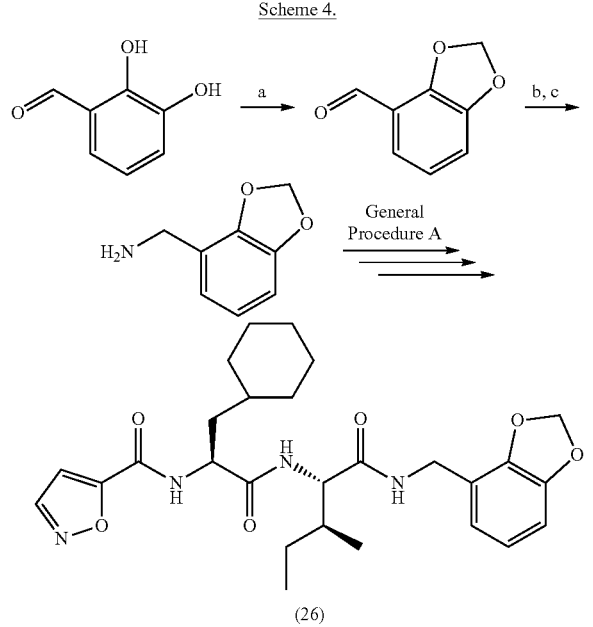

a) CH$_2$Br$_2$, CuO, K$_2$CO$_3$, DMF, 160° C.; b) H$_2$NOH, MeOH—H$_2$O; c) NH$_4$CHO, Pd/C.

Step a: In a round-bottomed flask containing DMF (16 mL), 2,3-dihydroxybenzaldehyde (2.0 g, 14.5 mmol), dibromomethane (1.4 mL, 17.4 mmol), cupric oxide (0.11 g, 1.45 mmol), K$_2$CO$_3$ (2.4 g, 17.4 mmol) were added and the reaction mixture was refluxed at 160° C. overnight. The reaction mixture was filtered through a pad of celite and the filter cake was washed with CH$_2$Cl$_2$. The filtrate was washed with H$_2$O (3×). The organic layer was dried over MgSO$_4$, filtered and evaporated to dryness to give dark brown oil. The oil was distilled using a Kugelrohr distillation apparatus (b.p. 120° C./0.1 mm) to give product as yellow oil (1.5 g, 69% yield).

Step b: The resulting aldehyde was treated with hydroxylamine hydrochloride (2 eq.) and NaOH (4 eq.) in MeOH/H$_2$O (1:1) and stirred at room temperature for an hour. After completion, the reaction solution was evaporated to dryness and then re-dissolved in EtOAc, washed with 1 M HCl (2×), sat. NaHCO$_3$ (2×) and brine (1×). The organic phase was dried over MgSO$_4$, filtered and evaporated to dryness to give a white solid (70% yield).

Step c: To starting material oxime (2.5 mmol) in MeOH, ammonium formate (2 eq.) and Pd/C (100 mg) were added and the reaction mixture was stirred at room temperature for 48 hours. The reaction mixture was filtered through a pad of celite, washed with MeOH and the filtrate was evaporated. The impure crude was purified on preparative HPLC. The purified amine was coupled to Boc-protected isoleucine as described in the general amino acid coupling procedure A to give 26.

$^1$H NMR (600 MHz DMSO-d$_6$), δ 0.84-0.90 (m, 6H), 0.90-1.01 (m, 2H), 1.05-1.23 (m, 4H), 1.29-1.37 (m, 1H), 1.43-1.50 (m, 1H), 1.60-1.75 (m, 6H), 1.76-1.81 (m, 1H), 1.84-1.92 (m, 1H), 4.25-4.27 (dd, 1H, J=7.2, 9.0 Hz), 4.39-4.42 (dd, 1H, J=6, 15 Hz), 4.47-4.51 (dd, 1H, J=6, 15 Hz), 4.62-4.66 (m, 1H), 5.96-5.97 (m, 2H), 6.19-6.24 (m, 1H), 6.52-6.58 (m, 1H), 6.74-6.80 (m, 3H), 6.91 (d, 1H, J=1.8 Hz), 7.03-7.08 (m, 1H), 8.33-8.34 (d, 1H, J=1.8 Hz).

HRMS: [MNa]$^+$ 535.2527 (calc. for $C_{27}H_{36}N_4Na_1O_6{}^+$) 535.2528 (found).

Example 5

Preparation of 5-isoxazoyl-Cha-Ile-aminomethyl-(3,4-dichloro)phenyl Represented by Formula (27)

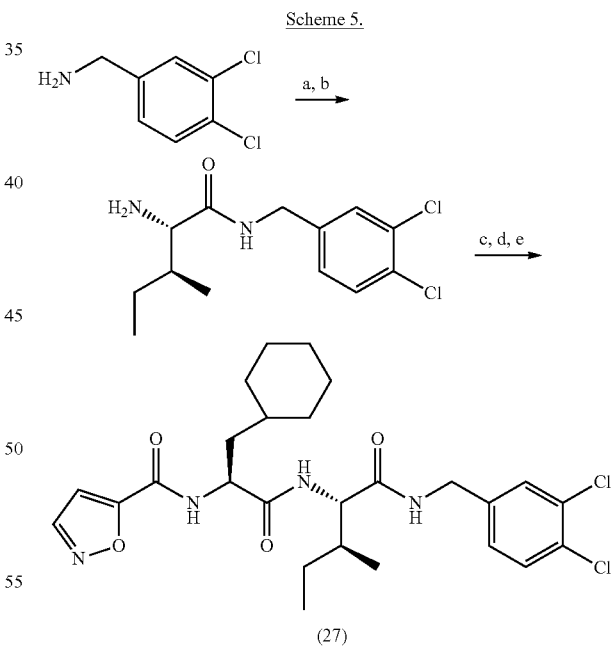

a) Boc-Ile-OH, HBTU/DIPEA in DMF; b) 20% TFA in DCM;
c) Boc-Cha-OH, HBTU/DIPEA in DMF; d) 20% TFA in DCM;
e) Isoxazole 5-carboxylic acid, HBTU/DIPEA in DMF Compound 27 was synthesised by following the general amino acid coupling procedure A.

$^1$H NMR (600 MHz, DMSO-d$_6$): δ 0.79-0.82 (m, 6H), 0.85-0.91 (m, 2H), 1.03-1.16 (m, 4H), 1.23-1.29 (m, 1H), 1.40-1.47 (m, 1H), 1.48-1.53 (m, 1H), 1.56-1.76 (m, 7H), 4.15-4.17 (t, 1H, J=8.4 Hz), 4.22-4.30 (m, 2H), 4.54-4.58

(m, 1H), 7.15-7.16 (d, 1H, J=1.8 Hz), 7.21-7.23 (dd, 1H, J=1.8, 7.8 Hz), 7.47 (d, 1H, J=1.8 Hz), 8.04-8.05 (d, 1H, J=8.4 Hz), 8.58-8.60 (t, 1H, J=6 Hz), 8.75-8.76 (d, 1H, J=1.8 Hz), 8.93-8.94 (d, 1H, J=8.4).

HRMS: [MH]$^+$ 537.2030 (calc. for $C_{26}H_{35}Cl_2N_4O_4{}^+$) 537.2028 (found).

Example 6

Preparation of 5-isoxazoyl-Cha-Ile-(4-phenyl)piperidine (30)

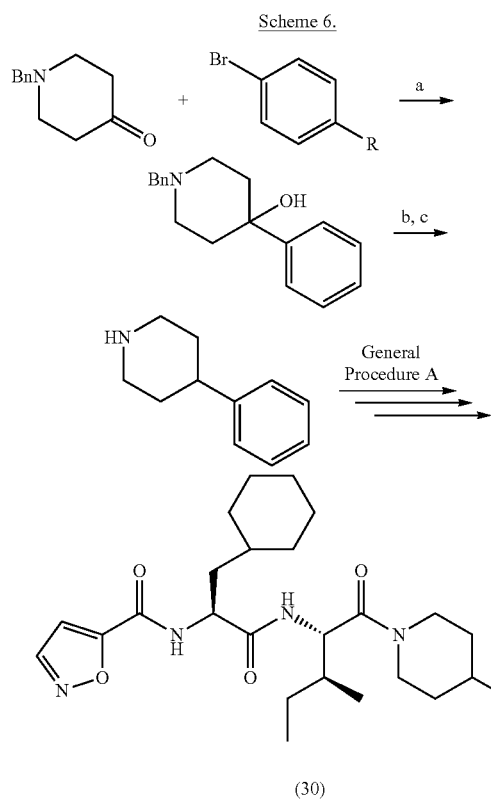

(30)

a) Mg, THF, 65° C.; b) Pd/C, cat. HCl, 50 psi; c) 4M HCl in THF

Step a: Grignard Reaction: To a dry, nitrogen filled 2-necked round bottom flask was loaded magnesium turning (500 mg, 20 mmol), a small amount of iodine crystal and dry THF (3.8 mL). While stirring in a warm water bath (55-65° C.), a solution of bromobenzene (20.05 mmol) in anhydrous THF (5 mL) was loaded into a dry syringe and ⅓ of the solution was slowly transferred into the flask to initiate the reaction (Note: the colour slowly changed from dark brown to light brown). When the mixture began to boil, the water bath was removed and the mixture was diluted with dry THF (5 mL). The remaining bromobenzene solution was then slowly added to the flask. After refluxing the mixture for 20 min (65° C.), the mixture was cooled in an ice-water bath and a solution of 1-Boc-4-piperidone (2 g, 10 mmol) in dry THF (5 mL) was added drop wise (during which a white solid formed). Upon addition, the mixture was allowed to stir at room temperature for a further 30 minutes. A chilled solution of 10% citric acid was added and the mixture stirred for 1 minute (resulting in the formation of a gummy solid). Diethyl ether and water were added to dissolve the solid and the layers were separated. The aqueous layer was washed with ether (2×). The combined organic layer was washed with water (1×), dried over anhydrous MgSO$_4$, filtered and evaporated in vacuo. The crude product was purified by silica gel column chromatography, eluting with Petroleum Spirit/Ethyl Acetate (4:1) to give a white crystal product (0.96 g, 34.5% yield).

Step b: Hydrogenolysis: A mixture of the above crude product (200 mg), 10% Pd/C, and a catalytic amount of concentrated HCl (1.2 mL) in EtOH (20 mL) were hydrogenated at 50 psi for an hour. The Pd/C was filtered through a pad of celite, and the solvent was evaporated in vacuo.

Step c: Boc deprotection: The above crude was treated with 4 M HCl (4 mL) in THF (4 mL) for an hour. The THF solvent and HCl was evaporated and the residue was dissolved in DCM and washed with saturated NaHCO$_3$ (2×). Organic layers were dried over MgSO$_4$, filtered, and evaporated in vacuo. The residue amine (110.4 mg, 95% yield) was coupled Boc-protected isoleucine as described in the general amino acid coupling procedure A to give 30.

$^1$H NMR (400 MHz, CDCl$_3$): δ 0.84-1.02 (m, 7H), 1.08-1.26 (m, 4H), 1.32-1.54 (m, 2H), 1.57-1.83 (m, 10H), 1.94-2.05 (m, 3H), 2.68-2.83 (m, 2H), 3.16-3.26 (m, 1H), 4.11-4.20 (m, 1H), 4.64-4.72 (m, 1H), 4.73-4.80 (m, 1H), 4.87-4.93 (q, 1H, J=6.8 Hz), 6.76-6.84 (t, 1H, 9.2 Hz), 6.93-6.95 (br d, 1H, J=2 Hz), 7.05-7.11 (t, 1H, J=8 Hz), 7.17-7.25 (m, 3H), 7.29-7.34 (m, 2H), 8.33-8.34 (d, 1H, J=1.6 Hz).

HRMS: [MH]$^+$ 523.3279 (calc. for $C_{30}H_{43}N_4O_4{}^+$) 523.3280 (found).

Example 7

Preparation of 5-isoxazoyl-Cha-Ile-spiro[chroman-2,4'-piperidine] (37)

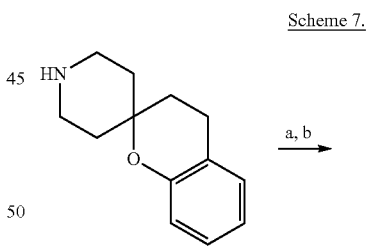

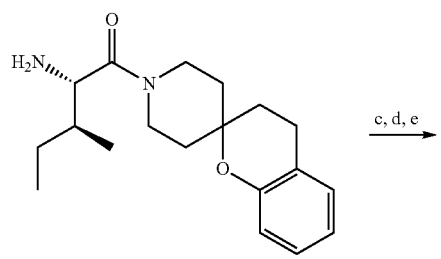

-continued

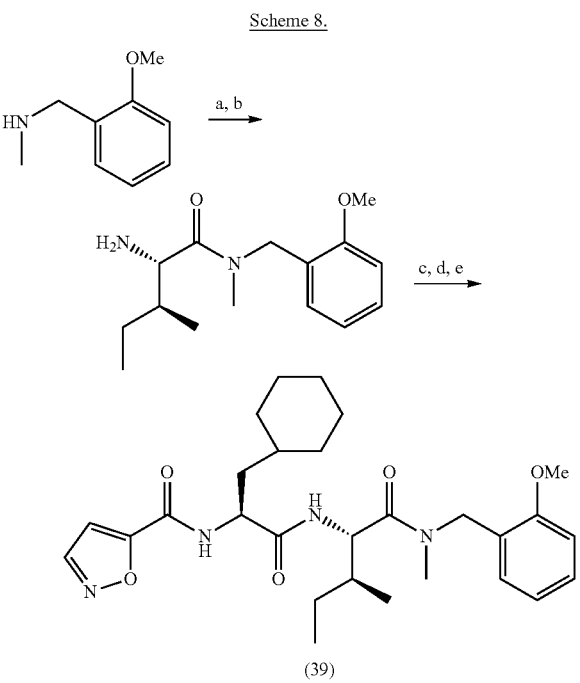

(37)

a) Boc-Ile-OH, HBTU/DIPEA in DMF; b) 20% TFA in DCM;
c) Boc-Cha-OH, HBTU/DIPEA in DMF; d) 20% TFA in DCM;
e) Isoxazole 5-carboxylic acid, HBTU/DIPEA in DMF Compounds were synthesised by following general amino acid coupling procedure A.

$^1$H NMR (600 MHz, DMSO-d$_6$), δ 0.85-1.00 (m, 8H), 1.11-1.24 (m, 6H), 1.49-1.59 (m, 3H), 1.60-1.72 (m, 6H), 1.74-1.85 (m, 4H), 1.86-2.00 (m, 1H), 2.01-2.22 (m, 1H), 2.77-2.82 (m, 1H), 3.15-3.28 (m, 1H), 3.57-3.69 (m, 1H), 3.92-4.00 (m, 1H), 4.40-4.47 (m, 1H), 4.68-4.76 (m, 1H), 4.88-4.92 (t, 1H, J=8.4 Hz), 6.68 (br s, 2H), 6.82-7.14 (m, 4H), 7.31-7.57 (m, 1H), 8.34-8.35 (d, 1H, J=1.2 Hz).

HRMS: [MH]$^+$565.3384 (calc. for C$_{32}$H$_{45}$N$_4$O$_5^+$) 5653385 (found).

Example 8

Preparation of 5-isoxazoyl-Cha-Ile-aminodimethyl-(2-methoxy)phenyl (39)

Scheme 8.

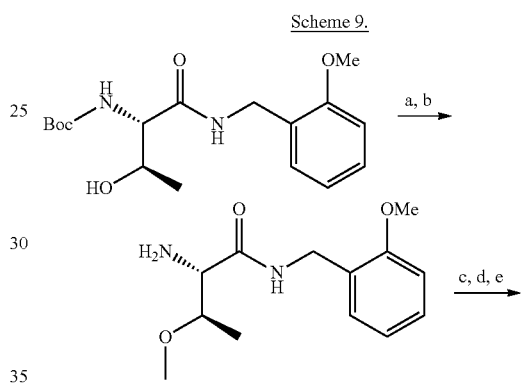

(39)

a) Boc-Ile-OH, HBTU/DIPEA in DMF; b) 20% TFA in DCM;
c) Boc-Cha-OH, HBTU/DIPEA in DMF; d) 20% TFA in DCM;
e) Isoxazole 5-carboxylic acid, HBTU/DIPEA in DMF Compound 39 was synthesised by following the general amino acid coupling procedure A.

$^1$H NMR (600 MHz, DMSO-d$_6$): δ 0.75-0.76 (d, 1H, J=6.6 Hz), 0.78-0.81 (t, 1H, J=7.8 Hz), 0.86-0.88 (m, 4H), 0.90-0.96 (m, 2H), 1.00-1.15 (m, 3H), 1.18-1.22 (m, 1H), 1.32-1.38 (m, 1H) 1.45-1.59 (m, 2H), 1.60-1.78 (m, 6H), 1.83-1.88 (m, 1H), 2.80 (s, 1H), 3.09 (s, 2H), 3.82 (s, 3H) 4.3-4.65 (m, 4H), 6.86-6.88 (t, 1H, J=7.2 Hz), 6.94-6.96 (m, 1H), 7.01-7.11 (m, 1H), 7.19-7.20 (m, 1H), 7.26-7.33 (m, 1H), 8.33-8.35 (d, 1H, J=9 Hz), 8.78-8.79 (m, 1H), 8.96-8.99 (m, 1H).

HRMS: [MH]$^+$513.3071 (calc. for C$_{28}$H$_{41}$N$_4$O$_5^+$) 513.3071 (found).

Example 9

Preparation of 5-isoxazoyl-Cha-Thr(Me)-aminomethyl-(2-methoxy)phenyl (40)

Scheme 9.

(40)

a) MeI, LiO$^t$Bu, DMF; b) 20% TFA in DCM; c) Boc-Cha-OH, HBTU/DIPEA in DMF;
d) 20% TFA in DCM; e) isoxazole-5-carboxylic acid, HBTU/DIPEA in DMF Step a: To a crude of Boc-Thr-aminomethyl-(2-methoxy)phenyl (0.541 mmol, prepared by following general amino acid coupling procedure A from 2-methoxybenzylamine and Boc-Thr-OH) was dissolved in MT (3 mL). Lithium tert-butoxide (28.4 mg, 0.568 mmol, 1.05 eq) was added. The mixture was stirred at room temperature for 1 h. Methyl iodide (37 µL, 0.595 mmol, 1.1 eq) was added. The mixture was stirred at room temperature overnight, diluted with ethyl acetate (20 mL) and washed with brine (30 mL). The organic phase was dried (MgSO$_4$), filtered and evaporated on rotavapor to dryness.

Steps b-e: Following general amino acid coupling procedure A, the above crude was deprotected and coupled sequentially with Boc-Cha-OH and isoxazole-5-carboxylic acid to give compound 40.

$^1$H NMR (400 MHz, CDCl$_3$), δ 0.85-1.40 (m, 9H), 1.60-1.81 (m, 7H), 3.37 (s, 3H), 3.77-3.84 (m, 1H, β-CH of

Thr), 3.84 (s, 3H), 4.38-4.46 (m, 2H, PhCH$_2$), 4.50 (dd, 1H, J=6.4, 3.2 Hz, α-CH of Thr), 4.63-4.69 (m, 1H, α-CH of Cha), 6.84-6.91 (m, 3H), 7.02-7.12 (m, 3H), 7.21-7.27 (m, 2H), 8.31 (d, 1H, J=2 Hz); $^{13}$C NMR (100 MHz, CDCl$_3$), δ 171.4, 168.7, 162.2, 157.4, 155.6, 151.0, 129.5, 129.0, 125.3, 120.6, 110.2, 106.9, 75.6, 56.9, 55.6, 55.2, 51.4, 40.2, 39.7, 34.1, 33.6, 32.5, 26.2, 26.0, 25.9, 14.0.

HRMS: [MH]$^+$ 501.2708 (calc. for $C_{26}H_{37}N_4O_6^+$) 501.2708 (found).

Example 10

Preparation of 5-(3-amino-isoxazoyl)-Cha-Ile-spiro[indene-1,4'-piperidine] (42)

Scheme 10.

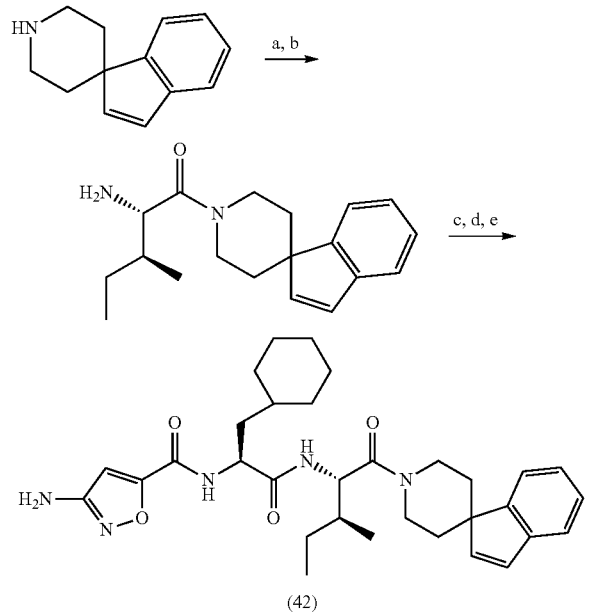

(42)

a) Boc-Ile-OH, HBTU/DIPEA in DMF; b) 20% TFA in DCM;
c) Boc-Cha-OH, HBTU/DIPEA in DMF; d) 20% TFA in DCM;
e) 3-aminoisoxazole-5-carboxylic acid, BOP/DIPEA in DMF.

Compounds were synthesised by following general amino acid coupling procedure A.

$^1$H NMR (400 MHz, CDCl$_3$), δ 0.86-2.23 (m, 26H), 3.05-3.16 (m, 1H), 3.44-3.59 (m, 1H), 4.19-4.26 (m, 1H), 4.37 (lump, NH$_2$ overlapped with DOH, partially exchangeable with D$_2$O), 4.60-4.77 (m, 2H), 4.93-5.01 (m, 1H), 6.47 (s, 1H), 6.82-6.87 (m, 2H), 7.18-7.49 (m; 6H); $^{13}$C NMR (100 MHz, CDCl$_3$, two rotamers due to amide bond rotation), δ 171.9 (0)/171.8 (4), 170.6 (8)/170.6 (4), 163.6, 162.0, 155.8, 150.7 (5)/150.7 (0), 142.8/142.5, 139.7/139.3, 131.1/131.0, 127.4/127.3, 125.7, 125.5, 121.8, 121.6/121.4, 99.9, 53.1, 51.9/51.8, 51.5/51.4, 45.6/45.1, 41.5/41.4, 40.2/40.1, 37.9 (4)/37.8 (8), 34.1, 34.0, 33.6 (2)/33.5 (9), 33.4/33.2, 32.4 (2)/32.4 (0), 26.2, 26.1 (3)/26.1 (0), 26.0, 24.2, 16.0/15.6, 11.4/11.2.

HRMS: [MH]$^+$ 562.3388 (calc. for $C_{32}H_{44}N_5O_4^+$) 562.3388 (found).

Example 11

Preparation of 5-isoxazoyl-Cha-Thr(Me)-spiro[indene-1,4'-piperidine] (44)

Scheme 11.

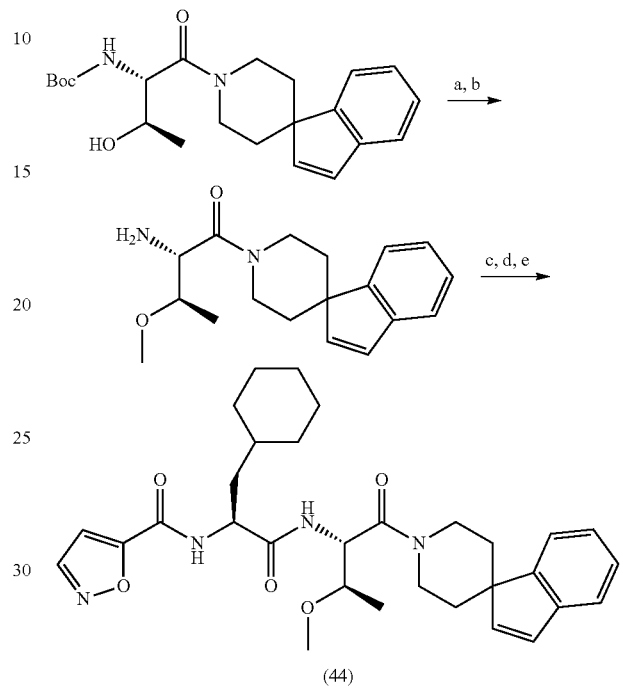

(44)

a) MeI, LiO$^t$Bu, DMF; b) 20% TFA in DCM; c) Boc-Cha-OH, HBTU/DIPEA in DMF;
d) 20% TFA in DCM; e) isoxazole-5-carboxylic acid, HBTU/DIPEA in DMF Step a: To a crude of Boc-Thr-spiro[indene-1,4'-piperidine] (0.270 mmol, prepared by following general amino acid coupling procedure A from spiro[indene-1,4'-piperidine] and Boc-Thr-OH) was dissolved in DMF (3 mL). Lithium tert-butoxide (23 mg, 0.284 mmol, 1.05 eq) was added. The mixture was stirred at room temperature for 1 h. Methyl iodide (18.5 µL, 0.297 mmol, 1.1 eq) was added. The mixture was stirred at room temperature overnight, diluted with ethyl acetate (20 mL) and washed with brine (30 mL). The organic phase was dried (MgSO$_4$), filtered and evaporated on rotavapor to dryness.

Steps b-e: Following general amino acid coupling procedure A, the above crude was deprotected and coupled sequentially with Boc-Cha-OH and isoxazole-5-carboxylic acid to give compound 44.

$^1$H NMR (400 MHz, CDCl$_3$), δ 0.88-1.32 (M, 8H), 1.36-1.50 (m, 3H), 1.63-2.16 (m, 9H), 3.07-3.17 (m, 1H), 3.44-3.53 (m, 1H), 3.35 (s)/3.40 (s, 3H, OMe of two rotamers), 3.66 (m, 1H, β-CH of Thr), 4.17 (br s, 1H), 4.65-4.72 (m, 1H), 4.72-4.79 (m, 1H, α-CH of Cha), 5.12 (1H, dd, J=8.0, 4.0 Hz, α-CH of Thr), 6.83 (d, 1H, J=6.0 Hz), 6.85 (d, 1H, J=6.0 Hz), 6.96 (d, 1H, J=1.6 Hz), 7.19-7.40 (m, 6H), 8.35 (d, 1H, J=2 Hz); $^{13}$C NMR (100 MHz, CDCl$_3$, two rotamers due to amide bond rotation), δ171.9 (0)/171.8 (4), 170.6 (8)/170.6 (5), 163.6, 162.1, 155.8, 150.8/150.7, 142.8/142.5, 139.7/139.3, 131.1/131.0, 127.4/127.3, 125.7/125.5, 121.8, 121.6/121.4, 99.9, 53.1, 51.9/51.8, 51.5/51.4, 45.6/45.1, 41.5/41.1, 40.2/40.1, 37.9 (4)/37.8 (8), 34.1, 34.0, 33.6 (2)/33.5 (9), 33.4/33.2, 32.4 (2)/32.4 (0), 26.2, 26.1 (3)/26.1 (0), 26.0, 24.2, 16.0/15.6, 11.4/11.2.

HRMS: [MH]$^+$ 549.3071 (calc. for $C_{31}H_{41}N_4O_5{}^+$) 549.3076 (found).

Further exemplary compounds of the formula (I) are provided below in Tables 1 to 4.

TABLE 1

HRMS data for representative compounds of formula (I)

| Z | Formula for [M + H]$^+$ | HRMS* Calc. | Found |
|---|---|---|---|
| OH | $C_{19}H_{30}N_3O_5{}^+$ | 380.2180 | 380.2176 |
| OMe | $C_{20}H_{31}NaN_3O_5{}^+$ [M + Na]$^+$ | 416.2156 | 416.2155 |
| (3-(methylaminomethyl)benzoyl-ornithinamide) | $C_{32}H_{48}N_7O_6{}^+$ | 626.3661 | 626.3667 |
| (3-(methylaminomethyl)benzoyl-diaminobutyramide) | $C_{31}H_{46}N_7O_6{}^+$ | 612.3504 | 612.3514 |
| (N-methylbenzylamine) | $C_{26}H_{37}N_4O_4{}^+$ | 469.2809 | 469.2818 |
| (N,N-dimethylbenzylamine) | $C_{27}H_{39}N_4O_4{}^+$ | 483.2966 | 483.2970 |
| (N-methyl-2-fluorobenzylamine) | $C_{26}H_{36}FN_4O_4{}^+$ | 487.2715 | 487.2718 |
| (N-methyl-3-fluorobenzylamine) | $C_{26}H_{36}FN_4O_4{}^+$ | 487.2715 | 487.2712 |
| (N-methyl-4-fluorobenzylamine) | $C_{26}H_{36}FN_4O_4{}^+$ | 487.2715 | 487.2719 |

TABLE 1-continued
HRMS data for representative compounds of formula (I)
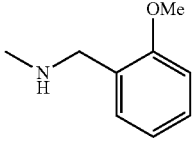
| Z | Formula for [M + H]$^+$ | HRMS* Calc. | Found |
|---|---|---|---|
| 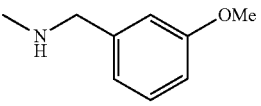 2-OMe benzyl N-methyl | $C_{27}H_{39}N_4O_5^+$ | 499.2915 | 499.2915 |
| 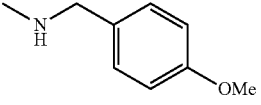 3-OMe benzyl N-methyl | $C_{27}H_{39}N_4O_5^+$ | 499.2915 | 499.2918 |
| 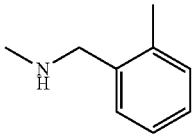 4-OMe benzyl N-methyl | $C_{27}H_{39}N_4O_5^+$ | 499.2915 | 499.2918 |
| 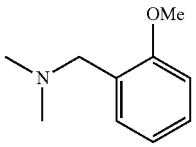 2-Me benzyl N-methyl | $C_{27}H_{39}N_4O_4^+$ | 483.2966 | 483.2965 |
| 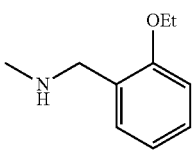 2-OMe benzyl N,N-dimethyl | $C_{28}H_{41}N_4O_5^+$ | 513.3071 | 513.3071 |
| 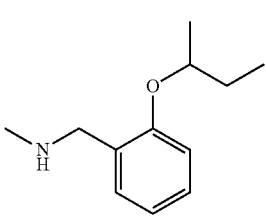 3-OEt benzyl N-methyl | $C_{28}H_{41}N_4O_5^+$ | 513.3071 | 513.3071 |
| 2-(sec-butoxy) benzyl N-methyl | $C_{30}H_{45}N_4O_5^+$ | 541.3384 | 541.3387 |

TABLE 1-continued
HRMS data for representative compounds of formula (I)
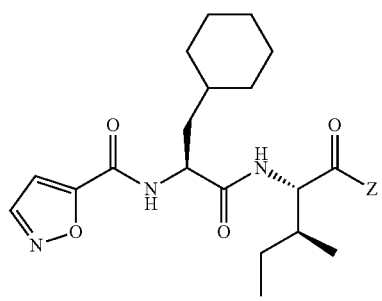
| Z | Formula for [M + H]$^+$ | HRMS* Calc. | Found |
|---|---|---|---|
| 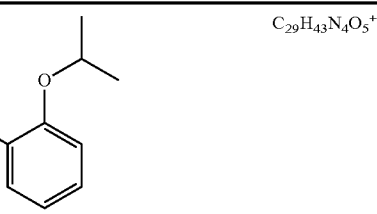 | $C_{29}H_{43}N_4O_5^+$ | 527.3228 | 527.3231 |
| 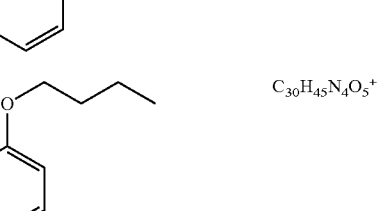 | $C_{29}H_{43}N_4O_5^+$ | 527.3228 | 527.3227 |
| 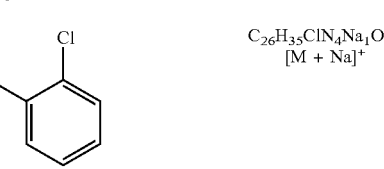 | $C_{30}H_{45}N_4O_5^+$ | 541.3384 | 541.3388 |
|  | $C_{26}H_{35}ClN_4Na_1O_4^+$ [M + Na]$^+$ | 525.2239 | 525.2239 |
|  | $C_{27}H_{35}F_3N_4Na_1O_4^+$ [M + Na]$^+$ | 559.2503 | 559.2502 |
| 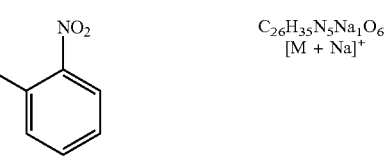 | $C_{27}H_{36}F_3N_4O_5^+$ | 553.2632 | 553.2632 |
|  | $C_{26}H_{35}N_5Na_1O_6^+$ [M + Na]$^+$ | 536.2480 | 536.2481 |

TABLE 1-continued
HRMS data for representative compounds of formula (I)
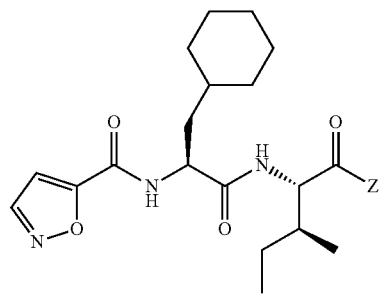
| Z | Formula for [M + H]$^+$ | HRMS* Calc. | Found |
|---|---|---|---|
| 2,4-dimethoxybenzyl-NHMe | $C_{28}H_{41}N_4O_6^+$ | 529.3021 | 529.3022 |
| 2,5-dimethoxybenzyl-NHMe | $C_{28}H_{41}N_4O_6^+$ | 529.3021 | 529.3021 |
| 3,4-dimethoxybenzyl-NHMe | $C_{28}H_{41}N_4O_6^+$ | 529.3021 | 529.3022 |
| 2,3-dimethoxybenzyl-NHMe | $C_{28}H_{41}N_4O_6^+$ | 529.3021 | 529.3021 |
| 3,4,5-trimethoxybenzyl-NHMe | $C_{29}H_{43}N_4O_7^+$ | 559.3126 | 559.3125 |
| 2,6-dimethoxybenzyl-NHMe | $C_{28}H_{41}N_4O_6^+$ | 529.3021 | 529.3021 |
| benzo[d][1,3]dioxol-5-ylmethyl-NHMe | $C_{27}H_{37}N_4O_6^+$ | 513.2708 | 513.2708 |

TABLE 1-continued

HRMS data for representative compounds of formula (I)

| Z | Formula for [M + H]⁺ | HRMS* Calc. | Found |
|---|---|---|---|
| (methylamino-methyl)-benzo[1,3]dioxole | $C_{27}H_{36}N_4Na_1O_6^+$ [M + Na]⁺ | 535.2527 | 535.2528 |
| 2-OMe-5-OCF₃-benzyl(methylamino) | $C_{28}H_{38}F_3N_4O_6^+$ | 583.2738 | 583.2739 |
| 3,4-dichlorobenzyl(methylamino) | $C_{26}H_{35}Cl_2N_4O_4^+$ | 537.2030 | 537.2028 |
| 3,5-bis(trifluoromethyl)benzyl(methylamino) | $C_{28}H_{35}F_6N_4O_4^+$ | 605.2557 | 605.2556 |
| 2-biphenyl-methyl(methylamino) | $C_{32}H_{41}N_4O_4^+$ | 545.3122 | 545.3121 |
| 3-biphenyl-methyl(methylamino) | $C_{32}H_{41}N_4O_4^+$ | 545.3122 | 545.3125 |

TABLE 1-continued

HRMS data for representative compounds of formula (I)

| Z | Formula for [M + H]⁺ | HRMS* Calc. | Found |
|---|---|---|---|
| N-methyl-4-biphenylmethylamine | $C_{32}H_{41}N_4O_4^+$ | 545.3122 | 545.3123 |
| N-methyl-1-naphthylmethylamine | $C_{30}H_{39}N_4O_4^+$ | 519.2966 | 519.2968 |
| 1-methyl-4-phenylpiperidine | $C_{30}H_{43}N_4O_4^+$ | 523.3279 | 523.3280 |
| 1-methyl-4-(4-chlorophenyl)piperidine | $C_{30}H_{42}ClN_4O_4^+$ | 577.2889 | 577.2894 |
| 1-methyl-4-(4-methoxyphenyl)piperidine | $C_{31}H_{45}N_4O_5^+$ | 553.3384 | 553.3384 |
| 1-methyl-4-(2,5-dimethoxyphenyl)piperidine | $C_{32}H_{47}N_4O_6^+$ | 583.3490 | 583.3492 |
| 1-methyl-4-benzylpiperidine | $C_{31}H_{45}N_4O_4^+$ | 537.3435 | 537.3449 |

TABLE 1-continued
HRMS data for representative compounds of formula (I)
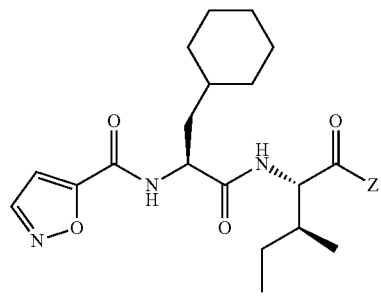
| Z | Formula for [M + H]$^+$ | HRMS* Calc. | Found |
|---|---|---|---|
| (N-methylpiperidine with 2-CF$_3$-phenyl) | $C_{31}H_{42}F_3N_4O_4^+$ | 591.3153 | 591.3156 |
| (N-methyl-4-hydroxypiperidine with 2,4-bis(CF$_3$)phenyl) | $C_{32}H_{41}F_6N_4O_5^+$ | 675.2976 | 675.2976 |
| (N-methylpiperidine with 2-biphenyl) | $C_{36}H_{47}N_4O_4^+$ | 599.3592 | 599.3597 |
| (N-methylpiperidine with 3-biphenyl) | $C_{36}H_{47}N_4O_4^+$ | 599.3592 | 599.3590 |
| (N-methylpiperidine with 4-biphenyl) | $C_{36}H_{47}N_4O_4^+$ | 599.3592 | 599.3594 |

TABLE 1-continued

HRMS data for representative compounds of formula (I)

[Structure: isoxazole-C(=O)-NH-CH(CH2-cyclohexyl)-C(=O)-NH-CH(CH(CH3)CH2CH3)-C(=O)-Z]

| Z | Formula for [M + H]⁺ | HRMS* Calc. | Found |
|---|---|---|---|
| *N-tert-butyl 1-methylpiperidine-2-carboxamide group* | $C_{29}H_{48}N_5O_5^+$ | 546.3650 | 546.3653 |
| *4-acetamido-4-phenyl-1-methylpiperidine group* | $C_{32}H_{46}N_5O_5^+$ | 580.3493 | 580.3493 |
| *6,7-dimethoxy-2-methyl-1,2,3,4-tetrahydroisoquinoline group* | $C_{30}H_{43}N_4O_6^+$ | 555.3177 | 555.3179 |
| *1-methyl-3-(2-fluorophenylamino)piperidine group* | $C_{30}H_{43}FN_5O_4^+$ | 556.3294 | 556.3296 |
| *1-methyl-3-(3-fluorophenylamino)piperidine group* | $C_{30}H_{43}FN_5O_4^+$ | 556.3294 | 556.3293 |
| *1-methyl-3-(4-fluorophenylamino)piperidine group* | $C_{30}H_{43}FN_5O_4^+$ | 556.3294 | 556.3298 |
| *1-methyl-3-(2-trifluoromethylphenylamino)piperidine group* | $C_{31}H_{43}F_3N_5O_4^+$ | 606.3262 | 606.3263 |

TABLE 1-continued

HRMS data for representative compounds of formula (I)

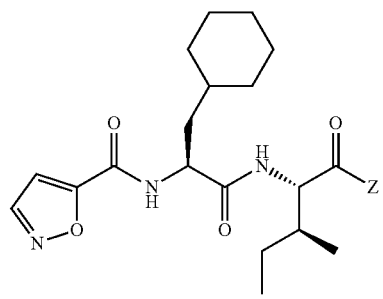

|  | HRMS* | | |
| Z | Formula for [M + H]+ | Calc. | Found |
| ![Z1](methylpiperidinyl-NH-CF3-phenyl) | $C_{31}H_{43}F_3N_5O_4^+$ | 606.3262 | 606.3265 |
| ![Z2](methylpiperidinyl-NH-CF3-phenyl) | $C_{31}H_{43}F_3N_5O_4^+$ | 606.3262 | 606.3269 |

TABLE 2

HRMS data for representative compounds of formula (I)

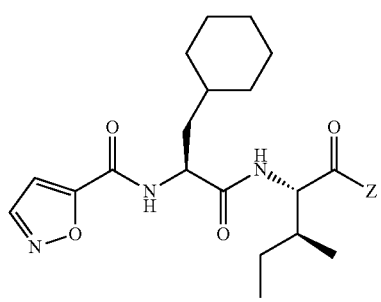

| Z | Formula | Calc. | Found |
| ![Z3](methylpiperidine-spiro-chromanone) | $C_{32}H_{43}N_4O_6^+$ | 579.3177 | 579.3178 |
| ![Z4](methylpiperidine-spiro-isobenzofuranone) | $C_{31}H_{40}N_4NaO_6^+$ [M + Na]+ | 587.2840 | 587.2843 |

TABLE 2-continued
HRMS data for representative compounds of formula (I)
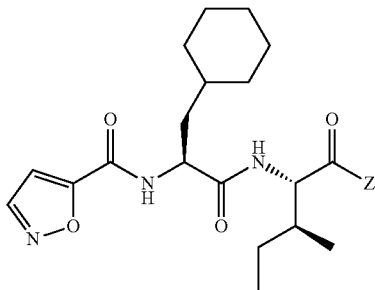
| | | | |
|---|---|---|---|
| 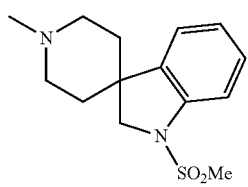 | $C_{32}H_{45}N_5NaO_6S^+$ [M + Na]$^+$ | 650.2983 | 650.2985 |
| 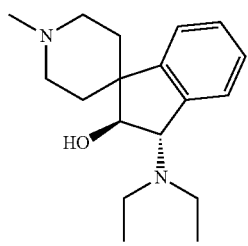 | $C_{36}H_{54}N_5O_5^+$ | 636.4119 | 636.4135 |
| 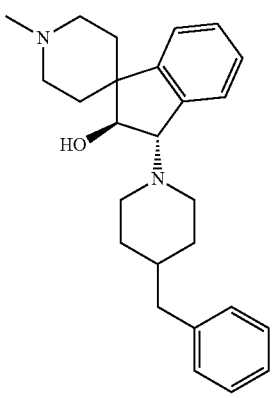 | $C_{44}H_{60}N_5O_5^+$ | 738.4589 | 738.4590 |
| 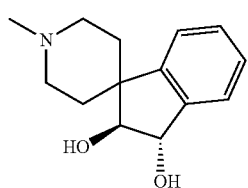 | $C_{32}H_{45}N_4O_6^+$ | 581.3334 | 581.3335 |

TABLE 2-continued
HRMS data for representative compounds of formula (I)
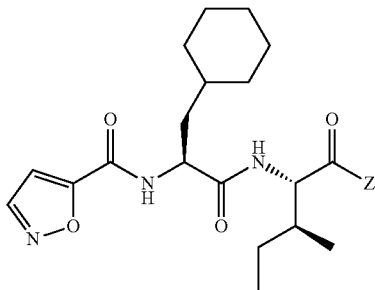
| | | | |
|---|---|---|---|
| 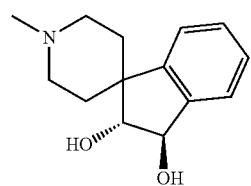 | $C_{32}H_{45}N_4O_6^+$ | 581.3334 | 581.3335 |
| 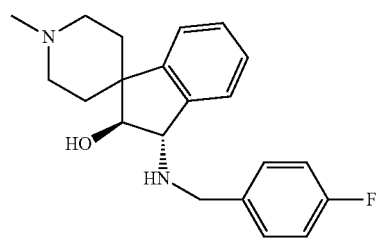 | $C_{39}H_{51}FN_5O_5^+$ | 688.3869 | 688.3901 |
| 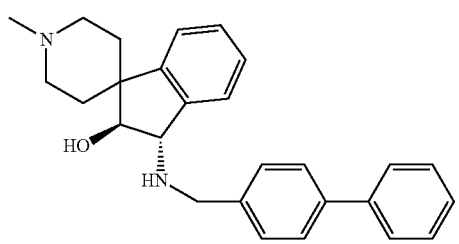 | $C_{45}H_{56}N_5O_5^+$ | 746.4276 | 746.4277 |
| 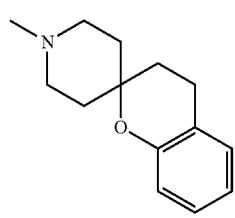 | $C_{32}H_{45}N_4O_5^+$ | 565.3384 | 565.3385 |

TABLE 3
HRMS data for representative compounds of formula (I)
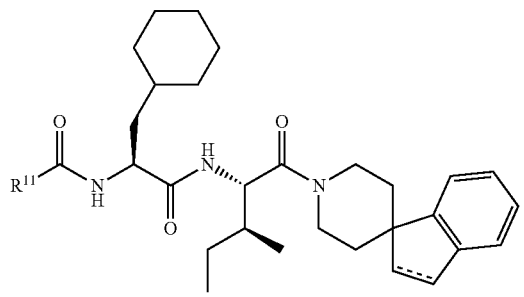
n = 1, single bond
n = 2, double bond
| n | R[11] | Formula for [M + H]+ | HRMS* Calc. | Found |
|---|---|---|---|---|
| 2 | furan-2-yl | $C_{33}H_{44}N_3O_4^+$ | 546.3326 | 546.3330 |
| 2 | pyridin-3-yl | $C_{34}H_{45}N_4O_3^+$ | 557.3486 | 557.3494 |
| 2 | pyrazin-2-yl | $C_{33}H_{44}N_5O_3^+$ | 558.3439 | 558.3443 |
| 2 | 1H-1,2,4-triazol-3-yl | $C_{31}H_{43}N_6O_3^+$ | 547.3391 | 547.3395 |
| 2 | 5-methylisoxazol-3-yl | $C_{33}H_{45}N_4O_4^+$ | 561.3435 | 561.3428 |
| 2 | 1H-imidazol-4-yl | $C_{32}H_{44}N_5O_3^+$ | 546.3439 | 546.3437 |
| 2 | 1-methyl-1H-pyrazol-4-yl | $C_{33}H_{46}N_5O_3^+$ | 560.3601 | 560.3595 |

TABLE 3-continued
HRMS data for representative compounds of formula (I)
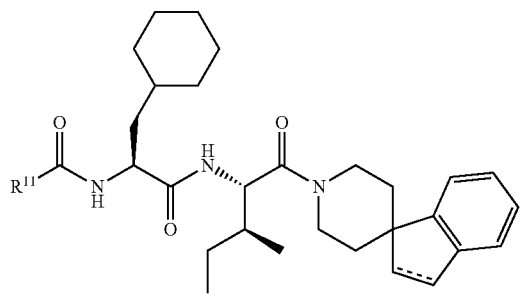
n = 1, single bond
n = 2, double bond
| n | R11 | Formula for [M + H]+ | HRMS* Calc. | Found |
|---|---|---|---|---|
| 2 | 3,5-dimethoxyphenyl (MeO, OMe) | $C_{37}H_{49}N_3Na_1O_5^+$ [M + Na]+ | 638.3564 | 638.3573 |
| 2 | diphenylmethyl | $C_{42}H_{51}N_3Na_1O_3^+$ | 668.3823 | 668.3819 |
| 2 | indol-3-yl | $C_{37}H_{47}N_4O_3^+$ | 595.3643 | 595.3644 |
| 2 | 5-(4-methylphenyl)isoxazol-3-yl | $C_{39}H_{49}N_4O_4^+$ | 637.3748 | 637.3752 |
| 2 | (E)-2-(pyridin-3-yl)vinyl | $C_{36}H_{47}N_4O_3^+$ | 583.3643 | 583.3645 |
| 2 | (E)-2-(3-chlorophenyl)vinyl | $C_{37}H_{47}ClN_3O_3^+$ | 616.3300 | 616.3296 |

TABLE 3-continued

HRMS data for representative compounds of formula (I)

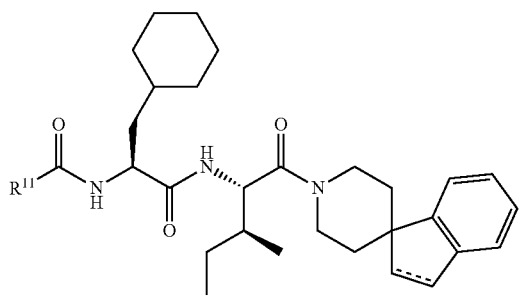

n = 1, single bond
n = 2, double bond

| n | R$^{11}$ | Formula for [M + H]$^+$ | HRMS* Calc. | Found |
|---|---|---|---|---|
| 2 | ~~~\/\/ | C$_{32}$H$_{48}$N$_3$O$_3^+$ | 522.3696 | 522.3698 |
| 2 | 5-oxopyrrolidin-2-yl | C$_{33}$H$_{47}$N$_4$O$_4^+$ | 563.3592 | 563.3593 |
| 2 | pyrrolidin-2-yl | C$_{33}$H$_{49}$N$_4$O$_3^+$ | 549.3799 | 549.3792 |
| 2 | H$_2$N-CH$_2$- | C$_{30}$H$_{45}$N$_4$O$_3^+$ | 509.3486 | 509.3492 |
| 2 | H$_2$N-(CH$_2$)$_3$- | C$_{32}$H$_{49}$N$_4$O$_3^+$ | 537.3799 | 537.3790 |
| 2 | H$_2$N-(CH$_2$)$_4$- | C$_{32}$H$_{51}$N$_4$O$_3^+$ | 539.3956 | 539.3956 |
| 2 | H$_2$N-CH$_2$-CH(OH)-CH$_2$- | C$_{32}$H$_{49}$N$_4$O$_4^+$ | 553.3748 | 553.3748 |
| 2 | H$_2$N-CH(CH$_2$OH)- | C$_{31}$H$_{47}$N$_4$O$_4^+$ | 539.3592 | 539.3589 |
| 2 | piperidin-4-yl | C$_{34}$H$_{51}$N$_4$O$_3^+$ | 563.3956 | 563.3956 |

TABLE 3-continued
HRMS data for representative compounds of formula (I)
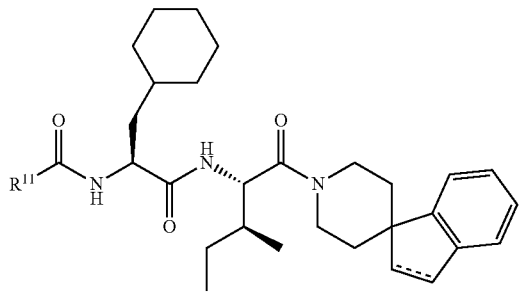
n = 1, single bond
n = 2, double bond
| n | R[11] | Formula for [M + H]+ | HRMS* Calc. | Found |
|---|---|---|---|---|
| 2 | (cyclohexane with 4 OH groups) | $C_{35}H_{52}N_3O_7^+$ | 626.3800 | 626.3806 |
| 2 | $H_2N$–CH$_2$CH$_2$–CH(OH)– | $C_{32}H_{49}N_4O_4^+$ | 553.3748 | 553.3750 |
| 1 | $H_2N$–CH$_2$CH$_2$–CH(OH)– | $C_{32}H_{51}N_4O_4^+$ | 555.3905 | 555.3900 |
| 1 | $H_2N$–CH$_2$CH$_2$–C(O)– | $C_{32}H_{49}N_4O_4^+$ | 553.3748 | 553.3750 |
| 1 | CH$_3$CH$_2$–C(O)– | $C_{32}H_{48}N_3O_4^+$ | 538.3639 | 538.3640 |
| 1 | $H_2N$–CH=CH–C(O)– | $C_{32}H_{47}N_4O_4^+$ | 551.3592 | 551.3591 |
| 2 | HO–CH$_2$CH$_2$–C(O)– | $C_{32}H_{46}N_3O_5^+$ | 552.3432 | 552.3433 |
| 1 | HO–CH$_2$CH$_2$–C(O)– | $C_{32}H_{48}N_3O_5^+$ | 554.3588 | 554.3903 |

TABLE 3-continued
HRMS data for representative compounds of formula (I)
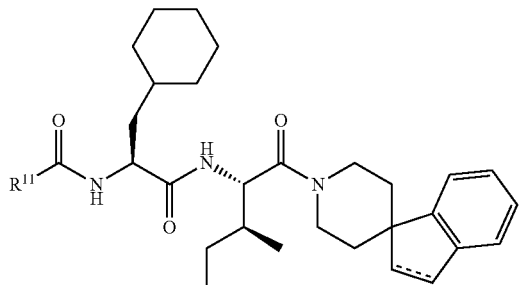
n = 1, single bond
n = 2, double bond
| n | R[11] | Formula for [M + H]+ | HRMS* Calc. | Found |
|---|---|---|---|---|
| 2 | H2N–⁙ | $C_{29}H_{43}N_4O_3^+$ | 495.3330 | 495.3334 |
| 2 | HO–CH2CH2–NH–⁙ | $C_{31}H_{47}N_4O_4^+$ | 539.3592 | 539.3592 |
| 2 | PhCH2–NH–⁙ | $C_{36}H_{49}N_4O_3^+$ | 585.3799 | 585.3799 |
| 2 | H2N–CH(CH2NH2)–⁙ | $C_{31}H_{48}N_5O_3^+$ | 538.3752 | 538.3752 |
| 2 | 2-iminoimidazolidinyl | $C_{32}H_{47}N_6O_3^+$ | 563.3704 | 563.3704 |
| 2 | H2N–CH(CH2C(O)NH2)–⁙ | $C_{32}H_{48}N_5O_4^+$ | 566.3701 | 566.3701 |
| 2 | 3-amino-isoxazol-5-yl | $C_{32}H_{44}N_5O_4^+$ | 562.3388 | 562.3388 |

TABLE 3-continued

HRMS data for representative compounds of formula (I)

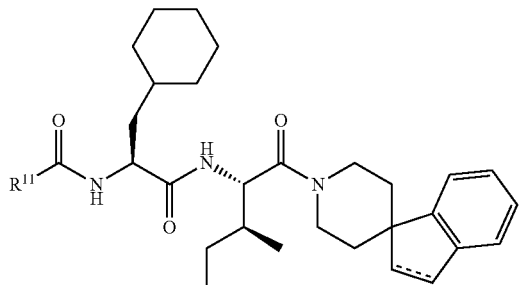

n = 1, single bond
n = 2, double bond

| n | R[11] | Formula for [M + H]+ | HRMS* Calc. | Found |
|---|---|---|---|---|
| 2 | ![tBuO-] | $C_{33}H_{50}N_3O_4^+$ | 552.3796 | 552.3796 |

*Note:
molecular ion for [M + H]+ unless indicated otherwise

TABLE 4

HRMS data for representative compounds of formula (I)

| Structure | Formula for [M + H]+ | HRMS* Calc. | Found |
|---|---|---|---|
| (morpholine-cyclohexyl-spiroindene structure) | $C_{32}H_{48}N_3O_3^+$ | 522.3690 | 522.3693 |
| (isoxazole-dicyclohexyl-spiroindene structure) | $C_{35}H_{47}N_4O_4^+$ | 587.3592 | 587.3588 |

TABLE 4-continued

HRMS data for representative compounds of formula (I)

| Structure | Formula for [M + H]+ | HRMS* Calc. | Found |
|---|---|---|---|
| 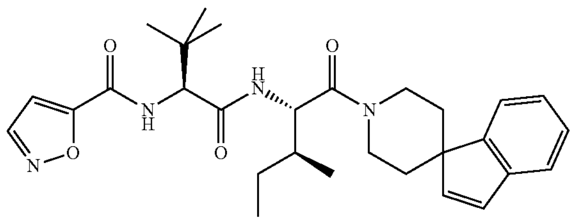 [SMILES: CC[C@H](C)[C@H](NC(=O)[C@@H](NC(=O)c1ccno1)C(C)(C)C)C(=O)N1CCC2(C=Cc3ccccc32)CC1] | C29H39N4O4+ | 507.2966 | 507.2965 |
| 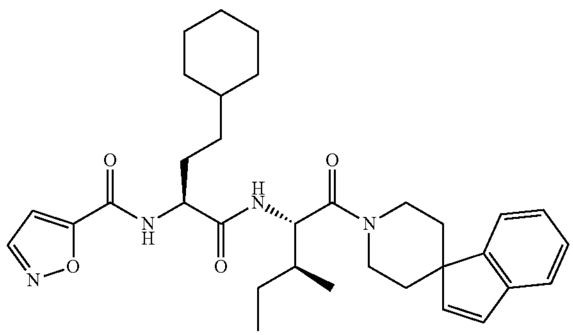 [SMILES: CC[C@H](C)[C@H](NC(=O)[C@H](CCC1CCCCC1)NC(=O)c1ccno1)C(=O)N1CCC2(C=Cc3ccccc32)CC1] | C33H45N4O4+ | 561.3435 | 561.3438 |
| 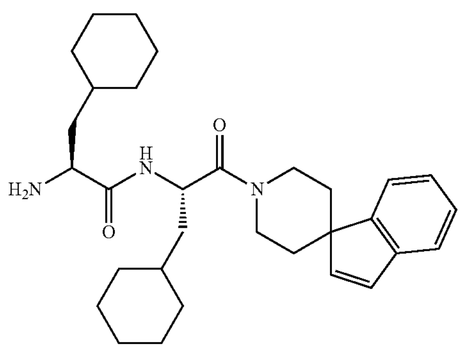 [SMILES: N[C@@H](CC1CCCCC1)C(=O)N[C@@H](CC1CCCCC1)C(=O)N1CCC2(C=Cc3ccccc32)CC1] | C31H46N3O2+ | 492.3585 | 492.3590 |
| 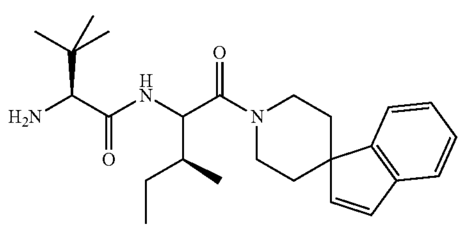 [SMILES: CC[C@H](C)C(NC(=O)[C@@H](N)C(C)(C)C)C(=O)N1CCC2(C=Cc3ccccc32)CC1] | C25H38N3O2+ | 412.2959 | 412.2958 |
| 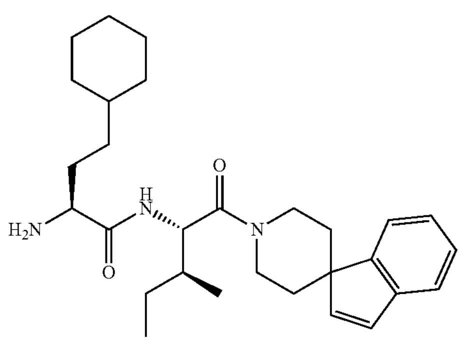 [SMILES: CC[C@H](C)[C@H](NC(=O)[C@@H](N)CCC1CCCCC1)C(=O)N1CCC2(C=Cc3ccccc32)CC1] | C29H44N3O2+ | 466.3428 | 466.3432 |

TABLE 4-continued

HRMS data for representative compounds of formula (I)

| Structure | Formula for [M + H]+ | HRMS* Calc. | Found |
|---|---|---|---|
|  | $C_{27}H_{39}N_3Na_1O_3^+$ [M + Na]+ | 476.2884 | 476.2879 |
|  | $C_{30}H_{40}N_3O_4^+$ | 506.3013 | 506.3014 |
|  | $C_{28}H_{43}N_4O_4^+$ | 499.3279 | 499.3281 |
|  | $C_{25}H_{38}N_3O_2^+$ | 412.2964 | 412.2961 |
|  | $C_{30}H_{40}N_5O_5^+$ | 550.3024 | 550.3019 |

TABLE 4-continued

HRMS data for representative compounds of formula (I)

| Structure | Formula for [M + H]+ | Calc. | Found |
|---|---|---|---|
| | C₂₆H₃₇N₄O₆⁺ | 501.2708 | 501.2708 |
| | C₃₁H₄₁N₄O₅⁺ | 549.3071 | 549.3076 |
| | C₃₀H₄₀N₅O₄⁺ | 534.3075 | 534.3070 |
| | C₃₂H₃₉N₆O₄⁺ | 571.3027 | 571.3026 |

TABLE 4-continued

HRMS data for representative compounds of formula (I)

| Structure | Formula for [M + H]+ | HRMS* Calc. | Found |
|---|---|---|---|
| 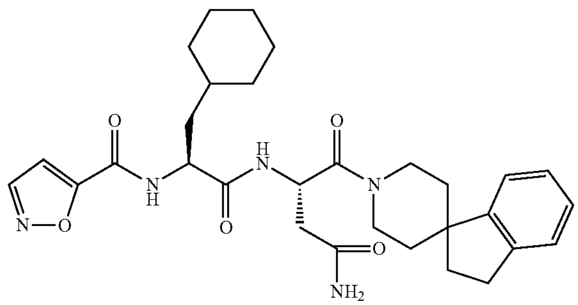 [SMILES: NC(=O)C[C@H](NC(=O)[C@H](CC1CCCCC1)NC(=O)c1ccno1)C(=O)N1CCC2(CCc3ccccc32)CC1] | $C_{30}H_{40}N_5O_5^+$ | 550.3024 | 550.3007 |
| 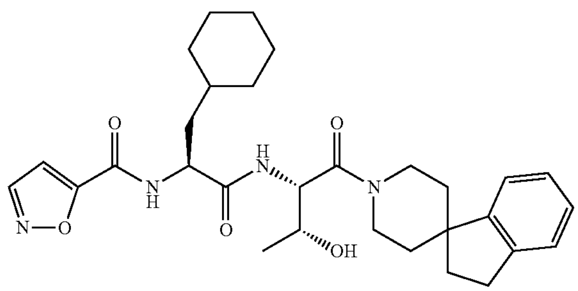 [SMILES: C[C@@H](O)[C@H](NC(=O)[C@H](CC1CCCCC1)NC(=O)c1ccno1)C(=O)N1CCC2(CCc3ccccc32)CC1] | $C_{30}H_{39}N_4O_5^+$ | 535.2915 | 535.2915 |
| 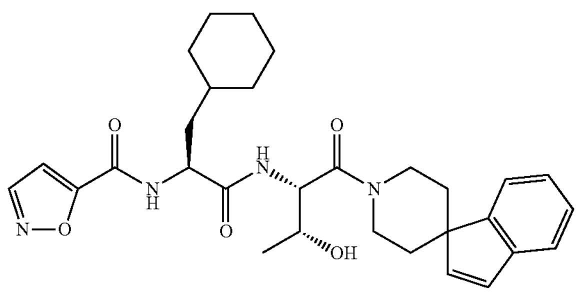 [SMILES: C[C@@H](O)[C@H](NC(=O)[C@H](CC1CCCCC1)NC(=O)c1ccno1)C(=O)N1CCC2(C=Cc3ccccc32)CC1] | $C_{30}H_{41}N_4O_5^+$ | 537.3071 | 537.3071 |
| 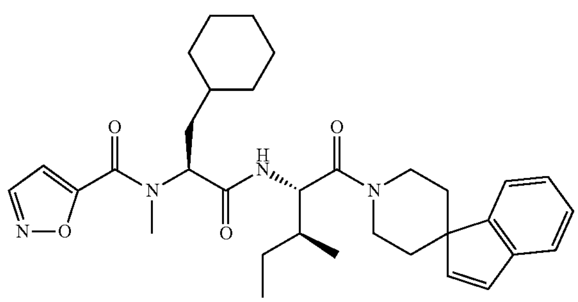 [SMILES: CC[C@H](C)[C@H](NC(=O)[C@H](CC1CCCCC1)N(C)C(=O)c1ccno1)C(=O)N1CCC2(C=Cc3ccccc32)CC1] | $C_{33}H_{45}N_4O_4^+$ | 561.3435 | 561.3435 |
| 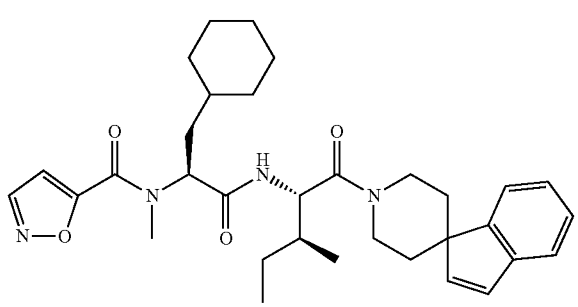 [SMILES: CC[C@H](C)[C@H](NC(=O)[C@H](CC1CCCCC1)N(C)C(=O)c1ccno1)C(=O)N1CCC2(C=Cc3ccccc32)CC1] | $C_{33}H_{44}N_4NaO_4^+$ [M + Na]+ | 583.3255 | 583.3250 |

TABLE 4-continued

HRMS data for representative compounds of formula (I)

| Structure | Formula for [M + H]$^+$ | HRMS* Calc. | Found |
|---|---|---|---|
| | $C_{33}H_{45}N_4O_4{}^+$ | 561.3435 | 561.3435 |
| | $C_{34}H_{49}N_5Na_1O_5{}^+$ [M + Na]$^+$ | 630.3631 | 630.3809 |
| | $C_{33}H_{51}N_6O_6{}^+$ | 627.3865 | 627.3863 |
| | $C_{28}H_{42}N_3O_2{}^+$ | 452.3272 | 452.3274 |
| | $C_{29}H_{44}N_3O_2{}^+$ | 466.3428 | 466.3424 |

TABLE 4-continued

HRMS data for representative compounds of formula (I)

| Structure | Formula for [M + H]⁺ | HRMS* Calc. | Found |
|---|---|---|---|
| 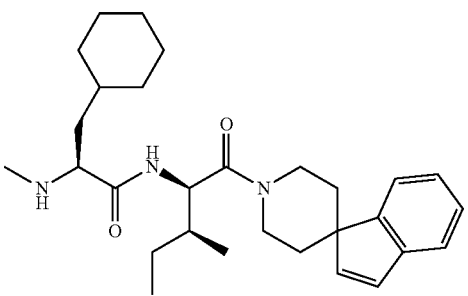 [SMILES: CC[C@H](C)[C@@H](NC(=O)[C@H](CC1CCCCC1)NC)C(=O)N1CCC2(C=Cc3ccccc32)CC1] | $C_{29}H_{44}N_3O_2^+$ | 466.3428 | 466.3428 |
| 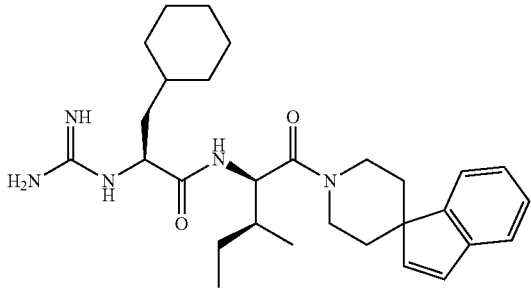 [SMILES: CC[C@H](C)[C@@H](NC(=O)[C@H](CC1CCCCC1)NC(=N)N)C(=O)N1CCC2(C=Cc3ccccc32)CC1] | $C_{29}H_{44}N_5O_2^+$ | 494.3490 | 494.3489 |
| 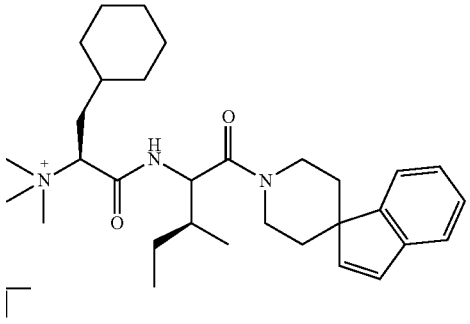 | $C_{31}H_{48}N_3O_2^+$ (cation alone) | 494.3741 | 494.3741 |

*Note:
molecular ion for [M + H]⁺ unless indicated otherwise

Example 12

Determination of PAR2 Activation

The ability of the compounds of the present invention to activate PAR2 may be assessed via calcium mobilisation assays. It is appreciated that compounds that activate the release of intracellular calcium from one type of cell are agonists or partial agonists, while those that inhibit such release may be antagonists. However these "agonist" and "antagonist" effects may be reversed for a given compound or PAR2 ligand in a different cell, or opposite responses may be observed using a different reported assay (e.g. ERK phosphorylation or cAMP stimulation. All cell culture reagents used for these assays are purchased from Invitrogen (Carlsbad, Calif.) and Sigma Aldrich (St. Louis, Mo.). Cell lines are cultured in medium at 37° C. and 5% $CO_2$ based on information provided by ATCC (Manassas, Va.). Cell lines that may be used for these experiments include but are not limited to the human cell lines HT29, HEK293, MM96L, Saos-2, MG-63, HeLa, JAM, A549 and HOP62. The general assay protocols may vary slightly depending on the chosen cell line. In general, during cell culture passage, cell dissociation solution (CDS, Sigma Aldrich) is used to replace trypsin to dissociate cells from surface. Lipopolysaccharide (LPS) and trypsin are purchased from Sigma Aldrich. Trichostatin (TSA) and PAR2 activating peptide, 2f-LI-GRLO-$NH_2$, are synthesized in-house. ELISA sets are purchased from BD Pharmingen (San Jose, Calif.) and cytokine array kits are purchased from RayBiotecho (Norcross, Ga.). Anti-PAR antibody is purchased from Santa Cruz Biotechnology (Santa Cruz, Calif.) and anti-goat antibody conjugated with Alexa-Fluor 488 is purchased from Invitrogen.

Cells are seeded overnight in 96-well black walled, clear bottomed, plate at approximately $2\times10^4$ to $4\times10^5$ cells per well. On the day of the experiment, the supernatant is removed and the cells are incubated in dye-loading buffer (Hank's Balanced Salt Solution (HBSS) with 4 μM to 2 mM Fluo-3 AM, 25 μL plutonic acid, 1% fetal bovine serum (PBS), 2.5 mM probenecid and 20 mM HEPES) for one hour at 37° C. The cells are then washed twice with HBSS and transferred to a Polarstar spectrofluorimeter (BMG, Durham N.C.).

To determine agonist activity, the compounds of the present invention are added to the individual wells 10 s after reading commences at various concentrations and fluorescence is measured in real time from the bottom of the plate at an excitation wavelength of 480 nm or 495 nm and emission wavelength of 520 nm. HBSS is prepared in-house and all other reagents are purchased from Invitrogen, Carlsbad. Plates are supplied by DKSH, Zurich. Calcimycin (A23187, Invitrogen) is used to measure maximum fluorescence, with individual results normalized accordingly.

Results of exemplified compounds of the general formula (I) are shown below in Tables 5 and 6. Additionally, a graphical representation of the above mentioned agonist assays for the PAR2 agonist 6 is shown in FIG. 1 and described below.

Three different concentrations of 6 added to HT29 cells at room temperature. Duplicate measurements were made for each data point, accordingly, each data point represents mean±SEM. Net changes in fluorescence were calculated as a percentage relative to the maximum response given by 100 μM of the PAR2 agonist 2f-LIGRLO-NH$_2$. At 30 μM, 6 was giving up to 50% response, indicating that the EC$_{50}$ of 6 is approximately 30 μM.

TABLE 5

Biological Activity for representative PAR2 Ligands as Agonists or Partial Agonists of Ca$^{2+}$ release in HT29 cells.

| Compound No. | R | EC$_{50}$ (μM) |
|---|---|---|
| 1 | [structure: -NH-CH$_2$-phenyl-C(O)-NH-CH(CONH$_2$)-CH$_2$CH$_2$CH$_2$-NH$_2$] | 0.2 |
| 2 | [structure: -NH-CH$_2$-phenyl-C(O)-NH-CH(CONH$_2$)-CH$_2$CH$_2$-NH$_2$] | 0.2 |
| 3 | [structure: -NH-CH$_2$-phenyl] | 30 |
| 4 | [structure: -NH-CH$_2$-phenyl-OMe (para)] | 10 |
| 5 | [structure: -NH-CH$_2$-phenyl-Cl (ortho)] | 10 |

TABLE 5-continued
Biological Activity for representative PAR2 Ligands as Agonists or Partial Agonists of Ca$^{2+}$ release in HT29 cells.
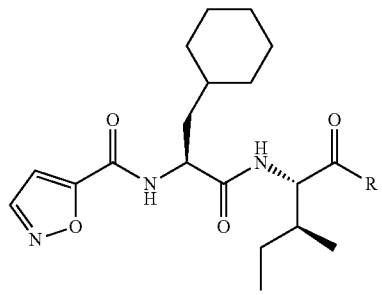
| Compound No. | R | EC$_{50}$ (μM) |
|---|---|---|
| 6 | 2-F-benzylamine | 30 |
| 7 | 3-F-benzylamine | 40 |
| 8 | 4-F-benzylamine | 40 |
| 9 | 2-NO$_2$-benzylamine | 10 |
| 10 | 4-(4-fluorophenyl)piperazine | 10 |
| 11 | 6,7-dimethoxy-1,2,3,4-tetrahydroisoquinoline | 5-10 |
| 12 | 4-phenyl-4-acetamidopiperidine | 1-6 |

TABLE 6.

Biological Activity for representative PAR2 Ligands as Agonists or Partial Agonists of $Ca^{2+}$ release in HT29 cells.

| | | |
|---|---|---|
| | [structure: isoxazole-C(O)-NH-CH(CH2-cyclohexyl)-C(O)-NH-CH(CH(CH3)CH2CH3)-C(O)-R] | |
| 13 | [structure: spiro piperidine-indoline with N-SO2Me] | 1.8 |
| 14 | [structure: spiro piperidine-isobenzofuranone] | 1.3 |
| 15 | [structure: spiro piperidine-chromanone] | 0.76 |
| 16 | [structure: spiro piperidine-indane-diol] | 5-7 |
| 17 | [structure: spiro piperidine-indane with OH and NH-CH2-C6H4-F] | 20 |

Example 13

Determination of PAR2 Agonist Inhibition (Antagonism)

The ability of compounds of the present invention to inhibit the activation of PAR2 by trypsin or a synthetic PAR2 agonist is determined by intracellular calcium release assays as described above for Example 12.

The cells are prepared as outlined above then treated with the 'putative' antagonist 30 min prior to the addition of either trypsin or a synthetic agonist at a concentration equal to the agonists $EC_{80}$. The ability of compounds of the present invention to inhibit the activation of PAR2 is exemplified below in Tables 7, 8 and 9. Additionally, graphical representations of the above mentioned antagonist assays for the PAR2 antagonists represented by the synthetic examples (18, 24, 26, 27, 30, 39 and 42) are shown in FIGS. 2 to 8 and explained in detail below.

PAR2 Ligand 18.

Figure 2:
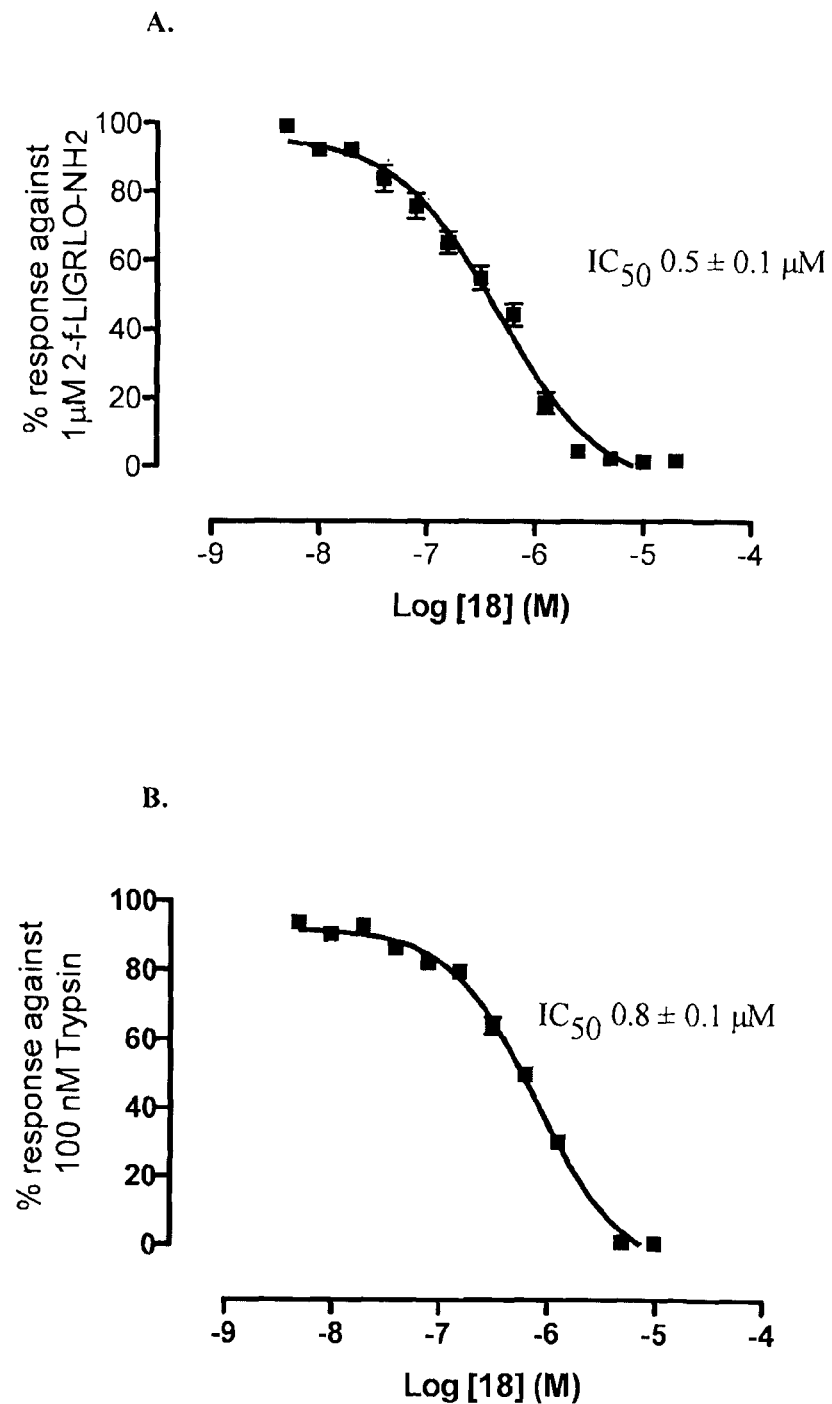
FIG. 2: Graphical representation of the concentration dependent inhibition of intracellular $Ca^{2+}$ release in HT29 cells by the PAR2 antagonist 18.

A graphical representation of the inhibition of intracellular $Ca^{2+}$ release in HT29 cells by PAR2 antagonist 18 is shown in FIG. 2. Compound 18 was pre-incubated with HT29 cells for 30 min at room temperature prior to the experiment. The cells were then treated with 1 μM of the PAR2 agonist 2f-LIGRLO-NH$_2$ (FIG. 2A, n=5) or 100 nM Trypsin (FIG. 2B, n=1). Each data point represents mean±SEM. Net changes in fluorescence were calculated as a percentage relative to the maximum response given 1 μM 2f-LIGRLO-NH$_2$ or 100 nM Trypsin. Changes in fluorescence (% response) were plotted against logarithmic compound concentrations. The half maximal inhibitory concentration ($IC_{50}$) values were derived from the dose response curve using a nonlinear regression curve in Graphpad Prism v5.

PAR2 Ligand 24.

Figure 3:
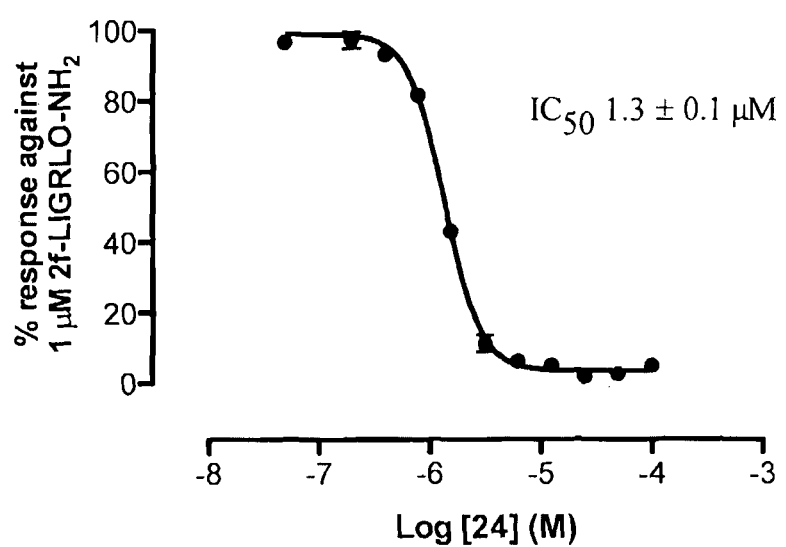
FIG. 3: Graphical representation of the concentration dependent inhibition of intracellular $Ca^{2+}$ release in HT29 cells by the PAR2 antagonist 24.

A graphical representation of the inhibition of intracellular $Ca^{2+}$ release in HT29 cells by PAR2 antagonist 24 is shown in FIG. 3 (n=1). Compound 24 was pre-incubated with HT29 cells 30 min at room temperature prior to the experiment. The cells were then treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration ($IC_{50}$) values were derived from the dose response curve using a nonlinear regression curve in Graphpad Prism.v5.

PAR2 Ligand 26.

Figure 4:
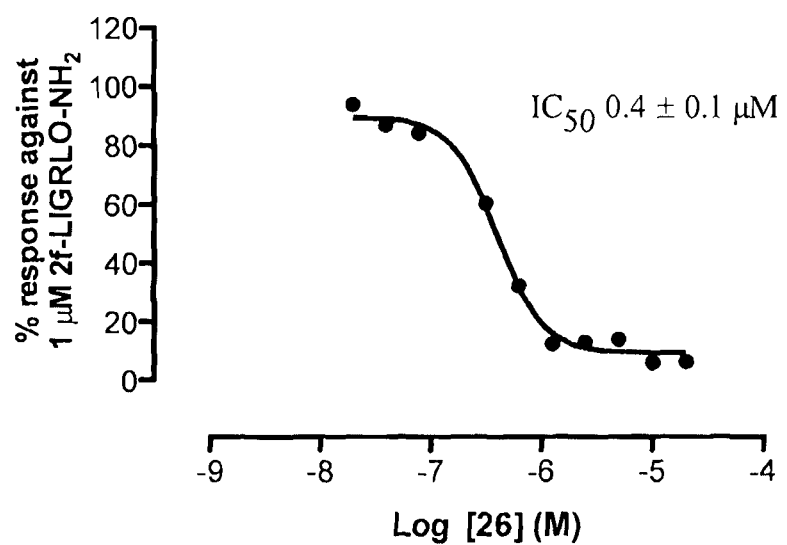
FIG. 4: Graphical representation of the concentration dependent inhibition of intracellular $Ca^{2+}$ release in HT29 cells by the PAR2 antagonist 26.

A graphical representation of the inhibition of intracellular $Ca^{2+}$ release in HT29 cells by PAR2 antagonist 26 is shown in FIG. 4 (n=1). Compound 26 was pre-incubated with HT29 cells 30 min at room temperature prior to the experiment. The cells were then treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration ($IC_{50}$) values were derived from the dose response curve using a nonlinear regression curve in Graphpad Prism v5.

PAR2 Ligand 27.

Figure 5:
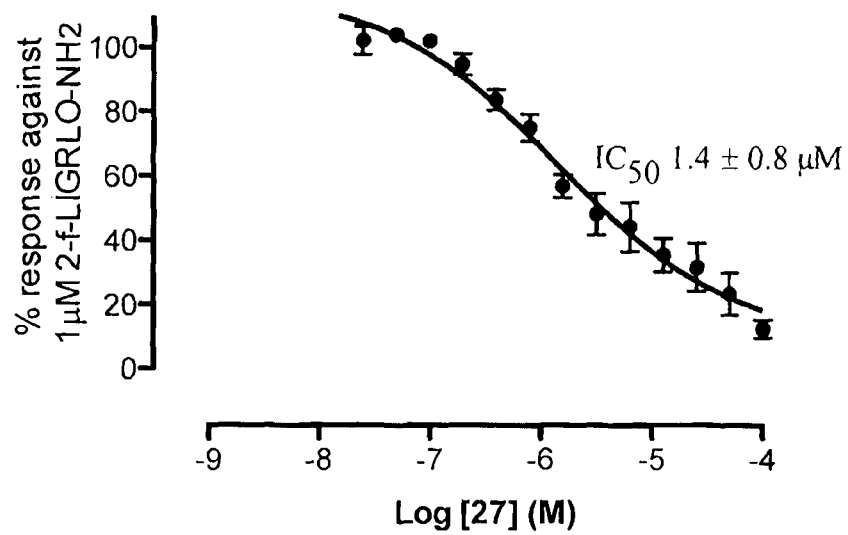
FIG. 5: Graphical representation of the concentration dependent inhibition of intracellular $Ca^{2+}$ release in HT29 cells by the PAR2 antagonist 27.

A graphical representation of the inhibition of intracellular $Ca^{2+}$ release in HT29 cells by PAR2 antagonist 27 is shown in FIG. 5 (n=2). Compound 27 was pre-incubated with HT29 cells 30 min at room temperature prior to the experiment. The cells were then treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration (IC$_{50}$) values were derived from the dose response curve using a nonlinear regression curve in Graphpad Prism v5.

PAR2 Ligand 30.

Figure 6:
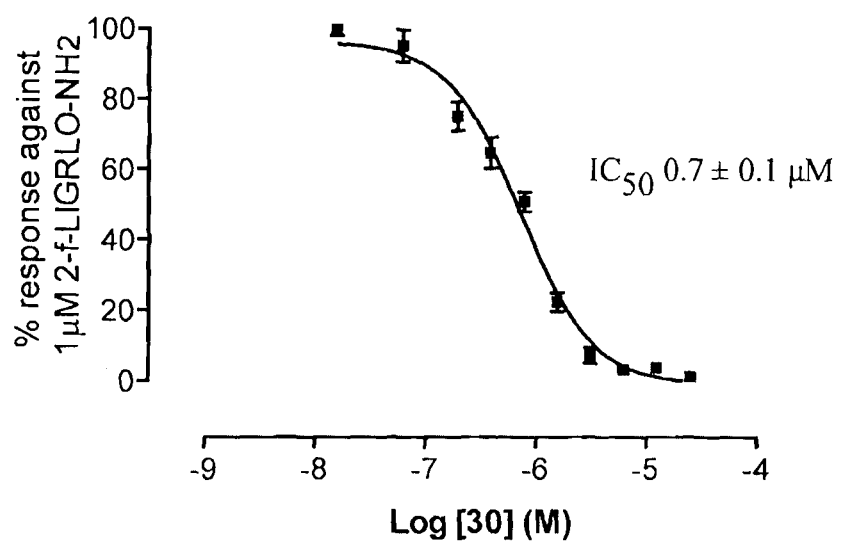
FIG. 6: Graphical representation of the concentration dependent inhibition of intracellular $Ca^{2+}$ release in HT29 cells by the PAR2 antagonist 30.

A graphical representation of the inhibition of intracellular Ca$^{2+}$ release in HT29 cells by PAR2 antagonist 30 is shown in FIG. 6 (n=8). Compound 30 was pre-incubated with HT29 cells 30 min at room temperature prior to the experiment. The cells were than treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration (IC$_{50}$) values were derived from the dose response curve using a nonlinear regression curve in Graphpad Prism v5.

PAR2 Ligand 39.

Figure 7:
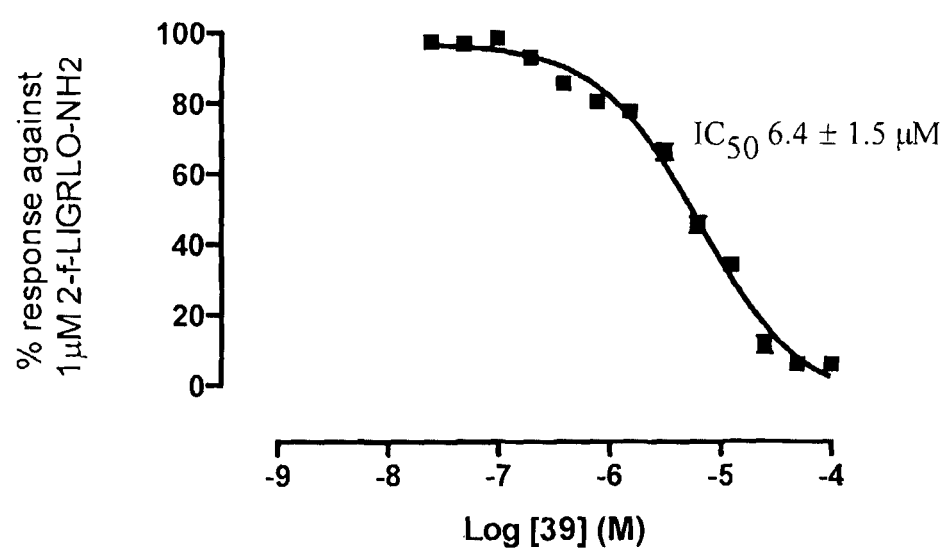
FIG. 7: Graphical representation of the concentration dependent inhibition of intracellular $Ca^{2+}$ release in HT29 cells by the PAR2 antagonist 39.

A graphical representation of the inhibition of intracellular Ca$^{2+}$ release in HT29 cells by PAR2 antagonist 39 is shown in FIG. 7 (n=1). Compound 39 was pre-incubated with HT29 cells 30 min at room temperature prior to the experiment. The cells were then treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration (IC$_{50}$) values were derived from the dose response curve using a nonlinear regression curve in Graphpad Prism v5.

PAR2 Antagonist 42.

Figure 8:
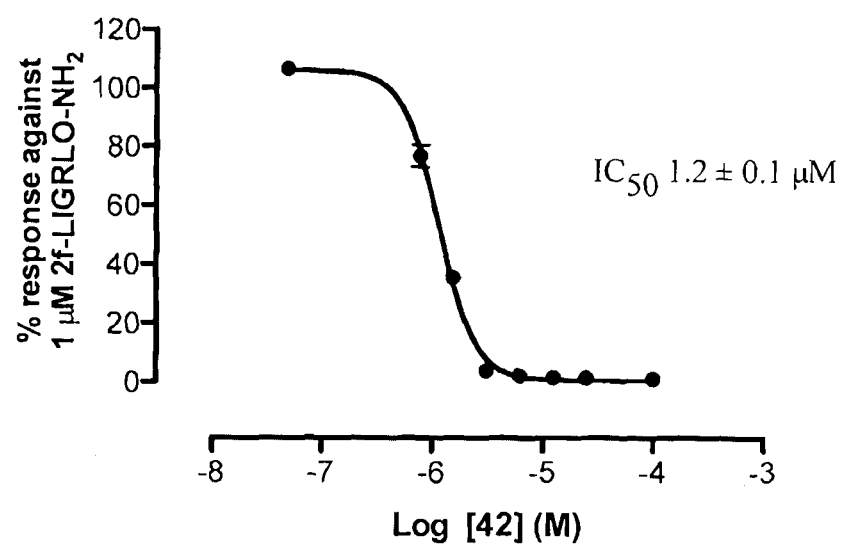
FIG. 8: Graphical representation of the concentration dependent inhibition of intracellular $Ca^{2+}$ release in HT29 cells by the PAR2 antagonist 42.

A graphical representation of the inhibition of intracellular Ca$^{2+}$ release in HT29 cells by PAR2 antagonist 42 is shown in FIG. 8 (n=1). Compound 42 was pre-incubated with HT29 cells 30 min at room temperature prior to the experiment. The cells were then treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration (IC$_{50}$) values were derived from the dose response curve using a nonlinear regression curve in Graphpad Prism v5.

TABLE 7

Benzylamine ligands that can Antagonise PAR2 Activation as Measured by Inhibiting Ca$^{2+}$ Release in HT29 cells.

| Compound No. | R | IC$_{50}$ (μM) |
|---|---|---|
| 18 | 2-OMe-benzyl | 0.5 ± 0.1 |
| 19 | 3-OMe-benzyl | 0.5 ± 0.1 |
| 20 | 2-Me-benzyl | 0.5 ± 0.1 |

TABLE 7-continued

Benzylamine ligands that can Antagonise PAR2 Activation as Measured by Inhibiting $Ca^{2+}$ Release in HT29 cells.

| Compound No. | R | $IC_{50}$ (μM) |
|---|---|---|
| 21 | 2-OEt-benzyl | 0.7 ± 0.1 |
| 22 | 2-OPr-benzyl | 2.0 |
| 23 | 2-OBu-benzyl | 40 |
| 24 | 2-OiPr-benzyl | 1.3 ± 0.1 |
| 25 | 2-OsBu-benzyl | 1.6 ± 0.4 |
| 26 | benzo[1,3]dioxol-4-ylmethyl | 0.4 ± 0.1 |
| 27 | 3,4-dichlorobenzyl | 1.4 ± 0.8 |

TABLE 7-continued

Benzylamine ligands that can Antagonise PAR2 Activation as Measured by Inhibiting Ca$^{2+}$ Release in HT29 cells.

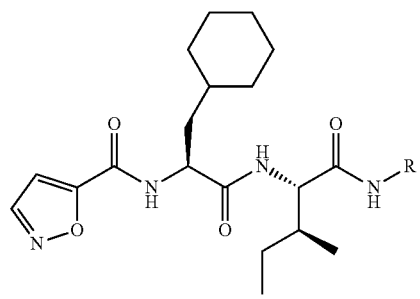

| Compound No. | R | IC$_{50}$ (μM) |
|---|---|---|
| 28 | (2-CF$_3$-benzyl) | 1-2 |
| 29 | (3-substituted benzyl with piperidine) | 0.7 |

TABLE 8.

Representative Piperidine Ligands that can Antagonise of PAR2 Activation as Measured by Inhibiting Ca$^{2+}$ Release in HT29 Cells.

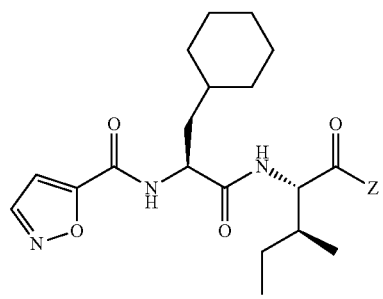

| Compound No. | Z | IC$_{50}$ (μM) |
|---|---|---|
| 30 | 4-phenylpiperidinyl | 0.7 ± 0.1 |

TABLE 8.-continued

Representative Piperidine Ligands that can Antagonise of PAR2 Activation as Measured by Inhibiting Ca$^{2+}$ Release in HT29 Cells.

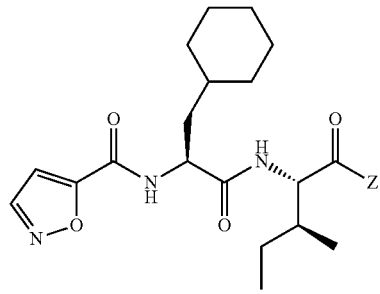

| Compound No. | Z | IC$_{50}$ (μM) |
|---|---|---|
| 31 | 4-(4-methoxyphenyl)piperidinyl | 10 |

TABLE 8.-continued

Representative Piperidine Ligands that can Antagonise of PAR2 Activation as Measured by Inhibiting Ca$^{2+}$ Release in HT29 Cells.

| Compound No. | Z | IC$_{50}$ (μM) |
|---|---|---|
| 32 | 4-(2,5-dimethoxyphenyl)piperidin-1-yl | 5-10 |
| 33 | 4-(2-trifluoromethylphenyl)piperidin-1-yl | 10 |
| 34 | 4-(2-biphenyl)piperidin-1-yl | 25 |
| 35 | 4-benzylpiperidin-1-yl | 8 |
| 36 | 2-(tert-butylcarbamoyl)piperidin-1-yl | 8.6 ± 2.6 |
| 37 | 1'-methylspiro[chroman-2,4'-piperidine] | 5-10 |
| 38 | 3-((3-trifluoromethylphenyl)amino)piperidin-1-yl | 6 |

US 9,868,763 B2

TABLE 9

Other Representative PAR2 Ligands that can Antagonise PAR2 Activation as Measured by Inhibiting $Ca^{2+}$ Release in HT29 Cells.

| Compound No. | R[1] | X | Y | R5 | Z | $IC_{50}$ (μM) |
|---|---|---|---|---|---|---|
| 39 | isoxazol-5-yl-C(O)- | $CH_2$ | H | Et | N-methyl-N-(2-methoxybenzyl)amino | 6.4 |
| 40 | isoxazol-5-yl-C(O)- | $CH_2$ | H | OMe | N-(2-methoxybenzyl)amino | 1.3 |
| 41 | H | $CH_2$ | H | Et | spiro[indene-piperidine]-N-yl | 17 |
| 42 | 3-amino-isoxazol-5-yl-C(O)- | $CH_2$ | H | Et | spiro[indene-piperidine]-N-yl | 1.2 |
| 43 | isoxazol-5-yl-C(O)- | O | H | Et | spiro[indene-piperidine]-N-yl | 60 |
| 44 | isoxazol-5-yl-C(O)- | $CH_2$ | H | OMe | spiro[indene-piperidine]-N-yl | 1 |
| 45 | 1H-1,2,4-triazol-3-yl-C(O)- | $CH_2$ | H | Et | spiro[indene-piperidine]-N-yl | 15 |

TABLE 9-continued

Other Representative PAR2 Ligands that can Antagonise PAR2 Activation as Measured by Inhibiting $Ca^{2+}$ Release in HT29 Cells.

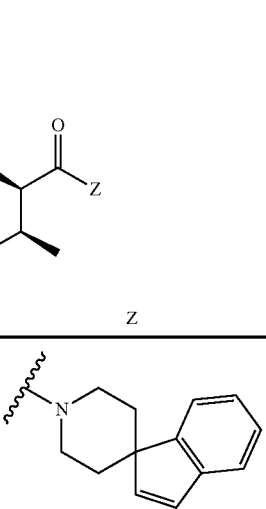

| Compound No. | R¹ | X | Y | R5 | Z | IC$_{50}$ (μM) |
|---|---|---|---|---|---|---|
| 46 | 5-methylisoxazol-3-yl-C(O)- | CH$_2$ | H | Et | spiro[indene-piperidine]-N- | 25 |
| 47 | imidazol-5-yl-C(O)- | CH$_2$ | H | Et | spiro[indene-piperidine]-N- | 10 |
| 48 | piperidin-4-yl-C(O)- | CH$_2$ | H | Et | spiro[indene-piperidine]-N- | 50 |
| 49 | 5-oxopyrrolidin-2-yl-C(O)- | CH$_2$ | H | Et | spiro[indene-piperidine]-N- | 25 |
| 50 | pyrrolidin-2-yl-C(O)- | CH$_2$ | H | Et | spiro[indene-piperidine]-N- | 50 |
| 51 | H | CH$_2$ | Me | Et | spiro[indene-piperidine]-N- | 5-10 |
| 52 | isoxazol-5-yl-C(O)- | CH$_2$ | H | Et | spiro[indene-piperidine]-N- | 1 |

TABLE 9-continued

Other Representative PAR2 Ligands that can Antagonise PAR2 Activation as Measured by Inhibiting $Ca^{2+}$ Release in HT29 Cells.

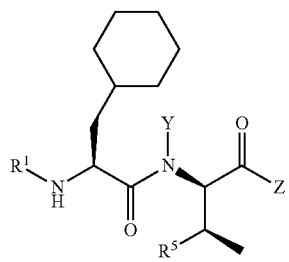

| Compound No. | $R^1$ | X | Y | R5 | Z | $IC_{50}$ (µM) |
|---|---|---|---|---|---|---|
| 53 | (isoxazol-5-yl-carbonyl) | O | $CH_2$ | H | Et | (spiro[indane-1,4'-piperidine]) | 3 |

Example 14

Assessment of the Anti-Inflammatory Activity of the Compounds of the Present Invention The ability of compounds of the present invention to ameliorate the symptoms associated with both acute and chronic inflammatory disorders may be determined via a number of animal models well known to those skilled in the art, general examples of which are provided below.

Pharmacokinetics

Animals

Male and female Wistar rats (aged 8-9 weeks, 200-250 g and 250-300 g respectively) are generally maintained in a 12 h light/dark cycle according to the standard of holding facility with food and water provided.

Short Term Pharmacokinetics

Male Wistar rats are surgically implanted with a jugular vein catheter. Volumes of blood are collected from the indwelling catheter in freely moving animals. Blood samples (heparinised) are collected 5 minutes prior to the administration of a compound of the present invention (10 mg/kg p.o.) and 30 min, 1-6, 8 and 24 h post-administration. Bloods are centrifuged at 8 K rpm for 5 min, and plasma diluted 3 times (v/v) with acetonitrile and stored at −80° C. for later use.

Long-Term Pharmacokinetics

A subset of animals not implanted with a catheter are given an oral dose of a compound of the present invention four days consecutively (n=6). On the fifth day, rats are euthanised ($CO_2$ inhalation) and plasma is collected via cardiac puncture. Cerebrospinal fluid (CSF) is collected from the cisterna magna and intraperitoneal adipose is collected. Clean and blood free CSF samples are diluted twice in acetonitrile, vortexed and centrifuged at 8 K rpm for 5 min. Adipose is homogenised in equal volume (mL/g) Millipore water. A portion of the sample is diluted in acetonitrile (3×w/v) and stored at −80° C. for later use.

Preparation of Fluid Samples

Standard curve: each stock solution comprising a compound of the present invention is prepared in acetonitrile at 9.15, 4.57, 0.92, 0.46, 0.09, 0.046, 0.009 and 0.005 µM. A 200 µL sample of fresh plasma from non-drug treated rat is transferred into 200 µL of stock solution, followed by addition of 400 µL of acetonitrile. The mixture is vortexed for 1 min, sonicated for 10 min centrifuged at 13 K rpm for 5 min and stored at −80° C. for later use.

Supernatants are diluted in Millipore water (3×volume) and tert-butyl methyl ether (TBME, CHROMASOLV® Plus, for HPLC, 99.9%, from Sigma Aldrich, 3×volume). Samples are vortexed and left on dry ice until the water/acetonitrile phase is frozen. The organic phase is decanted into a microfuge tube and concentrated using a rotational vacuum concentrator (Christ Beta-RVC, supplied by Quantum Scientific). 100 µL of acetonitrile is added to the residue, vortexed and immediately analysed by LCMS/MS.

Acute Inflammatory Model: PAR2-Induced Paw Oedema

Figure 9:
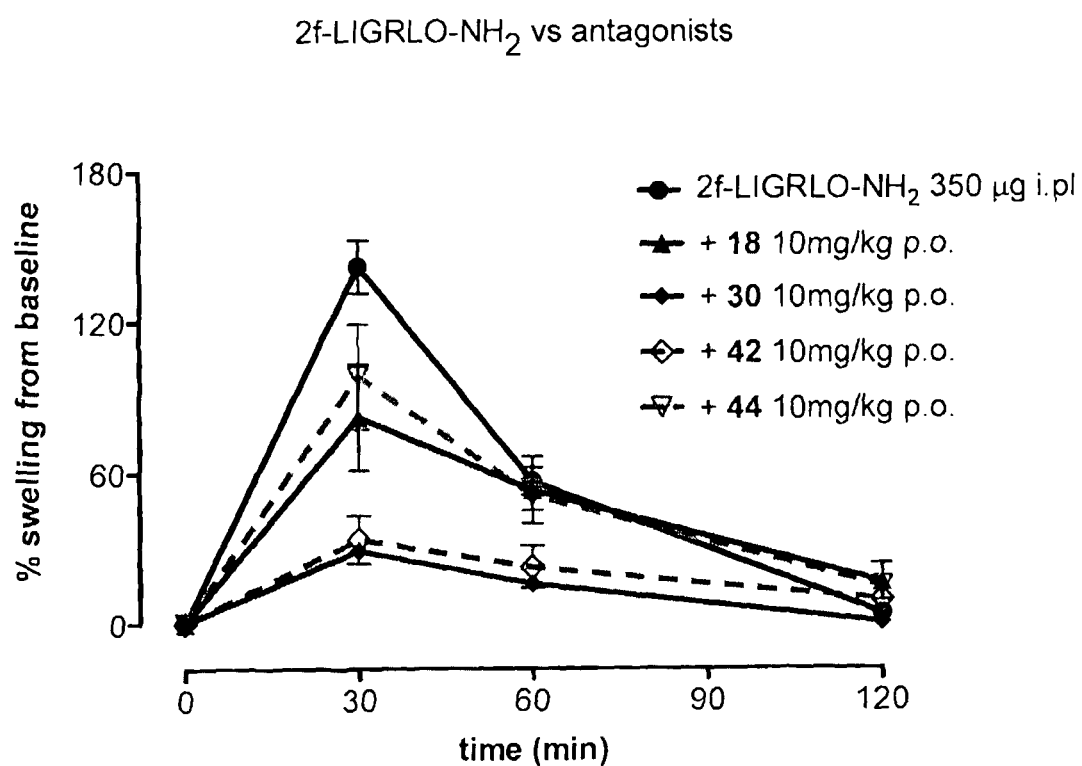
FIG. 9. Graphical representation of the ability of PAR2 antagonists 18, 30, 42, 44 to attenuate experimental paw oedema. Antagonist 18, 30, 42 or 44 (10 mg/kg p.o. in olive oil, n=3) reduced the paw swelling induced by 2-f-LIGRLO-NH$_2$ (350 µg/paw, 2 h after oral dose of the antagonist).

The methods used are based on those previously described (Kelso, E. B., et al. *Arthritis Rheum* 2007, 56, 765-71; Kelso, E. B., et al. *J Pharmacol Exp Ther* 2006, 316, 1017-24; and Vergnolle, N. *J Immunol* 1999, 163, 5064-9). Male Wistar rats (n=3 per group) are used. Briefly, rats are given either 5 or 10 mg/kg of a compound of the present invention (p.o. via gavage in olive oil, approx. 500 µL, weight adjusted). Control animals receive only olive oil (500 µL p.o.). Two hours later, the PAR2 agonist 2-furoyl-LIGRLO (350 µg/paw in saline, 100 µL) is injected into the plantar surface (i.pl.) of the right paw pad using a 30 G needle. The left paw acts as a control, receiving saline only. Paw thickness and width are measured after 30 minutes and hourly using digital calipers (World Precision Instruments, USA) and swelling is calculated in area ($mm^2$; thickness multiplied by width) and expressed as a percentage change from baseline of each individual paw. Results for exemplary PAR2 ligands 18, 30, 42 and 44 are illustrated in FIG. 9.

Acute Inflammatory Model: λ-Carrageenan-Induced Paw Oedema

Methods used are based on that previously described (Kelso, E. B., et al., *J Pharmacol Exp Ther* 316:1017-1024; and Flick, M. J., et al., *J Clin Invest* 117:3224-3235). Male Wistar rats (n=4 per group) are used. Briefly, rats are given 10 mg/kg of a compound of the present invention (p.o. via gavage in olive oil, 500 μL). Control animals receive only olive oil (500 μL p.o.). Thirty minutes later, λ-carrageenan (1% w/v in saline, 100 μL) is injected into the plantar surface (i.pl.) of the right paw pad using a 30 G needle. The left paw acts as a control, receiving saline only, similar to that previously described. Paw width and thickness are measured at 1-6, 8 and 24 h. Data is expressed as a normalised change in area ($mm^2$) from baseline.

Chronic Inflammatory Model: Collagen-Induced Arthritis

Protocols are based on those previously described (Earp, J. C., et al. *Biopharm Drug Dispos* 2008; Lin, H. S., et al., *Br J Pharmacol* 2007, 150, 862-72; Nishikawa, M., et al. *Arthritis Rheum* 2003, 48, 2670-81; and Olofsson, P., et al. *Arthritis Rheum* 2003, 48, 2332-42). Female Wistar rats are used (200-250 g, n=14 total). Immunisation of collagen begins on Day 0, where 200 μg of collagen is administered in 200 μL (50:50 0.05 M acetic acid and Freund's incomplete adjuvant) subcutaneously into the base of the tail using a 30 G needle. Sham animals receive the vehicle (50:50 0.05 M acetic acid and Freund's incomplete adjuvant) with collagen omitted. Seven days later (day 7), the same treatment is given as a booster. A compound of the present invention (10 mg/kg in olive oil, 500 μL, p.o. weight adjusted) is given daily to test subjects from day 7 onwards, arthritic control and sham animals receive olive oil vehicle by gavage only. Paw measurements (as described above), body weight, clinical score and mechanical nociceptive thresholds are measured every second day from Day 10 through Day 28. Only hind paws are measured. Swelling is calculated in area ($mm^2$) and expressed as a percentage change from the baseline. A paw is considered arthritically effected when the swelling of an individual paw becomes greater than 20%, which is the maximal paw area change observed in the sham group (i.e. the growth that is expected due to the experimental time course alone).

Clinical Measurements

Clinical score is measured observationally by an expert researcher, incorporating the following constraints: Mobility: 0: No limp, full hind limb weight bearing. 1: Mild limp, reduced mobility. 2: Reduced/no weight bearing on one hind limb, reduced mobility. 3: No weight bearing on either (two) hind limb, little mobility. Inflammation; 0: No redness, no swelling, and no arthritic symptoms. 1: Mild redness and swelling. 2: Arthritic symptoms appearing (clutching of toes) moderate swelling and redness. 3: Severe swelling and redness, severe arthritic symptoms (loss of plantar reflex, clutching of toes, supination and adduction of rear paws during handling). Discomfort/pain; 0: No vocalisation, normal behaviour. 1: Mild vocalisation only. 2: Increased vocalisations and mild flinching during handling. 3: Spontaneous vocalisation during movement (no handling required for instigation). Clinical scores are expressed as a sum of the three scores multiplied by the number of paws involved (maximum total score of 18, see above).

Histopathology and Joint Health Assessment

At an end point (day 28), rats are euthanized with $CO_2$. Hind paws are skinned, amputated and placed in 4% paraformaldehyde (pH 7.4) for seven days at 4° C. Paws are decalcified for 72 h (10% HCl; 0.18% (w/v) EDTA: 0.09% (w/v) tartrate in $H_2O$) and embedded in paraffin wax for histological analysis. Sections are cut at 10 μm and stained with haematoxylin and eosin (H&E), Masson's Trichrome stain (MTC) or Alcian blue/Safrannin-O using standard protocols. The tibial/talus/calcaneal joints of at least 6 sections are imaged per animal are assessed/stain technique and scored by an expert blinded to the treatment.

H&E sections are scored using the following modified guide (Woodruff, T. M., et al, *Arthritis Rheum* 2002, 46, 2476-85) as follows. Oedema; 0: healthy tissue, no plasma cell invasion. 1: Mild plasma cell invasion into the extra-synovial space. 2: Moderate plasma cell invasion into the extra-synovial space, beginning to invade synovium. 3: Severe plasma cell invasion, appearance of rice bodies and inflammatory cells in the synovium. Synovial hyperplasia; 0: Normal tissue. 1: Mild synovial swelling. 2: Moderate synovial swelling. 3: Severe swelling and growth of synovial space. Cartilage/bone erosion; 0: Normal cartilage. 1: Mild adhesion of inflammatory cells to the articular cartilage. 2: Moderate adhesion of inflammatory cells beginning to erode the first layer of articular cartilage. 3: Severe inflammatory cell adhesion and erosion of cartilage layers, perichondrum and underlying bone. Pannus formation; 0: No pannus. 1: Pannus beginning to form. 2: Pannus entering the synovium. 3: Pannus beginning to erode cartilage/bone. Total histopathological scores are expressed as a sum of all scores (total score of 12). Collagen loss is scored qualitatively in Mason's Trichrome stained sections and according to the relative proportion of red stain (loss of Aniline blue) of the articular surface of the tibia similar to previously described. 0: no red stain on articular surface, 1: 0-25% of surface appearing red, 2: 25-50% surface appearing red, 3: >50% of articular surface stained red (maximal score of 3). Differential Alcian blue/Safrannin-O staining determined mast cell activation state, similar to that previously described. Each section is imaged at 100× in regions both superior and inferior to the tibial/talus joint. At least 6 sections are imaged per animal (>12 sections analysed/rat). Cells are counted from the images with the aid of ImageJ 1.42q software. Red cells without the presence of blue are considered inactive. Cells with the appearance of blue stain, but still with some degree of red staining, are considered active. Cells with no visible red staining (only blue) are considered degranulated.

Example 15

Assessment of the Anti-Proliferative Activity of the Compounds of the Present Invention The ability of compounds of the present invention to attenuate aberrant cellular proliferation may be determined via a number of assays well known to those skilled in the art, including, but not limited to the general example provided below.

Tritiated Thymidine Incorporation into Cellular DNA.

Primary human kidney tubule cells are grown in 48 well plates in hormonally defined serum free DMEM/F12 until 90% confluent. They are then washed twice with DMEM without added growth factors and cultured for a further for 24 h in this basic media. At this time a compound of the present invention in serum free DMEM is added to the cells, then they are cultured for a further 24 hours. [methyl-$^3$H]-thymidine (TRA120, GE Healthcare), 4 μCi, (0.15 MBq) per mL of media, is added for the last six hours of culture. At the end of the test period, the media is removed, (and stored at −80° C. for measurement of cytokine release), the cells are washed twice with ice cold PBS and then three times with ice cold 10% trichloroacetic acid for 10 minutes. The cells are washed one more time with methanol. Cell layers are then air dried and solubilised by the addition of 200 μL of 0.3 M NaOH containing 1% sodium dodecylsulphate for 1 hour at 37° C. After mixing 50 μL is removed and placed in 1 mL of scintillation fluid for counting in a beta-counter. Raw dpms are multiplied by 4 and divided by 1000 to give plotted values of cellular proliferation.

Example 16

Stability of the Compounds of the Present Invention in Rat Plasma and Liver Homogenate Tissue Fluids.

Blood and liver is collected form non-drug dosed male and female Wistar rats (aged 8-9 weeks, 200-250 g and 250-300 g respectively). Bloods are centrifuged at 8 K rpm for 5 min. Plasma are pooled and stored at −80° C. for later use. The rat livers are homogenized, diluted with three volumes of PBS, cloth filtered. The filtrate is used directly for stability studies.

Preparation of Fluid Samples.

Each compound is dissolved in DMSO to make 5 mM stock solution. 10 μL of the stock is diluted with either rat plasma or liver homogenate (490 μL) to make up a starting concentration of 10 μM (triplicates). The mixtures are vortexed and incubated at 37° C. At each time point of 0, 30, 60 and 180 minutes, 100 μL of the mixture is taken and diluted with 300 μL of acetonitrile. The mixture is vortexed and centrifuged. 350 μL of the liquid is transferred into a microfuge tube and concentrated using a rotational vacuum concentrator (Christ Beta-RVC, supplied by Quantum Scientific). 100 μL of acetonitrile-water (9:1, v/v) is added to the residue, vortexed and immediately analysed by LCMS/MS. Data from these experiments are expressed as percent of peak area recorded from the LCMS/MS trace at time zero ($t_0$).

Figure 10:
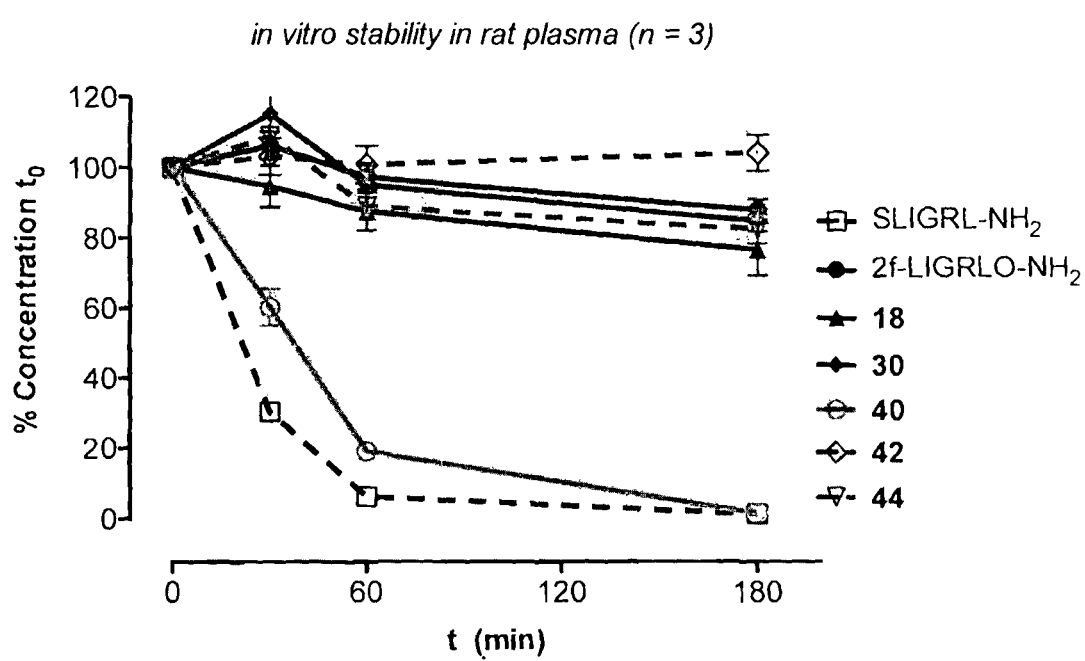
FIG. 10. Graphical representation of the stability of PAR2 antagonists (18, 30, 40, 42 and 44) compared to the known peptide agonists SLIGRL-NH$_2$ and 2-f-LIGRLO-NH$_2$ in rat plasma (derived from non-drug dosed Wistar rats).
Figure 11:
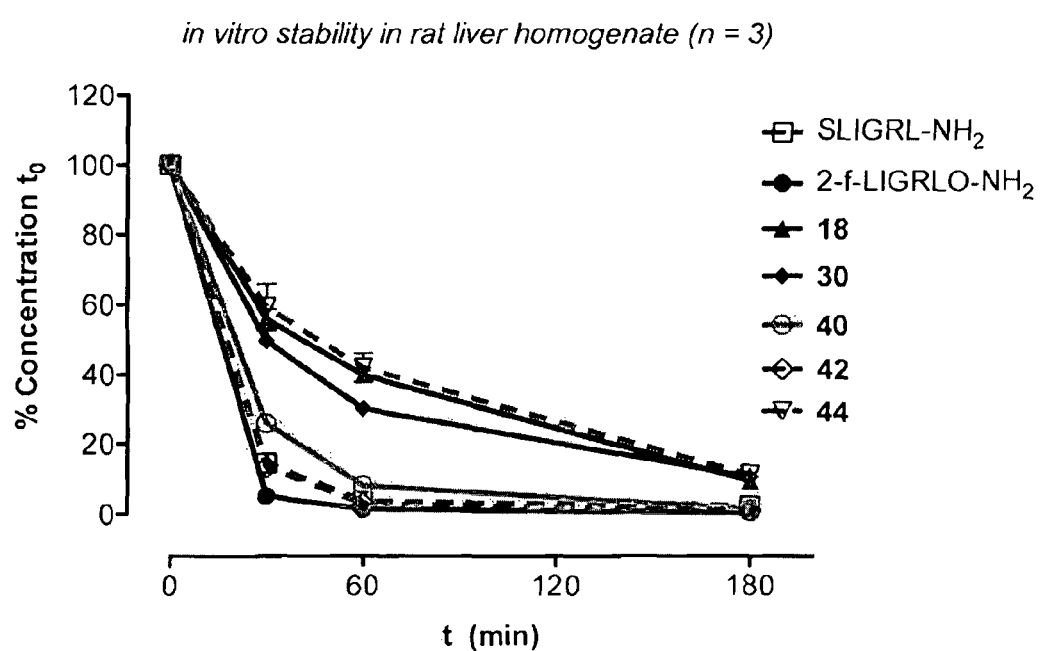
FIG. 11. Graphical representation of the stability of PAR2 antagonists (18, 30, 40, 42 and 44) compared to the known peptide agonists SLIGRL-NH$_2$ and 2-f-LIGRLO-NH$_2$ in rat liver homogenate (derived from non-drug dosed Wistar rats).

In general, the compounds (18, 30, 42 and 44) are stable in rat plasma (over 80% present after 3 h) and decomposed to varied degree in rat liver homogenate (FIGS. 10 and 11). The results support the hypothesis that the compounds are mainly metabolized in liver.

Example 17

Figure 12:
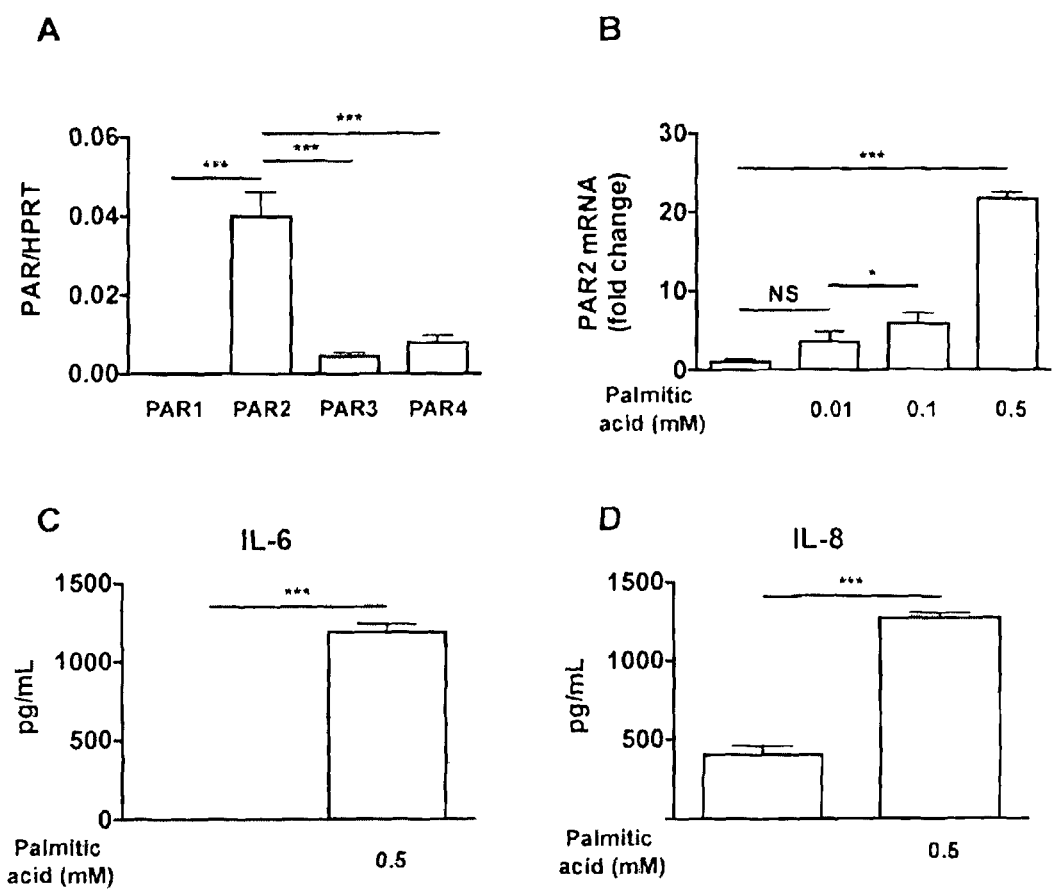
FIG. 12. Graphical representation of the effect of palmitic acid on primary human monocyte-derived macrophages.

Evaluation of PAR2 Antagonists in Regulating Macrophage Inflammation, Adiposity, Adipose Tissue Inflammation and Metabolic Function To investigate if PAR2 is specifically linked to macrophage inflammation, the effect of palmitic acid on mRNA levels of PARs on human monocyte derived macrophages (HMDMs) was measured (FIG. 12). Real-time POI measurements of PARs in HMDM and normalized against HPRT illustrates that the expression of PAR2 was significantly higher than the rest of the PAR family (PAR1, PAR3 and PAR4), indicating a regulatory role of PAR2 in macrophages (FIG. 12A). The increase of PAR2 mRNA in HMDM in the presence of palmitic acid was dose-dependent (FIG. 12B). Fold change in PAR2 was calculated relative to untreated sample. FIGS. 12C and D illustrate that palmitic acid stimulates proinflammition cytokines, IL-6 and IL-8, secretion from HMDM. Error bars are means±SEM; *P<0.05, P<0.01, *P<0.001. In vitro stimulation of human macrophages (HMDM) with palmitic acid showed a concentration dependent increase (<20 fold) in mRNA concentrations of PAR2 and protein expression of inflammatory cytokines (IL6 & IL8). This suggests that saturated fatty acids induce PAR2 activation that may play a major role in macrophage associated adipose tissue inflammation and adipocyte dysfunction (FIGS. 12B, C, and D).

Figure 13:
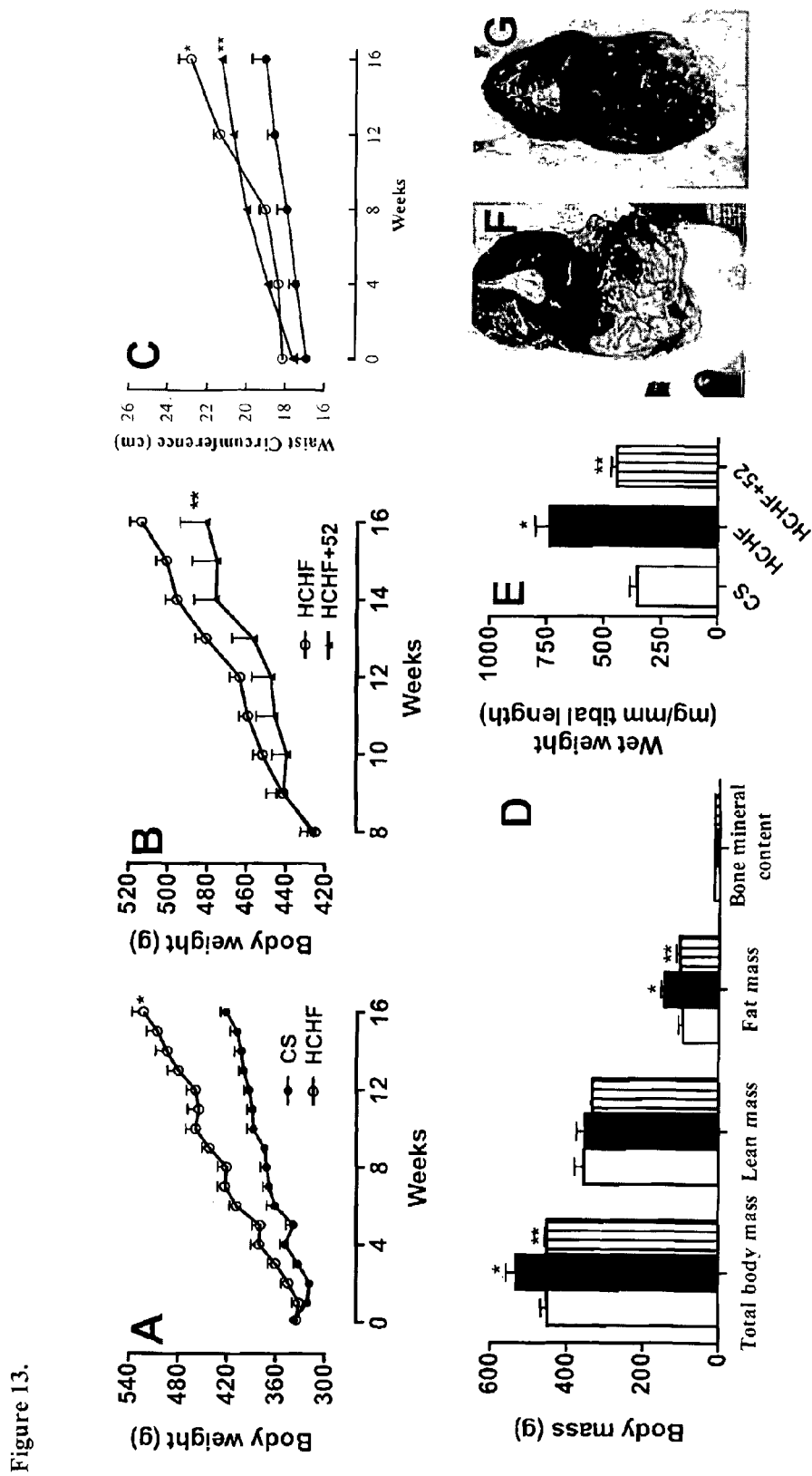
FIG. 13. Graphical representation of the regulation of obesity and adipose tissue immune-inflammatory cell infiltration by PAR2 antagonist 52 in diet-induced obese rats.

Selective PAR2 antagonist 52 was used to evaluate the therapeutic potential of PAR2 antagonism in regulating adiposity, adipose tissue inflammation and metabolic function in rats fed a diet high in carbohydrates and fats (HCHF). Weekly body weight measurements (0-16 weeks) were recorded for Corn Starch CS (●) and High Carbohydrate High Fat (HCHF) (○)-fed rats (FIG. 13A), as well as for HCHF (○) and HCHF+PAR2 antagonist 52 (▲)-treated rats (FIG. 13B). In addition, weekly waist circumference measurements were recorded for CS (●), HCHF (○), HCHF+PAR2 antagonist 52 (▲)-treated rats (FIG. 13 C). FIG. 13 D illustrates dual-X ray emission spectroscopy body composition measurements in CS (■), HCHF (▨), HCHF+PAR2 antagonist 52 (□)-treated rats.

Relative to rats fed a lean diet containing only corn starch (CS), those receiving the HCHF diet for 16 weeks become obese, gaining 54±4% body weight and 206±43% total fat mass, particularly visceral (abdominal) fat from week 0 to 16 (FIGS. 13A-G). FIG. 13F is an image of the abdominal fat pad at 16 weeks in rat given HCHF diet for 16 weeks, but no treatment. FIG. 13G shows the abdominal fat pad at 16 weeks in rat given HCHF diet for 16 weeks, plus PAR2 antagonist 52 (5 mg/kg/day p.o.) between weeks 8-16. The increase in PAR2 expression in adipose tissue (FIG. 14A) and its two component fractions, adipocytes and stromal vascular cell (SVC) fractions (FIG. 14B), were all elevated by HCHF feeding, positively correlating with increased adiposity. Local adipose tissue inflammation was also elevated by HCHF feeding (FIG. 15A-F). Findings indicate that a different endogenous signal—saturated fatty acids such as palmitic acid consumed in a HCHF diet—can prime macrophages to increase their expression of PAR2.

Figure 14:
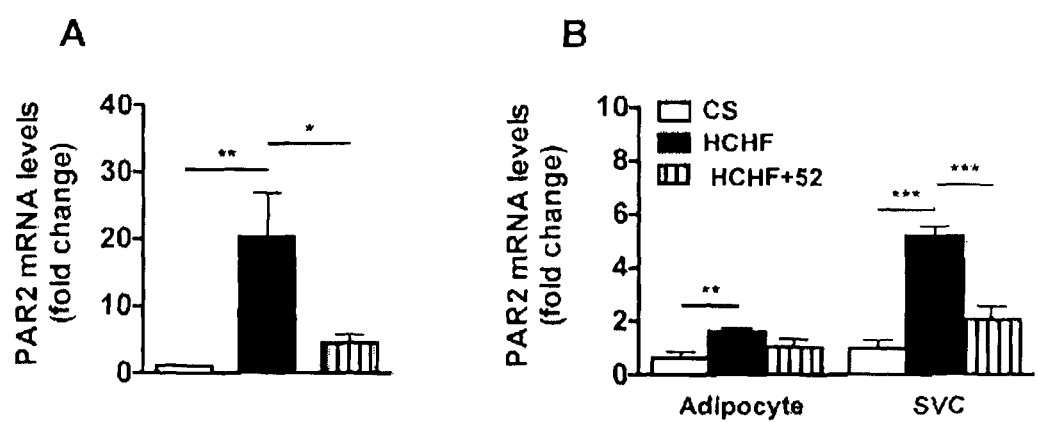
FIG. 14. Graphical representation of real-time PCR gene quantification of PAR2 mRNA.
Figure 16:
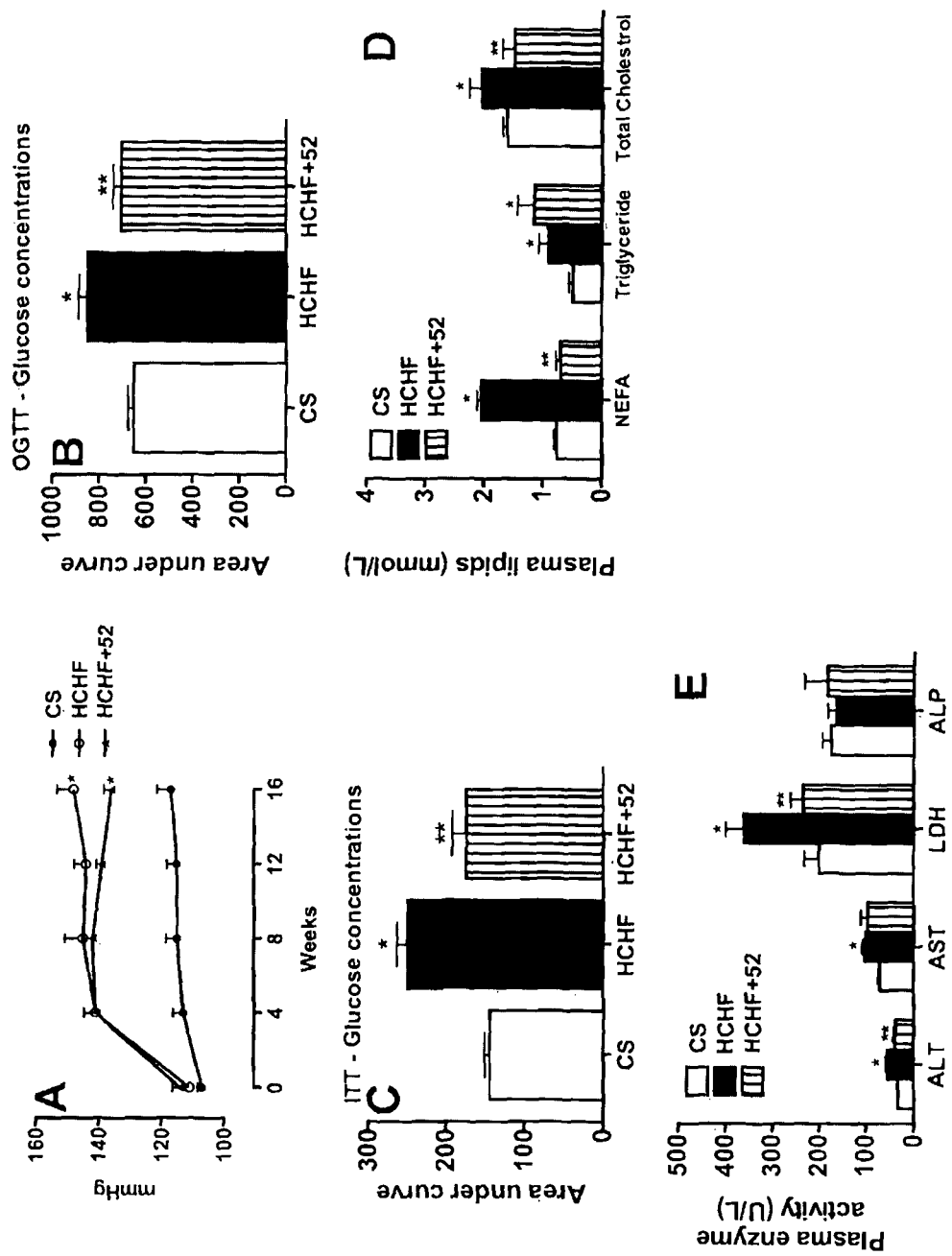
FIG. 16. Graphical representation of the regulation of metabolic parameters by PAR2 antagonist 52 in diet-induced rats.

The regulation of metabolic parameters by PAR2 antagonist 52 were measured in diet-induced obese rats including systolic blood pressure measurements in CS (●), HCHF (○) and HCHF+52 (▲)-treated rats (FIG. 16 A), oral glucose tolerance in CS (●), HCHF (○) and HCHF+PAR2 antagonist 52 (▲)-treated rats (FIG. 16 B), insulin tolerance in CS (●), HCHF (○), HCHF+PAR2 antagonist 52 (▲)-treated rats (FIG. 16 C), plasma lipid concentrations in CS, HCHF and HCHF+PAR2 antagonist 52-treated rats (FIG. 16 D and plasma liver enzymes in CS, HCHF and HCHF+52-treated rats (FIG. 16 E, *P<0.05 vs CS; **P<0.05 vs HCHF). After 16 weeks of HCHF feeding by Wistar rats, many of the metabolic indicators (FIG. 13 and FIG. 16) were attenuated or reversed by daily oral administration from weeks 8-16 with the PAR2 antagonist 52 (10 mg/kg/day), with prevention in body weight gain (weeks 8-16 HCHF, 21±1%; +52, X±X %; FIG. 13A), total fat mass (52, X %; FIG. 13 D), visceral (abdominal) fat deposition and whole adipose, adipocyte and SVC expression of PAR2 (FIGS. 13-14). The increase in PAR2 expression, in whole adipose, adipocyte and stromovascular cells (SVC), induced by HCHF feeding over 16 weeks was prevented by treatment with PAR2 antagonist 52 from weeks 8-16 with PAR2 mRNA concentrations being comparable to that in CS-fed rats (FIG. 14).

Figure 15:
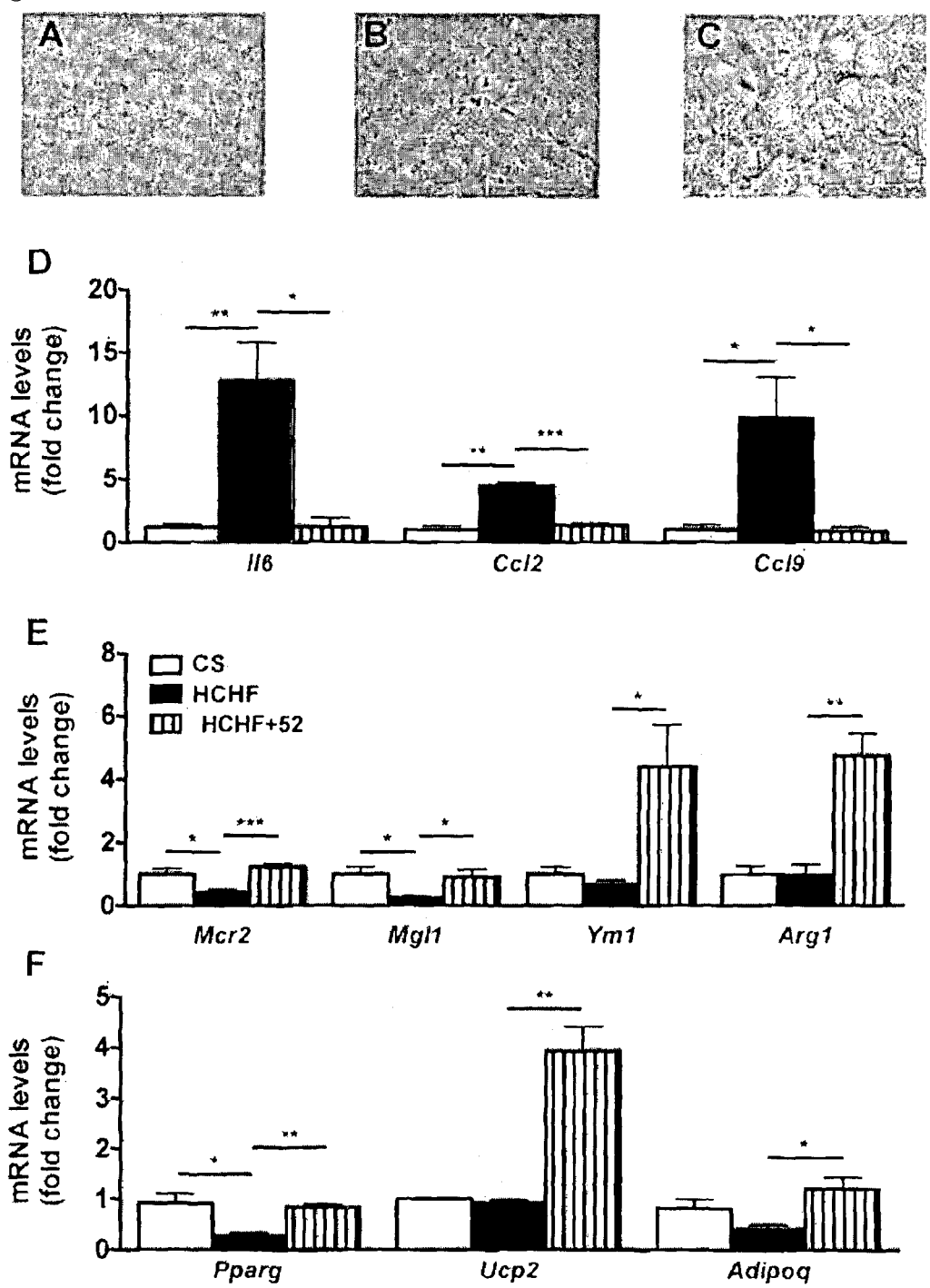
FIG. 15. Graphical representation of modulation of PAR2 antagonist 52 on adipose tissue inflammation.

Development of chronic adipocyte and metabolic dysfunction have also been associated with increased infiltration or recruitment of immune cells to adipose tissue (Lumeng, C. N., et al., *J Clin Invest* 2007, 117, 175-84; Nishimura, S. et al, *Nat Med* 2009, 15, 914-20; Liu, J. et al., *Nat Med* 2009, 15, 940-45). Immune cell infiltration into retroperitoneal adipose tissue was assessed by histochemical analysis, which revealed a very low distribution of monocytes/macrophages as single cells in adipose tissue of CS rats (FIGS. 15 A, B, C). However, the density of monocytes/macrophages in adipose tissue of HCHF rats was much greater, usually in clusters of cells throughout the interstitium. Macrophage activation can be broadly classified as two distinct polarization states, M1, 'classically activated' and M2, 'alternatively activated'. The classification of these states is largely dependent on expression of surface markers, metabolic enzymes and secretion of chemokines. M1 or 'classically activated' macrophages are generated in response to cell-mediated inflammatory responses such as TNF-α and IFN-γ. These M1 macrophages are generally associated with enhanced anti-microbial functions and production of proinflammatory chemokines and mediators. M2 or 'alternatively activated' are induced in the presence of IL-4 or IL-13. M2 macrophages are less efficient in production of proinflammatory mediators than M1 macrophages and instead secrete high levels of anti-inflammatory and wound healing mediators.

Figure 17:
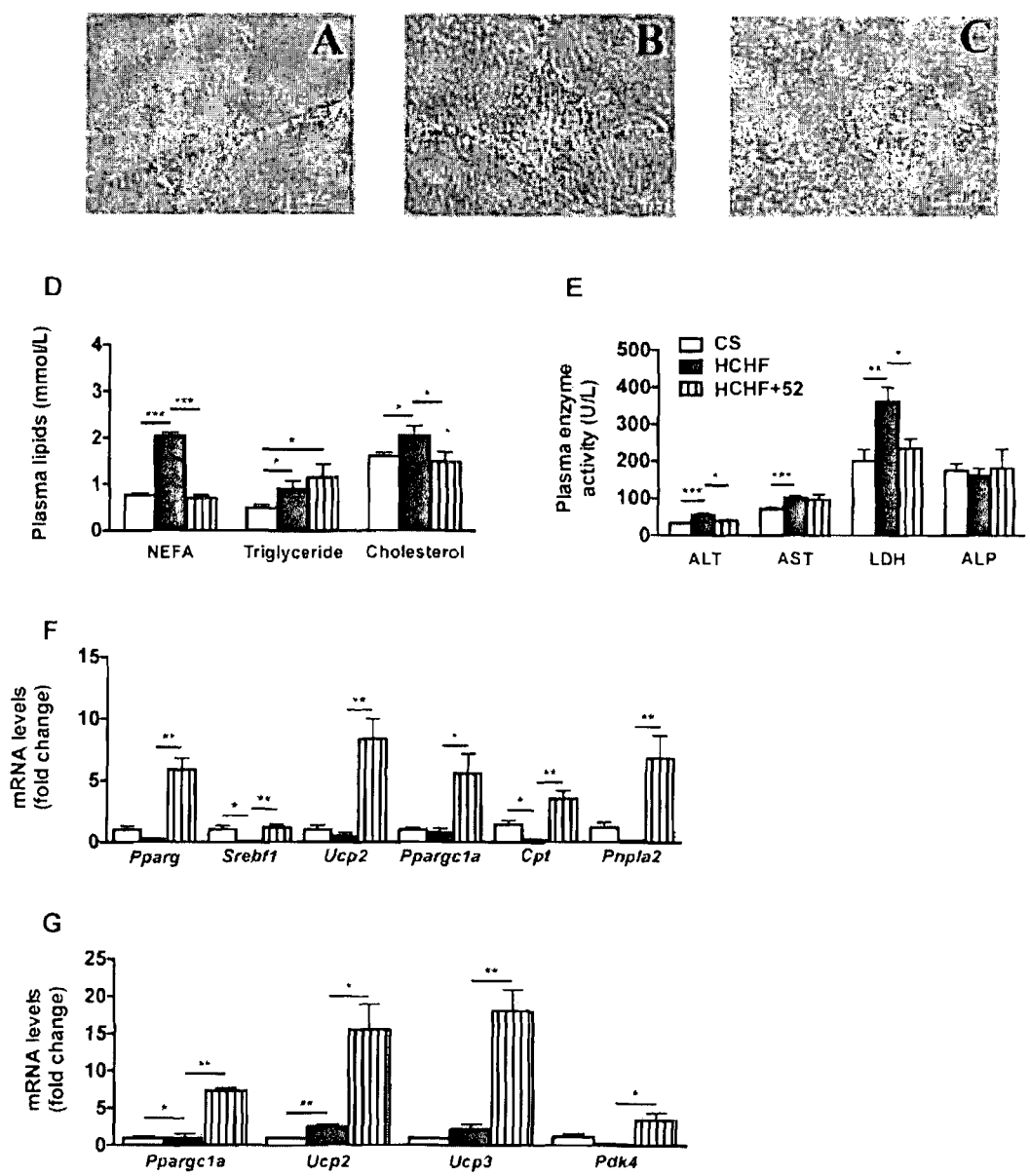
FIG. 17. Graphical representation of the effects of fatty acid oxidation in liver, skeletal muscle and pancreas in PAR2 antagonist 52 treated rats.

Given that macrophage-linked inflammation is critical in the development of metabolic dysfunction, we investigated the salutary effects of 52 on inflammatory status and metabolic aspects on adipose tissue. Adipose tissue from HCHF-fed rats showed increased expression of M1-specific proinflammatory genes, 116 (IL-6). Ccl2 (MCP-1) and Ccl9 (MIP-1), while rats treated with PAR2 antagonist 52 showed a drastic decreased in M1-specific genes (FIGS. 15 D, E). In contrast, expression of M2-specific genes, Mcr2 (C-type mannose receptor 2), Mgl1 (macrophage galactose-type C-type lectin 1), Ym1 (chitinase 3-like 3) and Arg1 (arginase 1) are decreased in HCHF-fed rat but restored or upregulated in rats treated with 52 (FIGS. 15 D, E). Other than M1 and M2 related genes, metabolic genes involved lipid and energy metabolism were examined. Obesity often develops together with the dysregulation of genes involved in fatty acid metabolism, cellular stress and adipocyte differentiation. PAR2 signaling has also been implicated in dysregulated fatty acid oxidation. In retroperitoneal adipose tissue, genes encoding for Pparg (peroxisome proliferator-activator receptor-γ), Ucp2 (uncoupling protein 2) and Adipoq (adiponectin) implicated in development of insulin resistance were altered in HCHF-fed rats (FIG. 15 F). Treatment with PAR2 antagonist 52 attenuated these changes (FIG. 15 F). Taken together, 52 potentially skewer polarization of macrophage towards M2 phenotype, preventing the accumulation of M1 macrophages in adipose tissue thus improving adipose tissue inflammation, adipocyte and metabolic function (FIGS. 15-17).

Fatty acid oxidation in liver, skeletal muscle and pancreas was observed in rats following treatment with CS, HCHF and HCHF+PAR2 antagonist 52. FIGS. 17A-C show representative images (20× magnification) of hepatocyte ultrastructure and fat deposition in CS (A), HCHF (B) and HCHF+PAR2 antagonist 52 (C)-treated rats. FIG. 17D shows metabolic genes in rat skeletal muscle of cornstarch (CS), high-carbohydrate high-fat (HCHF) and HCHF-treated with PAR2 antagonist (HCHF+52). FIG. 17E illustrates metabolic genes in rat liver of different groups. FIG. 17F shows expression of metabolic genes in pancreas. Expression of mRNA in was normalized against 18s rRNA and fold change was calculated relative to CS samples. Error bars are means±SEM; *P<0.05, P<0.01, *P<0.001.

Figure 18:
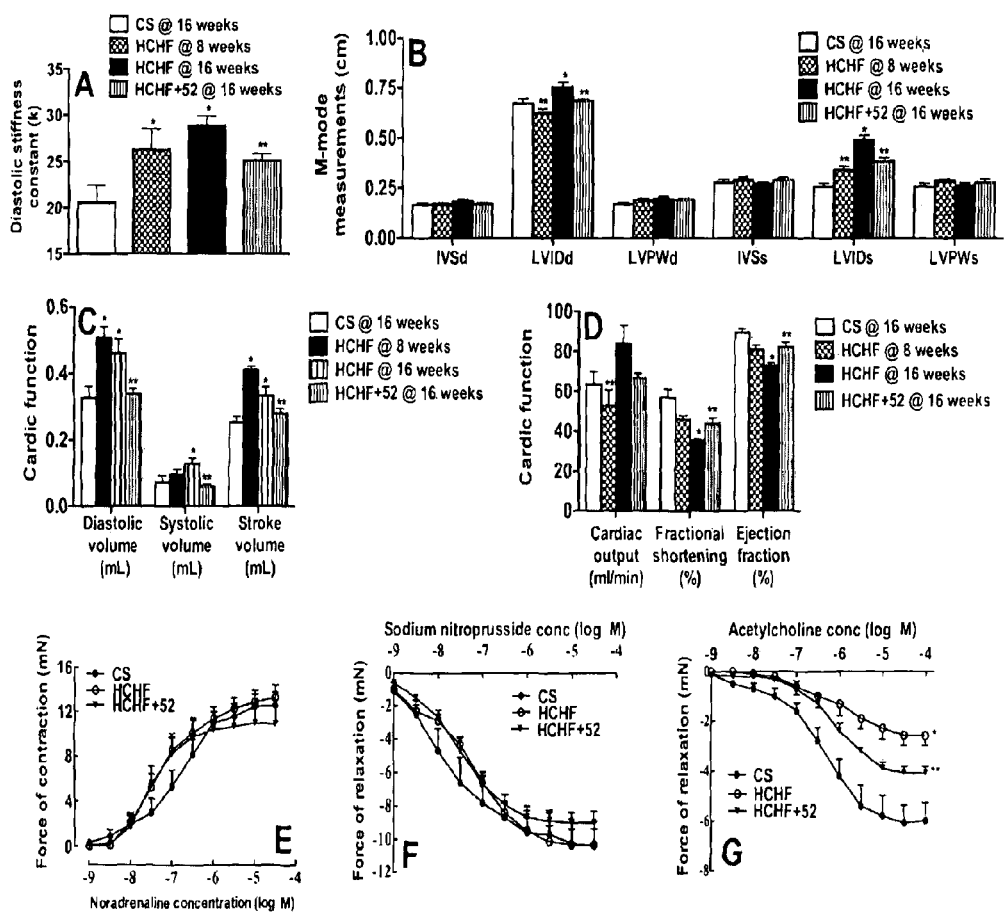
FIG. 18. Graphical representation of regulation of cardiovascular structure and function by PAR2 antagonist 52 in diet-induced obese rats.
Figure 18:
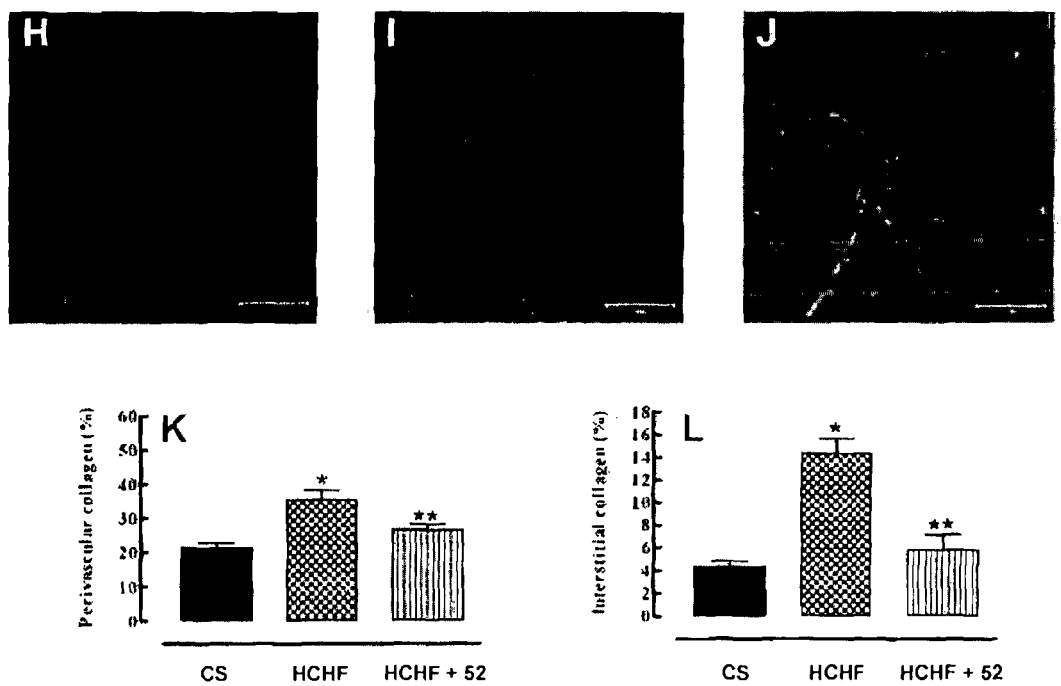

Regulation of cardiovascular structure and function by PAR2 antagonist 52 in diet-induced obese rats was also measured (FIG. 18), including diastolic stiffness constant measurements in CS, HCHF, HCHF+ compound 52-treated rats (FIG. 18A) and echocardiographic characterization of cardiac structure in CS, HCHF (at 8 weeks before treatment), HCHF and HCHF+ compound 52-treated rats FIG. 18B. FIGS. 18C and D show echocardiographic characterization of cardiac function in CS, HCHF (at 8 weeks before treatment), HCHF and HCHF+ compound 52-treated rats. FIGS. 18E-G illustrate vascular organ bath responses for noradrenaline (E), sodium nitroprusside (F) and acetylcholine (G) in CS (●), HCHF (○) and HCHF+C5aRA (▼)-treated rats. Representative images (40× magnification) of interstitial collagen deposition in the left ventricle of CS(H), HCHF (I) and HCHF+PAR2 antagonist 52 (J)-treated rats. FIGS. 18 K and L are graphical representations of the area of collagen deposition in perivascular (K) and interstitial (L) region of the left ventricle. *P<0.05 vs CS; **P<0.05 vs HCHF.

Metabolic parameters that were elevated in rats on the HCHF versus CS diet included impaired glucose and insulin tolerance (FIG. 16B-C), elevated plasma lipids and liver enzymes (FIG. 16D-E), increased systolic blood pressure (FIG. 16A) and abnormalities in cardiac structure and function (FIG. 18). It is notable that the PAR2 antagonist 52 had a potent inhibitory effect on the development of diet-induced cardiac fibrosis, as measured by increased collagen deposition (e.g. in the left ventricle of the heart). This anti-fibrotic effect of PAR2 antagonism may be an important therapeutic property, not only for cardiovascular disease but also for many other indications where tissue and organ fibrosis due to collagen deposition causes dysfunction of the tissue or organ.

Parameters, except for elevated triglycerides and systolic blood pressure, were attenuated by treatment with the PAR2 antagonist 52 from weeks 8-16 (FIGS. 16A and D). Further, the increased steatosis seen in HCHF rats compared to CS-fed was prevented by treatment with 52 (FIGS. 17 A, B, C). When the expression of genes involved in energy expenditure and fatty acid oxidation in the liver were analysed, the upregulation of peroxisome proliferator-activator receptor-γ (Pparg), Srebf1 (sterol regulatory element binding transcription factor 1), Ucp2, Ppargc1a, Cpt (carnitine palmitoyltransferase) and Pnpla2 (adipose triglyceride lipase) were detected in PAR2 antagonist 52 treated versus untreated HCHF rats (FIG. 17 F). PPAR-γ and the associated metabolic genes investigated above are all implicated in ameliorating insulin resistance and well known to regulate macrophage and liver lipid metabolism, mitochondrial biogenesis and triglyceride hydrolysis (Odegaard, J. I., et al., *Nature* 2007, 447, 1116-20; Chawla, A., *Circ Res* 2010, 106, 1559-69; Memon, R. A. et al., *Endocrinology* 2000, 141, 4021-31; Sookoian, S. et al., *Hepatology* 2010, 52, 1992-2000; Ong, K. T., et al, *Hepatology* 2010). In skeletal muscle, genes involved in lipid metabolism and energy expenditure, such as Pparg (peroxisome proliferator-activator receptor-γ), Ucp2 and 3 (Uncoupling protein 2/3) and Pdk4 (dehydrogenase kinase 4) were suppressed in HCHF-fed rats (FIG. 17 G). Real-time analysis of Glut2 (glucose transporter 2) and Beta2 (basic helix-loop-helix transcription factor) involved in metabolism and transcription factors are suppressed in HCFH-fed rats but restored upon treatment with PAR2 antagonist 52. Other genes such as Iapp (islet amyloid polypeptide), Atf3 (activating transcription factor 3), Fas (CD95) and Id-1 (inhibitor of DNA binding 1) were upregulated by HCHF feeding (FIGS. 17 F, G). Treatment with 52 attenuated this altered gene expression in both skeletal muscle and pancreas (FIGS. 17 F, G). These results, taken together with the altered expression of lipid-handling and fatty acid oxidation genes in the liver, skeletal muscle and pancreas suggest that the antagonism of PAR2 in HCHF-fed rats increases metabolism and correlates with decreased adiposity and metabolic symptoms in the treated rats.

In summary, oral administration of a novel PAR2 antagonist ameliorated classic symptoms of metabolic dysfunction in HCHF rats, with marked reduction in obesity and adiposity and improvements in glucose and insulin intolerance, adipose tissue inflammation, obesity-associated alteration in fatty acid metabolism as well as multiple lipid and cardiovascular abnormalities. These effects were traced to the expression and signal transduction of PAR2 on and in both adipocytes and macrophages in adipose tissue during diet-induced obesity. Further, extracellular signals or endogenous ligands such as palmitic acid and proteases may act as endogenous triggers to prime adipose tissue macrophages or other resident and infiltrating immune cells, thereby sustaining the increased expression and activation of PAR2 in diet-induced obesity and metabolic syndrome.

Example 18

PAR2 Regulates Glucose Homeostasis

Method: Glucose-Stimulated Insulin Secretion.

Rat pancreas and mouse MIN6 beta cells were cultured in DMEM (25 mM glucose) supplemented with 15% fetal calf serum, 10 U/mL penicillin, 10 U/mL streptomycin, 2 mM L-glutamine and 60 mM 2-mercaptoethanol. MIN6 beta cells were passaged and harvested using non-enzymatic cell dissociation solution (Sigma-Aldrich). Glucose-stimulated insulin secretion (GSIS) was performed as described next. MIN6 beta cells were seeded at 0.8×106 mL in a 96-well plate and cultured for 48 h. Cells were washed twice with glucose-free Krebs buffer (NaCl 119 mM, KCl 4.74 mM, $CaCl_2$ 2.54 mM, $MgCl_2$ 1.19 mM, $KH_2PO_4$ 1.19 mM, $NaHCO_3$ 25 mM, HEPES (pH 7.4) 10 mM and 0.05% BSA). Cells were pre-treated with compound 52 for 30 min with Krebs buffer supplemented with 2.5 mM glucose. After incubation, cells were washed twice with glucose-free Krebs buffer. Glucose (2.5 mM and 25 mM) and compounds were added at specified concentration and incubated for 1 h. Supernatants were collected and insulin concentrations were determined by ELISA (Abeam).

Results: Pathogenesis of pancreatic dysfunction is linked to chronic nutritional surplus and elevated fatty acids, so in vivo and in vitro effects of compound 52 were evaluated on rat pancreas and mouse MIN6 beta cells. Quantitative RT-PCR analysis revealed that pancreatic genes Glut2 (glucose transporter 2) and Beta2 (basic helix-loop-helix transcription factor), involved in metabolism and transcription, were suppressed in rats fed a diet high in carbohydrates and fats (HUH) relative to corn starch (CS) fed rats but were normalized in HCFH-fed rats upon treatment with compound 52. The genes, Lapp (islet amyloid polypeptide), Atf3 (activating transcription factor 3), Pas (CD95) and Id-1 (inhibitor of DNA binding 1), involved in insulin production and mediation of stress responses were upregulated in HCHF rats, but attenuated by treatment in vivo with compound 52. Rats fed the HCHF diet developed impaired glucose and insulin intolerance, but treatment with compound 52 improved glucose tolerance in an oral glucose tolerance test and improved responsiveness to insulin in an insulin tolerance test. Following treatment with compound 52, the HCHF-fed rats had comparable insulin sensitivity to untreated CS-fed rats. PAR2 agonists and compound 52 were further evaluated in vitro for glucose-stimulated insulin secretion (GSIS) and intracellular calcium mobilization in mouse MIN6 beta cells. Administering 2f-LIGRLO-$NH_2$ inhibited glucose stimulated insulin sensitivity in MIN6, while pre-treatment with compound 52 normalised insulin secretion. Three different PAR2 agonists (trypsin, SLIGRL-NH2, 2f-LIGRLO-$NH_2$) each activated intracellular calcium release in MIN6 beta cells in a concentration-dependent manner. These data support a close association between PAR2 activation, insulin modulation and glucose homeostasis.

Example 19

Human and Rat Obesity Increases PAR2 Expression

Paired omental and subcutaneous adipose biopsies (n=11) were obtained from Mater Medical Research Institute. Samples were categorized according to body mass index (BMI) as defined by the World Health Organization, lean subjects (n=2, BMI=21.4±1.2 kg/$m^2$), overweight subjects (n=5, BMI=27.3±1.8 kg/$m^2$) and obese subjects (n=4, BMI=32.9±1.5 kg/$m^2$). PAR2 mRNA expression in human adipose tissue was found to increase with body weight for a small cohort of eleven lean, overweight and obese people. Their body mass index (BMI) positively correlated with PAR2 expression in their omental and subcutaneous adipose tissue, suggesting that PAR2 expression is potentially a new biomarker for human obesity. This relationship between obesity and PAR2 mRNA expression was corroborated in Wistar rats, fed a high carbohydrate high fat diet for 18 weeks, which showed a 15 fold increase in PAR2 mRNA expression and a 2 fold increase in PAR2 protein expression in adipose tissue relative to rats fed a low fat cornstarch diet. Three quarters of this increased PAR2 expression was associated with the non-adipocyte stromal vascular fraction of rat adipose tissue, which contains extensive infiltrated macrophages and other immune cells implicated in the pathogenesis of obesity-associated chronic inflammation.

Example 20

PAR2 Antagonism in Experimental Arthritis

A human protease activated receptor 2 antagonist attenuates macrophage activation, mast cell degranulation and collagen-induced arthritis PAR2 antagonist 52 was examined for antagonism of PAR2-induced intracellular $Ca^{2+}$ release in human macrophages, inhibition of acute rat paw oedema induced by λ-carrageenan (1%) or β-tryptase (20 μg), and for disease-modifying anti-inflammatory activity in collagen-induced arthritis in rats. Tissues were analysed for collagen loss, macrophage infiltration, mast cell degranulation, and plasma pharmacokinetics wore measured.

PAR2 antagonist 52 was a 1000 fold more potent PAR2 antagonist than a reported compound (ENMD-1068) in human macrophages. PAR2 antagonist 52 reduced paw oedema induced by intraplantar λ-carrageenan or β-tryptase, yet did not inhibit proteolytic activity of tryptase in vitro. PAR2 antagonist 52 was orally bioavailable in tats (F=55%, 10 mg/kg/day/p.o.) and attenuated collagen-induced rat arthritis; ameliorating pathological and histopathological changes associated with disease (paw oedema, macrophage invasion, mast cell degranulation, pannus formation, synovial hyperplasia, collagen degradation).

Materials and Methods

Animals.

Male and female Wistar rats (aged 8-9 weeks, 250±50 g) were bred and housed at the Australian Institute for Bioengineering and Nanotechnology at The University of Queensland, Australia. Animals were maintained in a 12 h light/dark cycle according to the standard of holding facility with food and water provided. All experiments were approved by the animal ethics committee of The University of Queensland.

Drugs and Chemicals.

Bovine type B collagen (from nasal cartilage), Freund's incomplete adjuvant and heparin were supplied by Sigma (Aust.). Human recombinant lung β-tryptase was purchased from Promega. 2furoyl-LIGRLO-$NH_2$, PAR2 antagonist 52 and ENMD-1068 were synthesised according to literature. PAR2 antagonist 52 was dissolved in olive oil and administered by oral gavage (10 mg/kg/p.o., polypropylene feeding tubes, 18 G×75 mm, Instech Solomon, Aust) unless otherwise stated.

Macrophage Differentiation, Culture and Calcium Mobilization Assay.

Peripheral blood mononuclear cells were isolated from buffy coat (Australian Red Cross, Kelvin Grove, QLD) using Ficoll-paque density centrifugation (GE Healthcare Bio-Science, Uppsala, Sweden). $CD14^+$ monocytes were positively selected using $CD14^+$ MACS magnetic beads (Miltenyi Biotech, Auburn, Calif., USA). Monocytes were differentiated to HMDM in complete media using M-CSF (PeptroTech Inc, Rocky Hill, N.J., USA). HMDM were supplemented with 50% fresh complete medium containing CSF-1 on Day 5 after seeding and re-plated for use on Day 7.

Tryptase Activity Assay.

β-tryptase (10 ng/μL, 100 μL) was incubated±PAR2 antagonist 52 (20 μM) for 15 min, to which substrate tosyl-Gly-Pro-Arg-pNA (250 μM) was added. Absorbance was measured as optical density at 405 nm (FLUOstar Optima, BMG labtech, Aust.) every 41 s for 1 h.

Pharmacokinetics.

Male Wistar rats were surgically implanted with a jugular vein catheter. Blood samples (heparinised) were collected from the catheter of an unanaesthetised, unrestrained rat, 5 min prior to PAR2 antagonist 52 administration (10 mg/kg p.o.) and 30 min, 1-6, 8 and 24 h post-administration. Rats not implanted with a catheter were given PAR2 antagonist 52 (10 mg/kg/day p.o.) four days consecutively (n=6). On the fifth day, plasma, cerebrospinal fluid (CSF), paw tissue and intraperitoneal adipose were collected for LCMS analysis.

PAR2-Induced Paw Oedema.

Based on previous methods (Kelso E B et al., *J Pharmacol Exp Ther* 2006, 316(3):1017-24; Suen J Y et al., *Br J Pharmacol* 2011, doi: 10.1111/j.1476-5381.2011.01610.x.), PAR2 antagonist 52 (10 mg/kg s.c.; n=4), ENMD-1068 (100 mg/kg s.c.; n=4) or vehicle control (DMSO s.c.; n=2) were administered to male Wistar rats. Baseline paw thickness and width were measured using digital calipers (World Precision Instruments, USA) expressed in area ($mm^2$; thickness×width). Fifteen minutes later, 2Furoyl-LIGLRO-$NH_2$ (350 μg/paw in 100 μL saline) was injected into of the right hind paw pad (intraplantar, i.pl.). The left hind paw acted as a control, receiving saline only. In a separate experiment, vehicle (500 μL olive oil) versus PAR2 antagonist 52 (10 mg/kg p.o. in 500 μL olive oil) only were administered orally to two groups of rats (4 per group). Two hours later, β-tryptase (human recombinant lung, 20 μg in 100 μL saline) was injected into the right hind paw pad (vehicle in left for control) of all animals in each group. In all experiments, paw swelling was measured and expressed in area ($mm^2$; thickness×width) and plotted as % change from baseline of each individual paw.

λ-Carrageenan-Induced Paw Oedema.

Methods were based on literature (Kelso E B et al., *J Pharmacol Exp Ther* 2006, 316(3):1017-24; Kawabata A et al., *Peptides* 2001, 23(6):1181-3). Male Wistar rats (n=4 per group) were given 10 mg/kg PAR2 antagonist 52 (p.o. via gavage in olive oil, 500 μL). Control animals received only olive oil. Thirty minutes later, λ-carrageenan was administered into the right hind paw pad (1% w/v in saline, 100 μL, i.pl, Left paw saline control). Paw thickness and width were measured at 1-6, 8 and 24 h (as above) and swelling expressed in area ($mm^2$) and plotted as % change from baseline of each individual paw.

Collagen-Induced Arthritis.

Protocols were based on those described (Lin H S et al., *Br J Pharmacol* 2007, 150(7):862-72; Nishikawa M et al., *Arthritis Rheum* 2003, 48(9):2670-81). Female Wistar rats (200-250 g, n' 14) were immunised on Day 0 with Bovine nasal collagen (200 μg, 50:50 0.05 M acetic acid and Freund's incomplete adjuvant, s.c. tail base). Sham animals received vehicle only (no collagen; 50:50 0.05 M acetic acid and Freund's incomplete adjuvant, s.c. tail base). Boosters of the same dose were given on Day 7. Daily oral dosage of PAR-2 antagonist 52 (10 mg/kg in olive oil, 500 μL, p.o. weight adjusted) or olive oil vehicle (arthritic control, and sham) began on Day 7. Paw thickness and width (as above), body weight, disease activity score and mechanical nociceptive thresholds were measured every second day from Day 10-28.

Disease Activity Index (DAI) and mechanical hyperalgesia were assessed and qualitatively scored 0 to 4+. The DAI is based on multiple characteristic disease pathologies, incorporating changes in mobility, inflammation and discomfort/pain (maximum total score of 18). Plantar mechanical nociceptive thresholds were measured using Semmes Weinstein Von Frey Anaesthesiometers (Touch Test Sensory Evaluators, Stoelting, Ill., USA).

Histopathology and Joint Assessment.

Day 28 all rats were euthanised and hind paws fixed in 4% paraformaldehyde, decalcified and embedded in paraffin wax and cut at 10 μM. Sections were stained with H&E for general tissue architecture, with Masson's Trichrome for collagen loss or with alcian blue/safranin-O for mast cells (42). Tissue macrophages were labeled using ED1 monoclonal antibody (for immature rat macrophage/monocytes, Serotec) using standard IHC techniques. Microscopic analysis and cell counts were made from multiple (>6) images/paw with aid of ImageJ 1.42q software.

Data Analysis.

All experimental results were expressed as mean±SEM. Data were analysed using GraphPad Prism (v5.0a, San Diego, Calif.). Two-way repeated measures ANOVA for data sets involving three or more groups. For individual time points, one-way ANOVA were used, and groups compared with Bonferroni post-tests. Student's t-test was used for data comparing two data sets. Significance was set at p<0.05.

PAR2 Antagonist 52 is Orally Bioavailable.

Blood from rats given PAR2 antagonist 52 by oral gavage (10 mg/kg) was analysed for plasma concentration of drug ($C_p$) with $T_{max}$ 4.0±0.6 h, $C_{max}$ 1.7±0.4 μM and $T_{1/2}$ 1.13±0.13 h. No PAR2 antagonist 52 was present in plasma after 24 h. Although this compound is not water soluble enough to administer i.v., the oral bioavailability (F ~55%, n=3) could be determined from the area under the $C_p$ curve (AUC 0-6 h) at the given dose (10 mg/kg p.o.).

Plasma and adipose tissue collected post-mortem from animals that received PAR2 antagonist 52 for 4 days prior (10 mg/kg/day p.o.) had relatively high PAR2 antagonist 52 $C_p$ at 24 h after the fourth dose (0.5±0.1 µM, n=6, ~30% greater than the single-dose $C_p$ at 24 h). Intraperitoneal adipose also had a relatively high concentration of PAR2 antagonist 52 (0.15±0.02 µM, n=6, ~30% of $C_p$ at 24 h). No PAR2 antagonist 52 was detected in cerebral spinal fluid (LCMS/MS detection limit <1.8 nM, n=3), suggesting that PAR2 antagonist 52 did not effectively cross the blood-CSF barrier, which is not surprising for such a large hydrophobic drug (CLogP 5.8).

PAR2 Antagonist 52 Reduces PAR2 Agonist-Induced Oedema.

PAR2 antagonist 52 was assessed in vivo in a rat model of paw oedema and inflammation induced by the PAR2 peptide agonist, 2furoyl-LIGLRO-NH$_2$ (350 µg/paw), which is widely used by researchers to study PAR2 function in vitro and in vivo (2).

Figure 19:
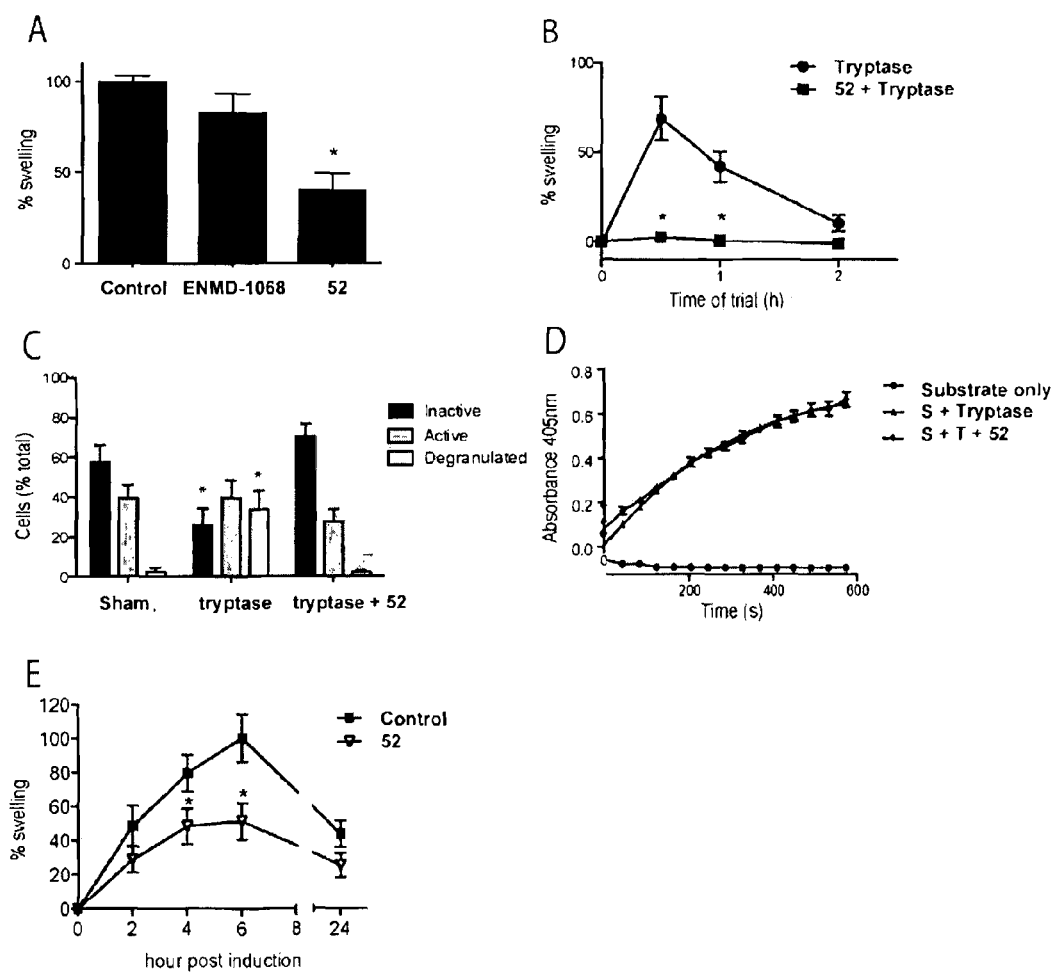
FIG. 19. Graphical representation of the attenuation of experimental paw oedema in rats by PAR2 antagonist 52.

In summary, FIG. 19 shows that PAR2 antagonist 52 attenuates experimental paw oedema in rats. (A) PAR2 antagonist 52 (10 mg/kg s.c. in DMSO, n=3) but not ENMD-1068 (100 mg/kg s.c., n=3) reduced the paw oedema induced by 2furoyl-LIGRLO-NH$_2$ (350 µg/paw, maximal swelling at 1 h shown). (B) Orally administered PAR2 antagonist 52 (10 mg/kg p.o. in olive oil) prevented the oedema induced by β-tryptase (20 µg/paw). (C) β-tryptase-induced oedema was associated with mast cell degranulation in the extrasynovium, which was ameliorated by PAR2 antagonist 52 pretreatment (10 mg/kg, n=4/group). (D) PAR2 antagonist 52 (20 µM) did not inhibit the enzyme activity of β-tryptase (1 ng/mL) on the chromogenic substrate Tosyl-Gly-Pro-Arg-pNA (absorbance as optical density at 405 nm, n=4-5). (E) Intraplantar administration of 1% λ-carrageenan induced lasting oedema, which was reduced to 50% by PAR2 antagonist 52 (10 mg/kg p.o, n=4/group, *p<0.05). Data expressed as mean±SEM.

PAR2 antagonist 52 (10 mg/kg s.c.) was found to strongly reduce the paw oedema, whereas a comparator compound ENMD-1068 had no effect at 100 mg/kg s.c. in this model of PAR2-induced acute inflammation in rats (FIG. 19A). PAR2 antagonist 52 was recently found to inhibit paw oedema induced by other PAR2 agonists, e.g. trypsin, SLI-GRL-NH2 and GB110.

When given orally, PAR2 antagonist 52 (10 mg/kg) strongly inhibited the rat paw oedema induced 2 h later by intraplantar injection of the endogenous PAR2 agonist β-tryptase (20 µg/100 µL/paw) (FIG. 19B). This timing allows for greater serum levels of antagonist (Cmax 4 h) to be present when maximum paw oedema has been induced by tryptase (30 min after administration of tryptase). The population of degranulated mast cells in the extrasynovium was significantly increased in β-tryptase-treated rats, as detected histologically by alcian blue/safranin-O staining, but was prevented by PAR2 antagonist 52 pretreatment (p<0.05, FIG. 19C). The total population of mast cells in this region did not change in response to β-tryptase. Using LCMS/MS, PAR2 antagonist 52 was also detected in paw tissue homogenates 3 h post administration (0.035 µM), indicating that the compound reached the target tissue where the effect was being measured. This anti-inflammatory activity was not due to direct inhibition of the β-tryptase enzyme, since the in vitro activity of human β-tryptase (1 ng/mL) was not inhibited by PAR2 antagonist 52 (20 µM) (FIG. 19D). This supports the notion that the proinflammatory action of tryptase in vivo in rats is mediated through PAR2, and can be blocked in vivo by a PAR2 antagonist. It can also be concluded that PAR2 antagonism in vivo prevents mast all degranulation promoted by an endogenous proteolytic agonist of PAR2.

PAR2 Antagonist 52 Reduces Carrageenan-Induced Paw Oedema.

Intraplantar administration of 1% λ-carrageenan induced a significant and long lasting paw oedema in control rats (n=4, FIG. 19E). Prophylactic treatment with PAR2 antagonist 52 (10 mg/kg p.o. n=4) 30 minutes prior to carrageenan significantly reduced swelling (~0.50%), which was most pronounced at 6 h. Swelling was not completely ameliorated in this acute inflammation model, but this may relate to the time course of experimentation with $C_{max}$ not being reached at oedema induction ($T_{max}$ 4 h). Thus, PAR2 antagonist 52 inhibited PAR2 specific inflammation induced by 2furoyl-LIGLRO-NH$_2$ and tryptase, as well as the non-specific inflammation induced by carrageenan.

PAR2 Antagonist 52 Ameliorates Collagen-Induced Arthritis.

Tests were carried out to determine whether orally administered PAR2 antagonist 52 was also anti-inflammatory in a chronic model of inflammatory disease, collagen-induced arthritis (CIA) in rats.

Figure 20:
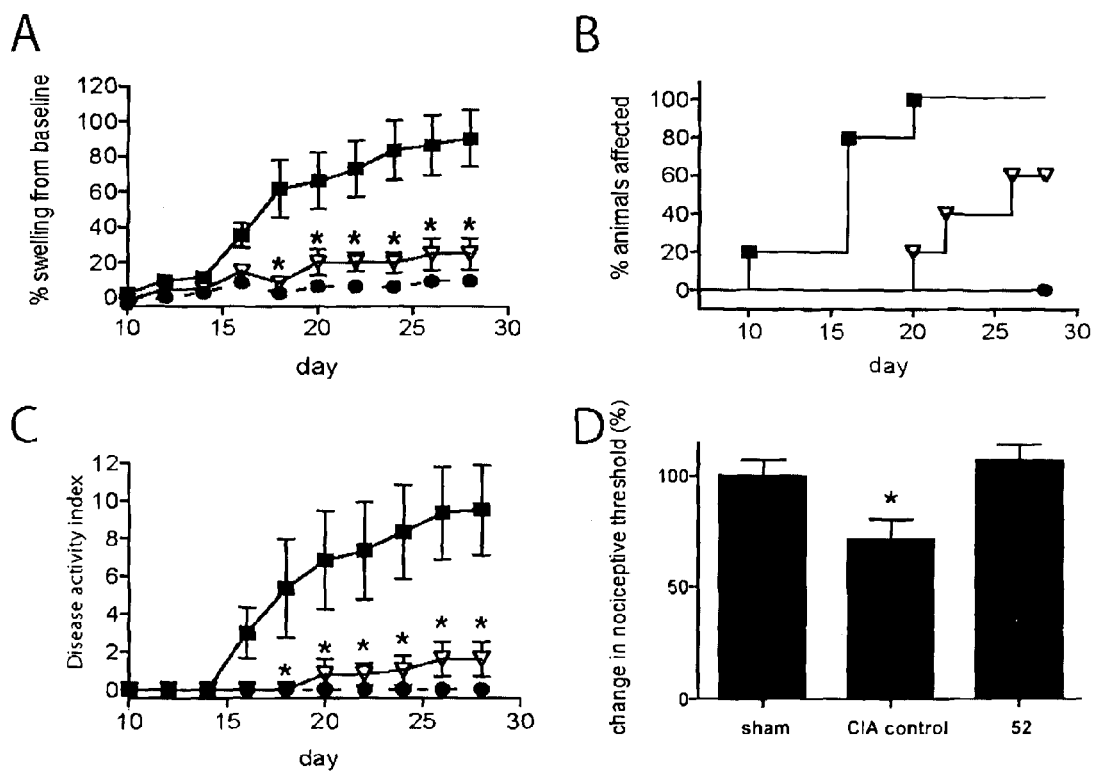
FIG. 20. Graphical representation of prophylactic amelioration of the pathophysiology of collagen-induced arthritis by PAR2 antagonist 52.

In summary, FIG. 20 shows that prophylactic PAR2 antagonist 52 ameliorates the pathophysiology of collagen-induced arthritis. PAR2 antagonist 52 (10 mg/kg/day p.o.) induced (A) significant prevention of hind paw swelling, (B) significant reduction in animals affected with arthritic signs and (C) reduction in DAI compared to non-treated CIA-controls (*p<0.05, two-way ANOVA, Chi square for (B)). (D) PAR2 antagonist 52 also prevented the mechanical hyperalgaesia associated with CIA (*p<0.05 ANOVA). Sham (closed circles); n=3, CIA-control (closed squares) n=6, PAR2 antagonist 52 (open triangles); n=5. Data expressed as mean±SEM.

Collagen inoculation induces a progressive paw swelling, particularly in hind limbs (FIG. 20A). By Day 20, all rats in the CIA-control group had at least one paw affected by arthritic signs (FIG. 20B), with swelling of 66±16% (n=6). Swelling continued to increase in CIA-control animals to 90±16% greater than baseline on Day 28 (FIG. 20A). In contrast, PAR2 antagonist 52 treatment (10 mg/kg/day p.o., n5) showed 60% animals were affected by Day 28, all of which displayed only mild (maximal) swelling of 25±9% (p<0.05 from CIA-control, FIGS. 20A and B). The increase in paw swelling correlated with observed DAI. Typically, rats showed appearance of inflammatory signs (swelling and redness) on Day 17. CIA-control animals showed a progressively deteriorating DAI, which increased to 9.5±2.4 by Day 28 (FIG. 20C). Animals treated with PAR2 antagonist 52 were significantly protected from developing arthritic-like signs, showing only mild DAI scores on Day 28 (maximal DAI 1.6±0.9 (p<0.05), FIG. 20C). Sham animals displayed no signs of arthritic disease. The mechanical nociceptive threshold associated with paw swelling was ~30% lower in CIA-controls compared to sham on Day 28 (p<0.05) but this effect was removed by treatment with PAR2 antagonist 52 (p<0.05 from CIA-controls, FIG. 20D).

PAR2 Antagonist 52 Prevents Histopathological Changes During Arthritogenesis

Figure 21:
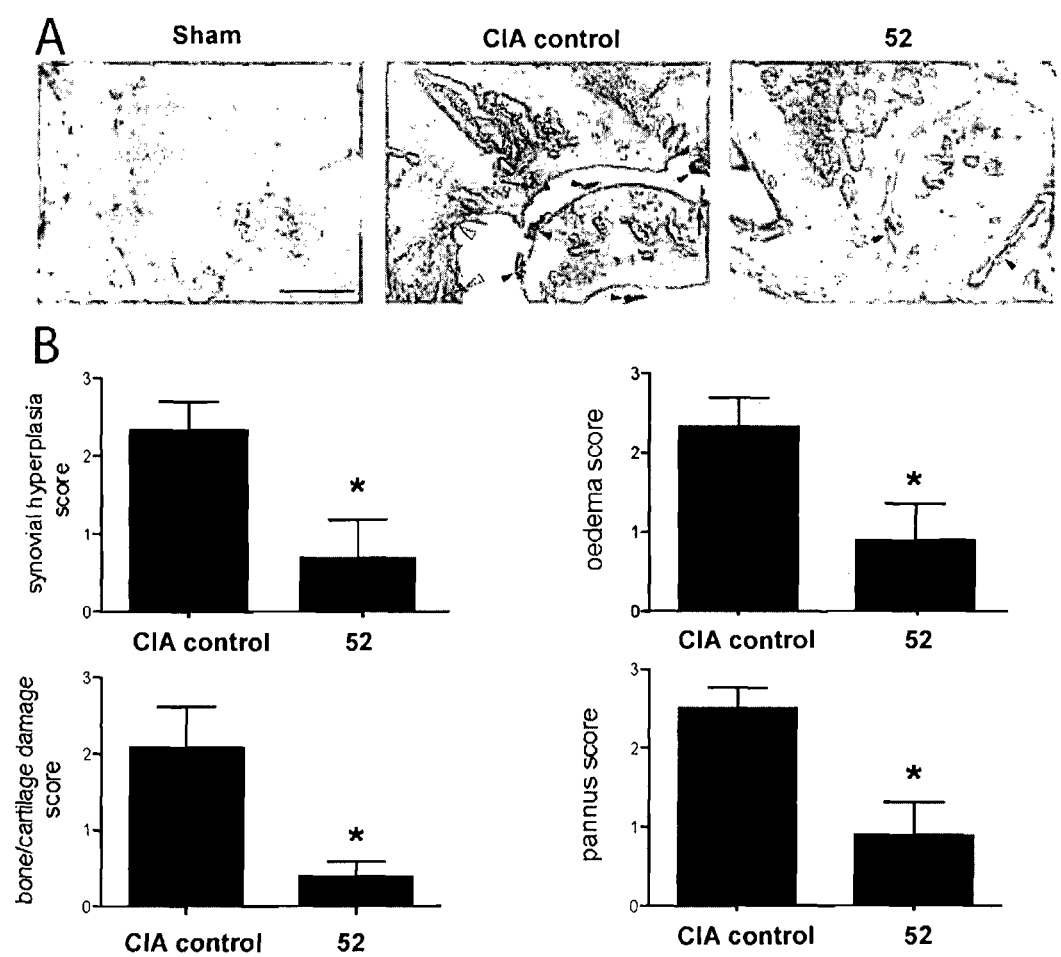
FIG. 21. Graphical representation of the alleviation of histopathological changes during arthritogenesis by prophylactic administration of PAR2 antagonist 52 together with photomicrographs of stained ankle sections.

As shown in FIG. 21, prophylactic administration of PAR2 antagonist 52 alleviates histopathological changes during arthritogenesis. (A) Representative photomicrographs of H&E stained ankle sections (tibia-talus joint) demonstrate reduced arthritic histopathology of animals treated with PAR2 antagonist 52 compared to CIA-control. Extra-synovial inflammatory cell invasion (open arrows), synovial hyperplasia (open arrowheads), cartilage/bone erosion (filled arrows) and pannus and rice body formation (filled arrowheads) are all reduced (Scale bar 200 µm). (B) Histopathological scoring for CIA control and animals treated with PAR2 antagonist 52 for all four parameters (synovial hyperplasia, oedema, bone/cartilage erosion, pannus formation) quantify significantly reduced histopathology in rats treated with PAR2 antagonist 52. Sham animals showed no histopathologies (*p<0.05, student's t-test, control n=6, PAR2 antagonist 52 n=5). Data expressed as mean±SEM.

Histological examination of H&E stained tibia-talus joints revealed that CIA-control animals had severe cardinal histopathologies associated with arthritic disease, such as oedema, inflammatory cell invasion, synovial hyperplasia, synovial rice bodies, pannus formation, cartilage damage and bone erosion (FIGS. 21A and B). Daily administration of PAR2 antagonist 52 almost completely prevented all histopathological changes (p<0.05 from CIA-control, FIG. 21E). Masson's Trichrome-stained tissue showed significantly reduced collagen loss in rats treated with PAR2 antagonist 52 compared to CIA-controls, having a greater proportion of aniline blue staining (FIGS. 22A and D). This corresponded well with results of cartilage/bone erosion observed in the H&E stained sections. Immunohistochemistry showed that the ED1-positive macrophage population was significantly increased in CIA-control animals, particularly within the synovium, pannus and lining the articular surface (FIG. 22C, p<0.05). In agreement with the H&E observation, PAR2 antagonist 52 prevented the arthritic-like up regulation of ED1-macrophages in CIA-controls, showing no difference from sham cell populations (FIGS. 22C and F). In all histologically stained tissue, sham animals were devoid of arthritic signs.

PAR2 Antagonist 52 Prevents Arthritis-Like Mast Cell Degranulation

Figure 22:
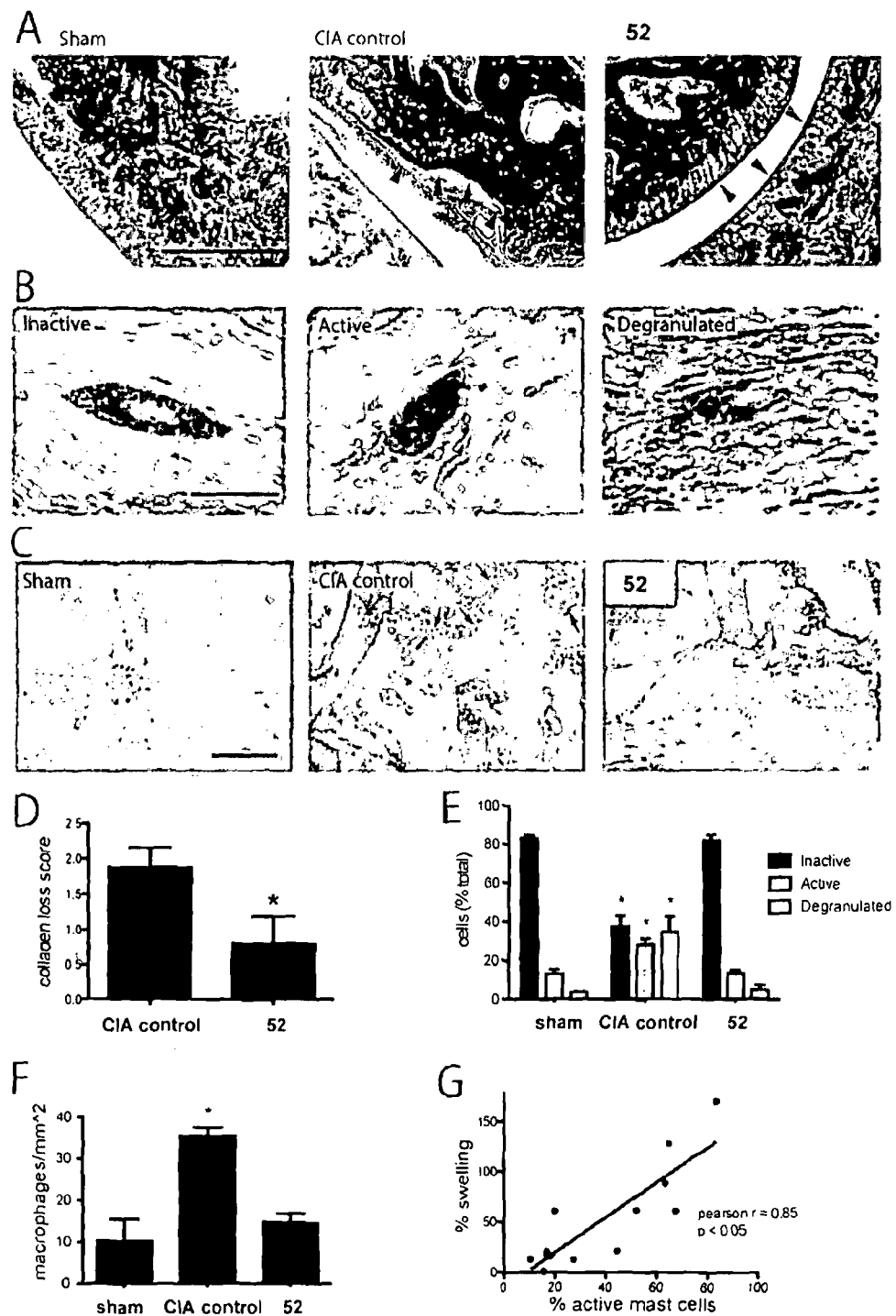
FIG. 22. Graphical representations and photomicrographs of stained ankle sections showing reduction of arthritis-like collagen loss, mast cell degranulation and macrophage accumulation in diseased joints by PAR2 antagonist 52.

As shown in FIG. 22, PAR2 antagonist 52 reduces arthritis-like collagen loss, mast cell degranulation and macrophage accumulation in diseased joints. (A) Masson's Trichrome-stained ankle sections (tibia-talus joint). Filled arrowheads denote areas of collagen and bone degradation (red stain, Scale bar 200 µm). (B) Differential alcian blue/safranin-O stained mast cells in rat paw sections (Inactive (red), Active (red/blue mix), Degranulated (blue). Scale bar 20 µm). (C) ED-1 (DAB, brown) stained rat paw sections demonstrate significant increase in invading macrophages (arrows) in CIA-control compared to both sham and animals treated with PAR2 antagonist 52 (Scale bar 200 µm). (D) Quantified collagen loss shows PAR2 antagonist 52 prevents collagen erosion (*p<0.05). (E) Quantitative analysis of stained mast cells displaying significantly higher active and degranulated mast cell proportions in CIA-controls compared to both sham and animals treated with PAR2 antagonist 52 (*p<0.05, ANOVA). (F) ED-1 stained macrophages revealed greater population of invading macrophages in CIA than sham, which was normalised by PAR2 antagonist 52 treatment (10 mg/kg/day p.o.). (G) Regression analysis of % paw swelling and % active/degranulated mast cell reveals a strong correlation (Pearson r=0.85, p<0.05). For all data Sham n=3, CIA-control n=4, PAR2 antagonist 52 n=4. Data expressed as mean±SEM.

Differential alcian blue/safranin-O staining (FIG. 22B) revealed mast cell activation and degranulation was 33% greater in CIA-controls. Two thirds of the total mast cells were either active or degranulated. Animals treated with PAR2 antagonist 52 showed no difference in mast cell activation state compared to sham, with ~80% of all mast cells being inactive and less than 5% being degranulated (FIG. 22E). No difference in total mast cell population was measured between all treatment groups (76.7±6.7 cells/mm$^2$, n=13). Regression analysis showed a strong positive correlation between paw swelling and active mast cells (incorporating cells considered either active or degranulated; Pearson r=0.85, p<0.05, FIG. 22G), and between percent active mast cell and synovial macrophage populations (Pearson r=0.89, p<0.005), supporting a functional link between active mast cells, macrophages and paw swelling in the CIA model. Unlike mast cells, there was a weak correlation between macrophage populations and paw swelling (Pearson r=0.63, p=0.025), suggesting macrophages may not substantially contribute per se to the observed swelling, but do contribute to bone and cartilage erosion (see FIG. 22C).

Example 21

Modulation of Colonocytes, Colitis and Inflammatory Bowel Disease

Crohn's disease (CD) and ulcerative colitis (UC) are common forms of chronic inflammatory bowel disease (IBD) that share common pathologies. UC affects the colon and rectum, CD affects multiple regions of the colon and ileum, and each condition has characteristic patterns of ulcerative mucosa. IBDs increase the risks of developing sepsis after stenosis-related bowel perforation, colorectal carcinoma, and multiple organ dysfunction.
Colonocyte Modulation.

Human colorectal adenocarcinoma (HT29) cells were incubated with a calcium binding dye (Fura3) buffer for 1 h at 37° C. Cells were treated with compound 52 or the previously reported compound N1-3-methylbutyryl-N4-6-aminohexanoyl-piperazine (ENMD-1068) at various concentrations for 15 min before the addition of 2Furoyl-LIGRLO-NH$_2$ (1 M). Intracellular calcium mobilization was measured by differences in fluorescence plotted against corresponding antagonist concentrations, enabling the determination of antagonist potency. Compound 52 was found to inhibit intracellular calcium release in human HT29 colonocytes. Compound 52 was a more potent antagonist of PAR2 activation in colonocytes than previously reported compound ENMD-1068 (IC$_{50}$ 8 M versus 5 mM).
PAR2-Induced Acute Colonic Inflammation.

Wistar rats Rats were fasted overnight and anesthetized with isofluorane for 2 h after receiving either a single oral dose of compound 52 (10 mg/kg p.o.) or vehicle (olive oil). A polyethylene catheter (1.7-mm outer diameter) was inserted 8 cm into the colon via the anus, through which SLIGRL-NH$_2$ (1 mg/rat) or saline vehicle (500 l) was administered. Rats remained anesthetized for 10 min and maintained at an angle of 40° to prevent leakage from the anus. Rats were allowed to recover with food and water supplied. All rats were terminated at 10 h after induction and scored appropriately for disease activity index (DAI) and macroscopic disease (see Disease Activity Index below). Colon tissue was taken for wet/dry ratio and MPO assay. Compound 52 exhibited anti-inflammatory activity in this PAR2 agonist-induced acute colonic inflammation. Acute colonic inflammation induced in rats by the PAR2 agonist SLIGRL-NH$_2$ was inhibited by oral administration of compound 52 (10 mg/kg) with markedly reduced edema, mucin depletion, PAR2 receptor internalization, and mastocytosis.

TNBS-Induced Chronic Colitis Model.

On day 0, rats were weighed, given respective treatments of either sulfasalazine (100 mg/kg in olive oil p.o.), compound 52 (10 mg/kg in olive oil), or vehicle (500 l olive oil p.o.), and fasted for 24 h with water supplied ad libitum. The next day (day 1), rats were weighed, dosed with respective compound, and anesthetized with isofluorane. A polyethylene catheter was inserted intrarectally (8 cm). Control and drug-treated animals received an intracolonic dose of TNBS (80 mg/kg in saline and 250 l, 50% ethanol in water) (Fiorucci at al., 2001). Sham animals received vehicle only, with TNBS replaced by equivolume water. Rats were maintained in an inclined position (40°) for 30 min, then allowed to recover with food and water supplied. Rats were dosed daily with the respective compound, weighed, and scored for general health and disease progression. All rats were sacrificed on day 8 of experimentation unless they were sacrificed earlier. Disease progression and post-mortem colonic histopathology was scored by the following methods. PAR2 and tryptase co-localization were investigated by using immunohistochemistry.

Disease Activity Index (DAI).

DAI for both acute and chronic models was assessed and scored by an expert blinded to treatments. Scores incorporated mobility, gastrointestinal pathology, discomfort, and generalized sickness behaviour criteria (each scored 0-3). Any animal that reached stage 3 in any criteria was euthanized by $CO_2$ inhalation and recorded as a disease-related mortality. Scores were summed and expressed as total disease score (maximum 12). DAI was measured at endpoint only (10 h) in the acute study and daily in the chronic TNBS study.

Macroscopic Disease Index.

Colons were dissected post-mortem and given a macroscopic disease score based on that described previously (Bobin-Dubigeon et al., 2001) with some minor alterations (maximal score 14). The entire colon length was removed between the ileocolic and colorectal junction. Length and maximal distension width were measured. Sections of affected colon were taken for biochemical analysis, histology, and wet/dry weight.

Histology and Immunohistochemistry.

Tissue samples ware embedded in paraffin wax, cut on a microtome (5 m), and stained with either hematoxylin and eosin (H&E) or Alcian Blue, pH 1.0, and safranin-O using standard protocols. For immunohistochemistry, tissue was labelled with antibodies raised against PAR2 (N19 1:100, Santa Cruz Biotechnology, Inc., Santa Cruz, Calif.) and/or mast cell tryptase (AA1; 1:100; Abeam Inc., Cambridge, Mass.) by using standard 10 mM citrate antigen retrieval and 4-h (primary) incubation protocols. All fluorescence images were subject to background subtraction and brightness enhancement by using standard ImageJ algorithms (National Institutes of Health, Bethesda, Md.) to clarify staining patterns.

Bowel Wall Thickness.

Bowel wall thickness was measured by a researcher blinded to treatments. Measurements were made from H&E stained photomicrographs (20 lens) using Image software (1.42q). Image pixels were calibrated into micron (0.143 pixels/m), and the distance from outer circular muscle to the inner crypt base was measured.

Myeloperoxidase and ELISA.

Unfixed colon sections were homogenized in 4° C./0.5% hexadecyl trimethylammonium bromide/phosphate-buffered saline buffer (100 mg/mL w/v, pH 6.0) and centrifuged at 13,000 rpm for 10 mill at 4° C. Supernatant (100 l) was transferred (in duplicate) to a 96-well plate to which dianisidine (20 l, 2.85 mg/ml in 1% $H_2O_2$/phosphate-buffered saline) was added and mixed by aspiration. The plate was allowed to incubate for 15 min at room temperature (in the dark) then transferred to a fluorimeter (FLUOstar Optima; BMG Labtech GmbH, Offenburg, Germany). Absorbance was read at 450 nm. Data were expressed as absolute optical density units. Cytokine expression (tumor necrosis factor and interleukin-6) in tissue homogenates was measured by using ELISA (BD Biosciences, San Jose, Calif.) according to the manufacturer's instructions.

Data Analysts.

Experimental results were expressed as mean S.E.M. Data were analysed by using Prism software (v5.0a; Graph-Pad Software, San Diego, Calif.). Statistical comparisons were performed by using two-way repeated-measures ANOVA for temporal data sets involving three or more groups. For individual time points, data were analysed with one-way ANOVA., and groups were compared with Bonferroni planned comparisons. Significance was set at p 0.05.

Results.

Figure 23:
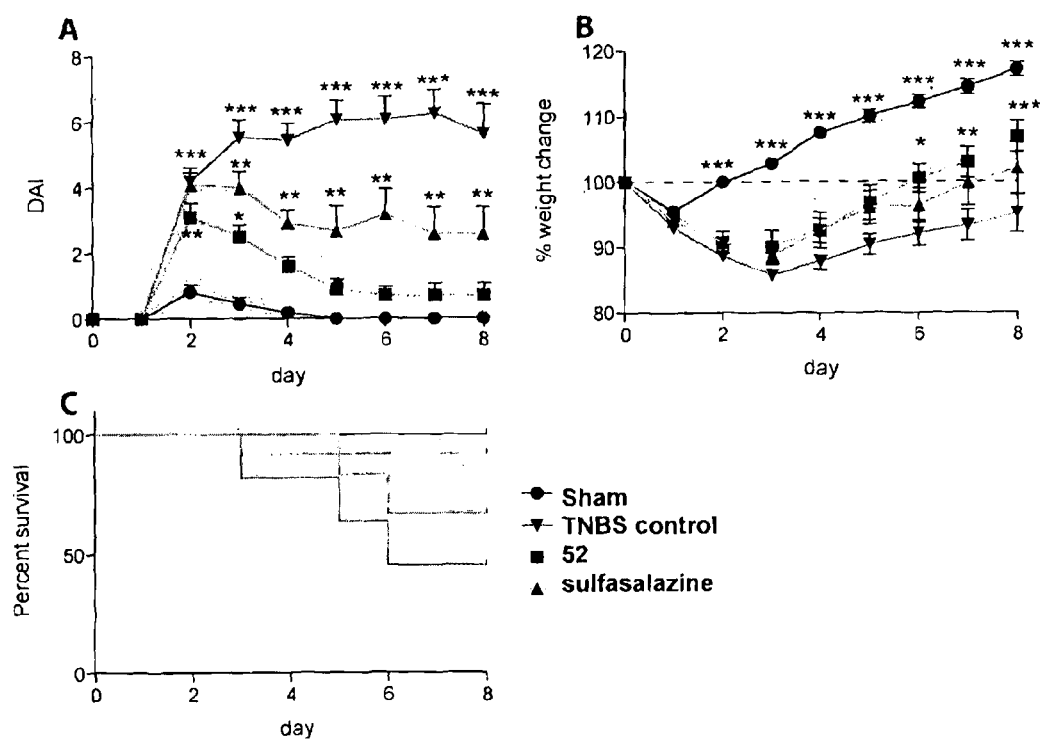
FIG. 23. Graphical representations of TNBS-induced disease-like symptoms in a TNBS-induced chronic colitis model in rats and attenuation thereof with sulfasalazine and compound 52.

Chronic colitis in rats was ameliorated by compound 52 (10 mg/kg/day p.o.), which reduced mortality and pathology (including colon obstruction, ulceration, wall thickness, and myeloperoxidase release) more effectively than the clinically used drug sulfasalazine (100 mg/kg/day p.o.). Both compound 52 sulfasalazine treatment showed marked improvements in DAI from day 2 onward compared with TNBS-controls (FIGS. 23 A and B; *$p<0.05$; $p<0.01$; *$p<0.001$ from sham; n=10; ANOVA two-way repeated measures planned comparison). Rats treated with compound 52 showed an almost complete recovery from DAI. Treatment with compound 52 was also much more effective than sulfasalazine in preventing TNBS-mediated mortality (FIG. 23 C, 8.3 versus 33.3% mortality, respectively, $p<0.05$). These disease-modifying properties for the PAR2 antagonist in both acute and chronic experimental colitis strongly support a pathogenic role for PAR2 and PAR2-activating proteases and therapeutic potential for PAR2 antagonism in inflammatory diseases of the colon.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A method of treating a disease or disorder selected from metabolic syndrome, obesity, type II diabetes, fibrosis and cardiovascular diseases comprising administering to a subject in need thereof an effective amount of a PAR2 antagonist represented by formula (I):

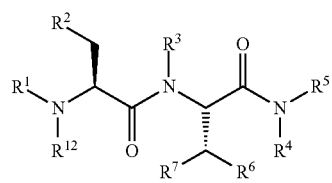

wherein

R¹ is hydrogen, $C_1$-$C_6$alkyl, aminoalkyl, hydroxyalkyl, or —C(O)R⁸;
  R⁸ is a 5- or 6-membered saturated or unsaturated heterocyclic ring comprising 1 to 3 heteroatoms selected from N and O, optionally substituted with one or more substituents selected from alkyl, alkoxy, amine, aminoalkyl, amidoalkyl, halo, hydroxy, trihaloalkyl, trihaloalkoxy or phenyl, wherein the phenyl group is optionally substituted with 1 to 3 substituents selected from alkyl, alkoxy, hydroxy, halo, nitro, trihaloalkyl, or trihaloalkoxy; or
R¹, together with the nitrogen atom to which it is attached, forms a mono- or bicyclic-nitrogen containing heterocycle, optionally substituted with alkyl;
R² is an aromatic or aliphatic $C_3$-$C_8$cyclic group or $C_3$-$C_8$heterocyclic group comprising 1 to 3 heteroatoms selected from N and O, wherein the $C_3$-$C_8$cyclic group or $C_3$-$C_8$heterocyclic group may be further substituted with one or more substituents selected from alkyl, amine, hydroxy, or the cyclic group or heterocyclic group is fused with an optionally substituted aromatic or aliphatic $C_3$-$C_8$cyclic group or $C_3$-$C_8$heterocyclic group;
R³ is hydrogen or $C_1$-$C_6$alkyl;
R⁴ is hydrogen, $C_1$-$C_6$alkyl, aminoalkyl or amidoalkyl;
R⁵ is a benzyl group optionally substituted with alkyl, aminoalkyl, alkoxy, $C_4$-$C_7$heterocycle, hydroxy, halo, nitro, dioxalane, trihaloalkyl, trihaloalkoxy or —C(O)NHCHR⁹R¹⁰;
R⁹ is —C(O)NH₂ and
R¹⁰ is a $C_2$-$C_5$aminoalkyl;
or
R⁴ and R⁵ combined, together with the nitrogen to which they are attached, form piperidine, optionally substituted with phenyl, benzyl, aminoalkyl, aminoaryl, amidoalkyl or a heterocycle; or
R⁴ and R⁵ combined, together with the nitrogen to which they are attached, form piperidine fused with an aromatic or aliphatic $C_3$-$C_8$cyclic group or $C_3$-$C_8$heterocyclic group;
wherein the phenyl, benzyl, aminoaryl, heterocycle or the aromatic or aliphatic $C_3$-$C_8$cyclic group or $C_3$-$C_8$heterocyclic group fused with piperidine may be further substituted with 1 to 3 substituents selected from alkyl, alkylamine, alkylamide, alkylsulfonyl, alkoxy, aminoalkyl, aminoaryl, amidoalkyl, arylamine, hydroxy, halo, nitro, oxo, optionally substituted phenyl, optionally substituted piperidine, dioxalane, trihaloalkyl, or trihaloalkoxy; or the aromatic or aliphatic $C_3$-$C_8$cyclic group or $C_3$-$C_8$heterocyclic group fused with the piperidine is further fused with an additional $C_6$-$C_{10}$cyclic or $C_6$-$C_{10}$heterocyclic group;
R⁶ is hydrogen or $C_1$-$C_6$alkyl;
R⁷ is $C_1$-$C_6$alkyl, amino, hydroxy, alkoxy, aminoalkyl, amidoalkyl, saturated or unsaturated cycloalkyl, or heterocycle; or R⁶ and R⁷ combined, together with the carbon to which they are attached, form $C_5$-$C_8$ aromatic or aliphatic cyclic group or heterocyclic group, optionally substituted with a group selected from alkyl, aminoalkyl, alkoxy, hydroxy, halo, nitro, trihaloalkyl or trihaloalkoxy; and
R¹² is hydrogen or $C_1$-$C_6$alkyl; and
salts thereof;
provided that the compound is not 5-isoxazoyl-Cha-Ile-spiro[indene-1,4'-piperidine], 5-isoxazoyl-Cha-Ile-spiro[indane-1,4'-piperidine], 5-isoxazoyl-Cha-Ile-spiro[octahydro-1H-indene-1,4'-piperidine] or 5-isoxazoyl-Cha-Ile-1,2,3,4-tetrahydroisoquinoline.

2. The method according to claim 1 wherein for compounds of the formula (I)
R¹ is hydrogen or —C(O)R⁸; wherein
  R⁸ is a 5- or 6-membered saturated or unsaturated heterocyclic ring comprising 1 to 3 heteroatoms selected from N and O, optionally substituted with one or more substituents selected from alkyl, alkoxy, amine, aminoalkyl, amidoalkyl, halo, hydroxy, trihaloalkyl, trihaloalkoxy or phenyl, wherein the phenyl group may be further optionally substituted with 1 to 3 substituents selected from alkyl, alkoxy, hydroxy, halo, nitro, trihaloalkyl, or trihaloalkoxy;
R⁶ is hydrogen or $C_1$-$C_6$alkyl; and
R⁷ is $C_1$-$C_6$alkyl, amino, hydroxy, alkoxy, aminoalkyl, amidoalkyl, saturated or unsaturated cycloalkyl, or heterocycle; and
salts thereof.

3. The method according to claim 1, wherein the compound of formula (I) is represented by the formula (Ia):

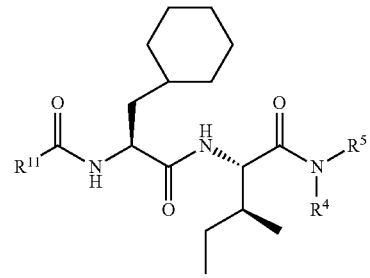

wherein
R¹¹ is a 5- or 6-membered unsaturated heterocyclic ring comprising 1 to 3 heteroatoms selected from N and O, optionally substituted with one or more groups selected from alkyl, amino, or phenyl, wherein the phenyl group may be further optionally substituted with 1 to 3 substituents selected from alkyl, alkoxy, hydroxy, halo, nitro, trihaloalkyl or trihaloalkoxy;
R⁴ is hydrogen, $C_1$-$C_6$alkyl, aminoalkyl or amidoalkyl;
R⁵ is a benzyl group substituted with alkyl, aminoalkyl, alkoxy, $C_4$-$C_7$heterocycle, hydroxy, halo, nitro, dioxalane, trihaloalkyl or trihaloalkoxy; or
R⁴ and R⁵ combined, together with the nitrogen to which they are attached, form piperidine, optionally substituted with phenyl, benzyl, aminoalkyl, aminoaryl, amidoalkyl or a heterocycle, or piperidine is fused with an aromatic or aliphatic $C_3$-$C_8$cyclic group or $C_3$-$C_8$heterocyclic group; wherein the phenyl, benzyl, aminoaryl, heterocycle or fused aromatic or aliphatic $C_3$-$C_8$cyclic group or $C_3$-$C_8$heterocyclic group may be further substituted with 1 to 3 substituents selected from alkyl, alkylamine, alkylamide, alkylsulfonyl, alkoxy, aminoalkyl, aminoaryl, amidoalkyl, arylamine, hydroxy, halo, nitro, oxo, optionally substituted phenyl, optionally substituted piperidine, dioxalane, trihaloalkyl, or trihaloalkoxy; or the fused aromatic or aliphatic $C_3$-$C_8$cyclic group or $C_3$-$C_8$heterocyclic group is fused with an additional $C_6$-$C_{10}$cyclic or $C_6$-$C_{10}$heterocyclic group; and salts thereof.

4. The method according to claim 1, wherein the compound of formula (I) is represented by the formula (Ib):

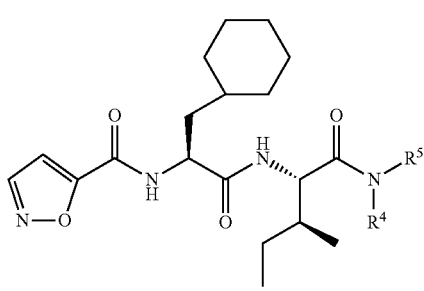

(Ib)

wherein $R^4$ is hydrogen, $C_1$-$C_6$alkyl, aminoalkyl or amidoalkyl;

$R^5$ is a benzyl group, optionally substituted with a group selected from alkyl, aminoalkyl, alkoxy, $C_4$-$C_7$heterocycle, hydroxy, halo, nitro, dioxalane, trihaloalkyl or trihaloalkoxy; or $R^4$ and $R^5$ combined, together with the nitrogen to which they are attached, form piperidine, optionally substituted with phenyl, benzyl, aminoalkyl, aminoaryl, amidoalkyl or a heterocycle, or piperidine is fused with an aromatic or aliphatic $C_3$-$C_8$cyclic group or $C_3$-$C_8$heterocyclic group; wherein the phenyl, benzyl, heterocycle or fused aromatic or aliphatic $C_3$-$C_8$cyclic group or $C_3$-$C_8$heterocyclic group may be further substituted with 1 to 3 substituents selected from alkyl, alkylamine, alkylamide, alkyloxy, aminoalkyl, amidoalkyl, hydroxy, halo, nitro, dioxalane, trihaloalkyl, or trihaloalkyloxy; and salts thereof.

5. A method according to claim 1, wherein the compound of formula (I) is represented by the formula (Ic):

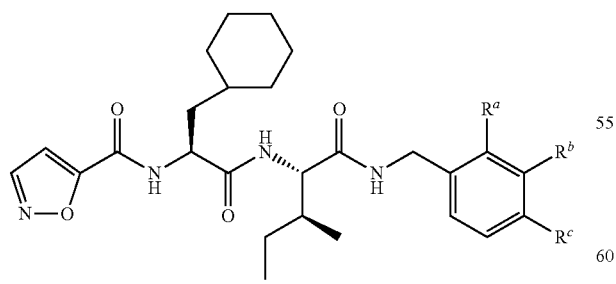

(Ic)

wherein $R^a$, $R^b$ and $R^c$ individually represent a group selected from hydrogen, alkyl, aminoalkyl, alkoxy, $C_4$-$C_7$heterocycle, hydroxy, halo, nitro, trihaloalkyl or trihaloalkoxy; or $R^a$ and $R^b$ or $R^b$ and $R^c$ combined form dioxalane; and salts thereof.

6. The method according to claim 1, wherein the compound of formula (I) is represented by the formula (Id):

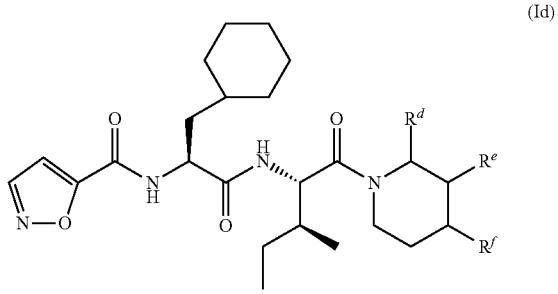

(Id)

wherein $R^d$, $R^e$ and $R^f$ independently represent a group selected from hydrogen, phenyl, benzyl, aminoalkyl, amidoalkyl, aminoaryl or a heterocycle, or $R^d$ and $R^e$ or $R^e$ and $R^f$ combined, form a fused aromatic or aliphatic $C_3$-$C_8$cyclic group or $C_3$-$C_8$heterocyclic group; wherein the phenyl, benzyl, heterocycle or fused aromatic or aliphatic $C_3$-$C_8$cyclic group or $C_3$-$C_8$heterocyclic group may be further substituted with 1 to 3 substituents selected from alkyl, alkoxy, aminoalkyl, amidoalkyl, hydroxy, halo, nitro, dioxalane, trihaloalkyl, or trihaloalkoxy; and salts thereof.

7. The method according to claim 1, wherein the compound of formula (I) is selected from the group consisting of:

5-isoxazoyl-Cha-Ile-aminomethyl-(2-methoxy)phenyl;
5-isoxazoyl-Cha-Ile-aminomethyl-(2-methyl)phenyl;
5-isoxazoyl-Cha-Ile-aminomethyl-(2-ethoxy)phenyl;
5-isoxazoyl-Cha-Ile-aminomethyl-(2-propoxy)phenyl;
5-isoxazoyl-Cha-Ile-aminomethyl-(2-isopropoxy)phenyl;
5-isoxazoyl-Cha-Ile-aminomethyl-(2-butoxy)phenyl;
5-isoxazoyl-Cha-Ile-aminomethyl-(2-isobutoxy)phenyl;
5-isoxazoyl-Cha-Ile-aminomethyl-(2-trifluoromethyl) phenyl;
5-isoxazoyl-Cha-Ile-aminomethyl-(3-trifluoromethoxy) phenyl;
5-isoxazoyl-Cha-Ile-aminomethyl-(2-trifluoromethyl) phenyl;
5-isoxazoyl-Cha-Ile-aminomethyl-(1,3-dioxalane)phenyl;
5-isoxazoyl-Cha-Ile-aminomethyl-(3,4-dichloro)phenyl;
5-isoxazoyl-Cha-Ile-aminomethyl-(2,4-dimethoxy)phenyl;
5-isoxazoyl-Cha-Ile-aminomethyl-(2,5-dimethoxy)phenyl;
5-isoxazoyl-Cha-Ile-aminomethyl-(3,4-dimethoxy)phenyl;
5-isoxazoyl-Cha-Ile-aminomethyl-(2,3-dimethoxy)phenyl;
5-isoxazoyl-Cha-Ile-aminomethyl-(2,3,4-trimethoxy) phenyl;
5-isoxazoyl-Cha-Ile-aminomethyl-(2,6-dimethoxy)phenyl;
5-isoxazoyl-Cha-Ile-aminomethyl-(2-methoxy-5-trifluoromethoxy)phenyl;
5-isoxazoyl-Cha-Ile-aminomethyl-(2,4-dimethoxy)phenyl;

5-isoxazoyl-Cha-Ile-aminomethyl-(3,5-bis(trifluoromethyl))phenyl;
5-isoxazoyl-Cha-Ile-(4-phenyl) piperidine;
5-isoxazoyl-Cha-Ile-4-(p-methoxy)phenyl piperidine;
5-isoxazoyl-Cha-Ile-4-(p-chloro)phenyl piperidine;
5-isoxazoyl-Cha-Ile-4-(o-trifluoromethyl)phenyl piperidine;
5-isoxazoyl-Cha-Ile-4-(o-phenyl)phenyl piperidine;
5-isoxazoyl-Cha-Ile-4-(m-phenyl)phenyl piperidine;
5-isoxazoyl-Cha-Ile-4-(p-phenyl)phenyl piperidine;
5-isoxazoyl-Cha-Ile-4-(p-phenoxy)phenyl piperidine;
5-isoxazoyl-Cha-Ile-4-(2,5-dimethoxy)phenyl piperidine;
5-isoxazoyl-Cha-Ile-(4-benzyl)piperidine;
5-isoxazoyl-Cha-Ile-2S-(tert-butylamide)piperidine;
5-isoxazoyl-Cha-Ile-4-(4-acetamide)phenyl piperidine;
5-isoxazoyl-Cha-Ile-3-(o-fluoro)aminophenyl piperidine;
5-isoxazoyl-Cha-Ile-3-(m-fluoro)aminophenyl piperidine;
5-isoxazoyl-Cha-Ile-3-(p-fluoro)aminophenyl piperidine;
5-isoxazoyl-Cha-Ile-3-(o-trifluoromethyl)aminophenyl piperidine;
5-isoxazoyl-Cha-Ile-3-(m-trifluoromethyl)aminophenyl piperidine;
5-isoxazoyl-Cha-Ile-3-(p-trifluoromethyl)aminophenyl piperidine;
5-isoxazoyl-Cha-Ile-spiro[chroman-2,4'-piperidine];
5-isoxazoyl-Cha-Ile-[(S)—N-(tert-butyl)]piperidine;
5-isoxazoyl-Cha-Ile-aminomethyl-benzimidazole;
5-isoxazoyl-Cha-Ile-aminomethyl-2-biphenyl;
5-isoxazoyl-Cha-Ile-aminomethyl-3-biphenyl;
5-isoxazoyl-Cha-Ile-aminomethyl-4-biphenyl;
5-isoxazoyl-Cha-Ile-aminomethyl-2-napthalene;
5-isoxazoyl-Cha-Thr(Me)-aminomethyl-(2-methoxy) phenyl;
Cha-Ile-spiro[indene-1,4'-piperidine];
5-isoxazoyl-Cha-Thr(Me)-spiro[indene-1,4'-piperidine];
5-(3-amino-isoxazoyl)-Cha-Ile-spiro[indene-1,4'-piperidine]; or
5-isoxazoyl-Cha-Thr(Me)-spiro[indene-1,4'-piperidine].

* * * * *